United States Patent
del Alamo de Pedro et al.

(10) Patent No.: US 11,771,379 B2
(45) Date of Patent: *Oct. 3, 2023

(54) MAPPING AND QUANTIFYING BLOOD STASIS AND THROMBUS RISK IN THE HEART

(71) Applicants: The Regents of the University of California, Oakland, CA (US); Fundación para la Investigación Biomédica del Hospital Gregorio Marañó, Madrid (ES)

(72) Inventors: Juan Carlos del Alamo de Pedro, San Diego, CA (US); Lorenzo Rossini, San Diego, CA (US); Andrew Kahn, San Diego, CA (US); Javier Bermejo, Madrid (ES); Pablo Martínez-Legazpi, Madrid (ES); Raquel Yotti Alvarez, Madrid (ES)

(73) Assignees: The Regents of the University of California, Oakland, CA (US); Fundación para la Investigación Biomédica del Hospital Gregorio Marañó, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,081

(22) Filed: Jun. 11, 2020

(65) Prior Publication Data
US 2020/0383644 A1 Dec. 10, 2020

Related U.S. Application Data

(63) Continuation of application No. 15/360,783, filed on Nov. 23, 2016, now Pat. No. 10,716,519.
(Continued)

(51) Int. Cl.
A61B 5/00 (2006.01)
A61B 5/029 (2006.01)
(Continued)

(52) U.S. Cl.
CPC .......... *A61B 5/7275* (2013.01); *A61B 5/0044* (2013.01); *A61B 5/029* (2013.01);
(Continued)

(58) Field of Classification Search
CPC ... A61B 5/7275; A61B 5/044; A61B 5/02028; A61B 5/0263; A61B 5/0285;
(Continued)

(56) References Cited

U.S. PATENT DOCUMENTS

| 4,501,279 A | * | 2/1985 | Seo .......................... A61B 8/13 |
| | | | 600/456 |
| 10,716,519 B2 | | 7/2020 | del Alamo de Pedro et al. |

(Continued)

FOREIGN PATENT DOCUMENTS

| JP | 2006/068524 | 3/2006 |
| WO | WO 2009/037484 | 3/2009 |

(Continued)

OTHER PUBLICATIONS

Hope et al., Clinical Evaluation of Aortic Coarctation With 4D Flow MR Imaging, Journal of Magnetic Resonance Imaging 31:711-718 (2010) (Year: 2010).*

(Continued)

*Primary Examiner* — John Denny Li
(74) *Attorney, Agent, or Firm* — Fish & Richardson P.C.

(57) ABSTRACT

The present disclosure provides methods for in-vivo assessment of the location and extent of blood flow stasis regions inside a cardiac chamber or blood vessel and systems for performing the methods. The disclosure provides methods for assessing risk of intracardiac or intravascular thrombus (Continued)

or of embolism originating in a cardiac chamber or vessel, and methods for assessing the need for and/or optimization of cardiac resynchronization therapy.

21 Claims, 15 Drawing Sheets
(15 of 15 Drawing Sheet(s) Filed in Color)

Related U.S. Application Data

(60) Provisional application No. 62/259,494, filed on Nov. 24, 2015.

(51) Int. Cl.
| | |
|---|---|
| A61B 5/02 | (2006.01) |
| A61B 5/026 | (2006.01) |
| A61B 8/08 | (2006.01) |
| G16H 50/30 | (2018.01) |
| G16H 30/40 | (2018.01) |
| A61B 5/0285 | (2006.01) |
| A61B 6/00 | (2006.01) |
| A61B 5/055 | (2006.01) |
| A61B 8/06 | (2006.01) |

(52) U.S. Cl.
CPC ........ *A61B 5/02028* (2013.01); *A61B 5/0263* (2013.01); *A61B 5/0285* (2013.01); *A61B 5/743* (2013.01); *A61B 6/507* (2013.01); *A61B 6/5205* (2013.01); *A61B 6/5223* (2013.01); *A61B 8/0883* (2013.01); *A61B 8/5223* (2013.01); *G16H 30/40* (2018.01); *G16H 50/30* (2018.01); *A61B 5/055* (2013.01); *A61B 8/06* (2013.01); *A61B 8/488* (2013.01); *A61B 8/5207* (2013.01); *A61B 2576/023* (2013.01)

(58) Field of Classification Search
CPC ......... A61B 5/029; A61B 5/743; A61B 5/055; A61B 6/507; A61B 6/5205; A61B 6/5223; A61B 8/0883; A61B 8/5223; A61B 8/06; A61B 8/488; A61B 8/5207; A61B 2576/023; G16H 50/30; G16H 30/40
See application file for complete search history.

(56) References Cited

U.S. PATENT DOCUMENTS

| | | | |
|---|---|---|---|
| 11,471,101 B2 | 10/2022 | del Alamo de Pedro et al. | |
| 2011/0071382 A1* | 3/2011 | Miyazaki | G01R 33/5635 600/413 |
| 2011/0144967 A1 | 6/2011 | Adirovich | |
| 2011/0257462 A1 | 10/2011 | Rodefeld et al. | |
| 2012/0150516 A1 | 6/2012 | Taylor | |
| 2012/0323118 A1* | 12/2012 | Menon Gopalakrishna | A61B 8/463 600/431 |
| 2013/0079610 A1 | 3/2013 | Al-Ali | |
| 2014/0233814 A1* | 8/2014 | Ikeda | G06T 7/0012 382/128 |
| 2014/0355863 A1 | 12/2014 | Xu et al. | |
| 2015/0065847 A1* | 3/2015 | Choi | G16Z 99/00 600/407 |
| 2015/0209498 A1 | 7/2015 | Franano et al. | |
| 2016/0210435 A1 | 7/2016 | Neumann | |
| 2017/0232166 A1 | 8/2017 | Potenziano et al. | |
| 2018/0031662 A1* | 2/2018 | Markl | G01R 33/56325 |
| 2023/0050982 A1 | 2/2023 | del Alamo de Pedro et al. | |

FOREIGN PATENT DOCUMENTS

| | | | |
|---|---|---|---|
| WO | WO-2009037484 A2 * | 3/2009 | ............... A61B 8/13 |
| WO | WO 2014/107769 | 7/2014 | |

OTHER PUBLICATIONS

Evans et al., Ultrasonic colour Doppler imaging, Interface Focus. Aug. 6, 2011; 1(4): 490-502 (Year: 2011).*
Gaschen et al., Optimizing Low Velocity Doppler Sonography in the Abdomen. 26th Annual Forum of the American College of Veterinary Internal Medicine (ACVIM 2008), https://www.vin.com/apputil/content/defaultadv1.aspx?pld=11262&id=3865707&print=1 (Year: 2008).*
Hendabadi et al., Topology of blood transport in the human left ventricle by novel processing of Doppler echocardiography, Ann Biomed Eng. Dec. 2013; 41(12): 10.1007/s10439-013-0853-z. Published online Jul. 2, 2013. doi: 10.1007/s10439-013-0853-z (Year: 2013).*
Fatkin et al., Relations between left atrial appendage blood flow velocity, spontaneous echocardiographic contrast and thromboembolic risk in vivo, J Am Coll Cardiol. Mar. 1994, 23 (4) 961-969 (Year: 1994).*
Abe et al., "Contrast echocardiography for assessing left ventricular vortex strength in heart failure: a prospective cohort study," European Heart Journal—Cardiovascular Imaging, Nov. 1, 2013, 14(11):1049-1060.
Benito et al., "Age-dependence of flow homeostasis in the left ventricle," Frontiers in physiology, Apr. 26, 2019, 10:1-12.
Bermejo et al., "Diastolic chamber properties of the left ventricle assessed by global fitting of pressure-volume data: improving the gold standard of diastolic function," Journal of Applied Physiology, Aug. 15, 2013, 115(4):556-568.
Chakraborty et al., "On the relationships between local vortex identification schemes," Journal of fluid mechanics, Jul. 1, 2005, 535:189-214.
Chan et al., "Reevaluation of the Harboe assay as a standardized method of assessment for the hemolytic performance of ventricular assist devices," Artificial organs, Aug. 2012, 36(8):724-730.
Chaturvedi et al., "Increased airway pressure and simulated branch pulmonary artery stenosis increase pulmonary regurgitation after repair of tetralogy of Fallot: real-time analysis with a conductance catheter technique," Circulation, Feb. 4, 1997, 95(3): 14 Pages.
Chivukula et al., "Left ventricular assist device inflow cannula angle and thrombosis risk," Circulation: Heart Failure, Apr. 2018, 11(4): 9 Pages.
Cortina et al., "Noninvasive assessment of the right ventricular filling pressure gradient. Circulation." Aug. 28, 2007, 116(9):1015-1023.
Cowger et al., "The development of aortic insufficiency in left ventricular assist device-supported patients," Circulation: Heart Failure, Nov. 2010, (6):668-674.
Del Álamo et al., "Self-similar vortex clusters in the turbulent logarithmic region," Journal of Fluid Mechanics, Aug. 1, 2006, 561:329-358.
Domenichini et al., "Intraventricular vortex flow changes in the infarcted left ventricle: numerical results in an idealised 3D shape," Computer Methods in Biomechanics and Biomedical Engineering, Feb. 1, 2011, 14(01):95-101.
Faludi et al., "Left ventricular flow patterns in healthy subjects and patients with prosthetic mitral valves: an in vivo study using echocardiographic particle image velocimetry," The Journal of thoracic and cardiovascular surgery, Jun. 1, 2010, 139(6):1501-1510.
Flores et al., "Vorticity organization in the outer layer of turbulent channels with disturbed walls," Journal of Fluid Mechanics, Nov. 25, 2007, 591:145-154.
Fraser et al., "A quantitative comparison of mechanical blood damage parameters in rotary ventricular assist devices: shear stress, exposure time and hemolysis index,"Journal of biomechanical engineering, Aug. 1, 2012 134(8): 11 Pages.

(56) References Cited

OTHER PUBLICATIONS

Gao et al., "How to optimize intracardiac blood flow tracking by echocardiographic particle image velocimetry? Exploring the influence of data acquisition using computer-generated data sets," European Heart Journal—Cardiovascular Imaging, Jun. 1, 2012, 13(6):490-499.
Goldberg et al., "Thirty-year trends (1975 to 2005) in the magnitude of, management of, and hospital death rates associated with cardiogenic shock in patients with acute myocardial infarction: a population-based perspective," Circulation, Mar. 2009, 119:1211-1219.
Goodwin et al., "Resolution of mitral regurgitation with left ventricular assist device support," The Annals of thoracic surgery, Sep. 1, 2017, 104(3):811-818.
Hellums JD, "1993 Whitaker Lecture: biorheology in thrombosis research. Annals of biomedical engineering," Sep. 1, 1994, 22(5):445-455.
Jorde et al., "Prevalence, significance, and management of aortic insufficiency in continuous flow left ventricular assist device recipients," Circulation: Heart Failure, Mar. 2014, 7(2):310-319.
Kirklin et al., "Eighth annual INTERMACS report: special focus on framing the impact of adverse events," The Journal of Heart and Lung Transplantation, Oct. 1, 2017, 36(10):1080-1086.
Klotz et al., "Proposing a novel technique to exclude the left ventricle with an assist device: insights from 4-dimensional flow magnetic resonance imaging," European Journal of Cardio-Thoracic Surgery, Sep. 1, 2016, 50(3):439-445.
Liao et al., "Ventricular flow dynamics with varying LVAD inflow cannula lengths: In-silico evaluation in a multiscale model," Journal of biomechanics, Apr. 27, 2018, 72: 26 Pages.
Lip et al., "Thromboembolism and antithrombotic therapy for heart failure in sinus rhythm," Thromb Haemost, 2012,108: 14 Pages.
Martinez-Legazpi et al., "Stasis mapping using ultrasound: a prospective study in acute myocardial infarction," JACC: Cardiovascular Imaging, Mar. 5, 2018, 11(3):514-515.
Mehra et al., "A fully magnetically levitated circulatory pump for advanced heart failure," New England journal of medicine, Feb. 2, 2017, 376(5):440-450.
O'Neill et al., "The current use of Impella 2.5 in acute myocardial infarction complicated by cardiogenic shock: results from the USpella Registry," Journal of interventional cardiology, Feb. 2014, 27(1):1-11.
Ouweneel et al., "Percutaneous Mechanical Circulatory Support Versus Intra-Aortic Balloon Pump in Cardiogenic Shock After Acute Myocardial Infarction," J Am Coll Cardiol, Jan. 24, 2017, 69(3):278-287.
Paul et al., "Shear stress related blood damage in laminar couette flow," Artificial organs, Jun. 2003, 27(6):517-529.
PCT International Preliminary Report on Patentability in International Appln. No. PCT/US2019/026146, dated Oct. 15, 2020, 9 pages.
PCT International Search Report and Written Opinion in International Appln. No. PCT/US2019/026146, dated Jun. 20, 2019, 16 pages.
Pedrizzetti et al., "Left ventricular fluid mechanics: the long way from theoretical models to clinical applications," Annals of biomedical engineering, Jan. 1, 2015 43(1): 15 Pages.
Pedrizzetti et al., "The vortex—an early predictor of cardiovascular outcome?" Nature Reviews Cardiology, Sep. 2014, 11(9): 9 Pages.
Pérez Del Villar et al., "The role of elastic restoring forces in right-ventricular filling," Cardiovascular research, Jul. 1, 2015, 107(1):45-55.
Perry et al., "A description of eddying motions and flow patterns using critical-point concepts," Annual Review of Fluid Mechanics, Jan. 1987, 19(1):125-155.
Platts et al., "Contrast microsphere destruction by a continuous flow ventricular assist device: an in vitro evaluation using a mock circulation loop," BioMed research international, Jan. 1, 2017, 2017: pp. 1-10.

Ponikowski et al.,"2016 ESC Guidelines for the diagnosis and treatment of acute and chronic heart failure," European Heart Journal, 37(27), 2129-2200.
Prisco et al., "Impact of LVAD implantation site on ventricular blood stagnation," ASAIO journal (American Society for Artificial Internal Organs: 1992), Jul. 2017, 63(4): 18 Pages.
Ramstack et al., "Shear-induced activation of platelets," Journal of biomechanics, Jan. 1, 1979, 12(2):113-125.
Reider et al., "Intraventricular thrombus formation in the LVAD-assisted heart studied in a mock circulatory loop," Meccanica, Feb. 1, 2017, 52(3): 14 Pages.
Rodevand et al., "Diastolic flow pattern in the normal left ventricle," Journal of the American Society of Echocardiography, Jun. 1, 1999, 12(6):500-507.
Rogers et al., "Intrapericardial left ventricular assist device for advanced heart failure," New England Journal of Medicine, Feb. 2, 2017, 376(5):451-460.
Rossini et al., "Clinical assessment of intraventricular blood transport in patients undergoing cardiac resynchronization therapy," Meccanica, Feb. 1, 2017, 52(3): 14 Pages.
Schinkel et al., "Safety and feasibility of contrast echocardiography for the evaluation of patients with HeartMate 3 left ventricular assist devices," Eur Heart J Cardiovasc Imaging, Jun. 1, 2018, 19(6): 4 Pages.
Sengupta et al., "Emerging trends in CV flow visualization," JACC Cardiovasc Imaging, Mar. 2012, 5(3):305-316.
Seo et al., "A coupled chemo-fluidic computational model for thrombogenesis in infarcted left ventricles," American Journal of Physiology—Heart and Circulatory Physiology, Jun. 1, 2016, 310(11):H1567-H1582.
Shah et al., "Left ventricular assist device outcomes based on flow configuration and pre-operative left ventricular dimension: an interagency registry for mechanically assisted circulatory support analysis," The Journal of Heart and Lung Transplantation, Jun. 1, 2017, 36(6): 28 Pages.
Slaughter et al., "Advanced heart failure treated with continuous-flow left ventricular assist device," New England Journal of Medicine, Dec. 3, 2009, 361(23):2241-2251.
Smiseth et al., "A reproducible and stable model of acute ischaemic left ventricular failure in dogs," Clinical Physiology, Jun. 1982, 2(3):225-239.
Therrien et al., "Impact of pulmonary valve replacement on arrhythmia propensity late after repair of tetralogy of Fallot," Circulation, May 22, 2001, 103(20):2489-2494.
Thiele et al., "Intraaortic balloon support for myocardial infarction with cardiogenic shock," New England Journal of Medicine, Oct. 4, 2012 367(14):1287-1296.
Uejima et al., "A new echocardiographic method for identifying vortex flow in the left ventricle: numerical validation," Ultrasound Med Biol, May 2010, 36(5):772-788.
Vu et al., "Mitral valve prosthesis design affects hemodynamic stasis and shear in the dilated left ventricle," Annals of biomedical engineering, May 15, 2019 , 47(5): 16 Pages.
Yancy et al., "2017 ACC/AHA/HFSA focused update of the 2013 ACCF/AHA guideline for the management of heart failure: a report of the American College of Cardiology/American Heart Association Task Force on Clinical Practice Guidelines and the Heart Failure Society of America," Journal of the American College of Cardiology, Jul. 31, 2017, 70(6):776-803.
Yotti et al., "Doppler-Derived Ejection Intraventricular Pressure Gradients Provide a Reliable Assessment of Left Ventricular Systolic Chamber Function," Circulation, Sep. 20, 2005, 112(12):1771-1779.
Yotti et al., "Noninvasive estimation of the rate of relaxation by the analysis of intraventricular pressure gradients," Circulation: Cardiovascular Imaging, Mar. 2011, 4(2):94-104.
Zhang et al., "Assessment of left ventricular 2D flow pathlines during early diastole using spatial modulation of magnetization with polarity alternating velocity encoding: a study in normal volunteers and canine animals with myocardial infarction," Magnetic resonance in medicine, Sep. 2013, 70(3):766-775.
Arboix et al., "Cardioembolic stroke: clinical features, specific cardiac disorders and prognosis," Curr Cardiol Rev 6: 150-61, 2010.

(56) References Cited

OTHER PUBLICATIONS

Auricchio et al. "Long-term clinical effect of hemodynamically optimized cardiac resynchronization therapy in patients with heart failure and ventricular conduction delay," J Am Coll Cardiol 39(12):2026-2033, 2002.
Bakalli el al., "Prevalence of left chamber cardiac thrombi in patients with dilated left ventricle at sinus rhythm: the role of transesophageal echocardiography," J Clin Ultrasound 41(1): 38-45, 2013.
Benito et al., "Heart rate and AV delay modify left ventricular filling vortex properties," Circulation 126:A18099, 2012.
Bermejo et al, "The Clinical Assessment of Intracardiac Flows," Ann Rev Fluid Mech 47: 315-42, 2015.
Bermejo et al., "Intraventricular vortex properties in non-ischemic dilated cardiomyopathy," Am J Physiol Heart Circ Physiol 306: H718-29, 2014.
Bluestein., "Research approaches for studying flow-induced thromboembolic complications in blood recirculating devices," Expert Rev Med Devices 1(1): 65-80, 2004.
Bolger et al., "Transit of blood flow through the human left ventricle mapped by cardiovascular magnetic resonance," J Cardiovasc Magn Reson 9 (5):741-747, 2007.
Bristow et al., "Cardiac-resynchronization therapy with or without an implantable defibrillator in advanced chronic heart failure," New England Journal of Medicine 350 (21):2140-2150, 2004.
Busch et al., "Reconstruction of divergence-free velocity fields from cine 3D phase-contrast flow measurements," Magn Reson Med 69: 200-10, 2013.
Chorin., "The numerical solution of the Navier-Stokes equations for an incompressible fluid," Bull. Am. Math. Soc. 73: 928-31, 1967.
Devesa et al., "Prediction of intraventricular thrombosis by quantitative imaging of stasis: A pilot color-doppler study inpatients with acute myocardial infarction," J Am Coll Cardiol 65 (10S), 2015.
Eriksson et al., "Four-dimensional blood flow-specific markers of LV dysfunction in dilated cardiomyopathy," Eur Heart J Cardiovasc Imaging 14: 417-24, 2013.
Eriksson et al., "Quantification of presystolic blood flow organization and energetics in the human left ventricle," Am J Physiol Heart Circ Physiol 300(6): H2135-41, 2011.
Eriksson et al., "Semi-automatic quantification of 4D left ventricular blood flow," J Cardiovasc Magn Reson 12: 9, 2010.
Esmaily-Moghadam et al., "A non-discrete method for computation of residence time in fluid mechanics simulations," Phys Fluids 25, 25: 110802, 2013.
Evans et al., "Ultrasonic colour Doppler imaging," Interface Focus, 2011, 1(4):490-452.
Farwell et al., "How many people with heart failure are appropriate for biventricular resynchronization?" Eur Heart J 21 (15):1246-1250, 2000.
Fredriksson et al., "4-D blood flow in the human right ventricle," Am J Physiol Heart Circ Physiol 301 (6):H2344-2350, 2011 doi:10.1152/ajpheart.00622.2011.
Garcia et al., Two-dimensional intraventricular flow mapping by digital processing conventional color-Doppler echocardiography images. IEEE Trans Med Imaging 29(10): 1701-13, 2010.
Garcia-Alvarez et al., "Noninvasive monitoring of serial changes in pulmonary vascular resistance and acute vasodilator testing using cardiac magnetic resonance," J Am Coll Cardiol 62: 1621-31, 2013.
Gardiner, "Handbook of stochastic methods for physics, chemistry, and the natural sciences," Berlin; New York: Springer. 415 pages, 2004.
Gaschen et al., "Optimizing low velocity Doppler sonography in the abdomen," 26th Annual Forum of the American College of Veterinary Internal Medicine (ACVIM 2008), https://www.vin.com/apputil/conten/defaultadv1.aspx?pId=11262&id=3865707&print=1 (Year:2008).
Gharib et al., "Optimal vortex formation as an index of cardiac health," Proc Natl Acad Sci U S A 103 (16):6305-6308, 2006. doi:10.1073/pnas.0600520103.
Goliasch et al., "CRT improves LV filling dynamics: insights from echocardiographic particle imaging velocimetry," JACC Cardiovasc Imaging 6 (6):704-713, 2013.
Gonzalez et al., "Automated Axial Right Ventricle to Left Ventricle Diameter Ratio Computation in Computed Tomography Pulmonary Angiography," PLoS One 10(5): e0127797.
Gorcsan et al., "Echocardiography for cardiac resynchronization therapy: recommendations for performance and reporting—a report from the American Society of Echocardiography Dyssynchrony Writing Group endorsed by the Heart Rhythm Society," J Am Soc Echocardiogr 21 (3): 191-213, 2008.
Guha et al., "Heart failure epidemiology: European perspective," Curr Cardiol Rev 9 (2):123-127, 2013.
Hendabadi et al., "Topology of blood transport in the human left ventricle by novel processing of Doppler echocardiography," Ann Biomed Eng 41(12): 2603-16.
Homma et al., "Warfarin and aspirin in patients with heart failure and sinus rhythm," N Engl J Med 366: 1859-69, 2012.
Hong et al., "Characterization and quantification of vortex flow in the human left ventricle by contrast echocardiography using vector particle image velocimetry," J Am Coll Cardiol Img 1: 705-17, 2008.
Hope et al., "Clinical evaluation of aortic coarctation with 4D flow MR imaging," Journal of Magnetic Resonance Imaging, 2010, 31:711-718.
International Search Report and Written Opinion in Application No. PCT/US2016/063626, dated Feb. 2, 2017, 13 pages.
Jozsa et al., "Modelling Residence Time as Advection-Diffusion With Zero-Order Reaction Kinetics," Proceedings of the Hydroinformatics 2000 Conference, Cedar Rapids, Iowa.
Kass., "Cardiac resynchronization therapy," J Cardiovasc Electrophysiol 16 Suppl 1:S35-41, 2005.
Kedia et al., "Usefulness of atrioventricular delay optimization using Doppler assessment of mitral inflow in patients undergoing cardiac resynchronization therapy," Am J Cardiol 98 (6):780-785, 2006.
Kerwin et al., "Ventricular contraction abnormalities in dilated cardiomyopathy: effect of biventricular pacing to correct interventricular dyssynchrony," J Am Coll Cardiol 35 (5):1221-1227, 2000.
Kilner et al., "Asymmetric redirection of flow through the heart," Nature 404 (6779):759-761, 2000.
Kormos., "Left ventricular assist device pump thrombosis: Understanding mechanisms as a key to causality," J Thorac Cardiovasc Surg 149: 673-4, 2015.
Lang et al., "Recommendations for cardiac chamber quantification by echocardiography in adults: an update from the American Society of Echocardiography and the European Association of Cardiovascular Imaging," J Am Soc Echocardiogr 28(1): 1-39 e14, 2015.
Leonard et al., "The role of convection and diffusion on platelet adhesion and aggregation," Ann N Y Acad Sci 201: 329-42, 1972.
Littmann et al., "Hemodynamic implications of left bundle branch block," J Electrocardiol 33 Suppl:115-121, 2000.
Lowe., "Virchow's triad revisited: abnormal flow," Pathophysiol Haemost Thromb 33: 455-7, 2003.
Mangual et al., "Describing the highly three dimensional Right Ventricle flow," Ann Biomed Eng 40: 1790-801, 2012.
Martinez-Legazpi, et al., "Contribution of the diastolic vortex ring to left ventricular filling," J Am Coll Cardiol 64 (16):1711-1721, 2014 doi: 10.1016/j.jacc.2014,06,1205.
Massie et al., "Randomized trial of warfarin, aspirin, and clopidogrel in patients with chronic heart failure: the Warfarin and Antiplatelet Therapy in Chronic Heart Failure (WATCH) trial," Circulation 119: 1616-24, 2009.
May-Newman et al., "Thromboembolism is linked to intraventricular flow stasis in a patient supported with a left ventricle assist device," ASAIO J 59: 452-5, 2013.
Mittal., "A versatile sharp interface immersed boundary method for incompressible flows with complex boundaries," Journal of Computational Physics 227: 4825-52, 2008.
Mody., "Influence of Brownian motion on blood platelet flow behavior and adhesive dynamics near a planar wall," Langmuir 23: 6321-8, 2007.

(56) References Cited

OTHER PUBLICATIONS

Pavlopoulos et al., "Recent advances in cardiac resynchronization therapy: echocardiographic modalities, patient selection, optimization, non-responders—all you need to know for more efficient CRT," Int J Cardiovasc Imaging 26 (2):177-191, 2010 doi:10.1007/s10554-009-9523-5.
Pedrizzetti et al., "Changes in electrical activation modify the orientation of left ventricular flow momentum: novel observations using echocardiographic particle image velocimetry," Eur Heart J Cardiovasc Imaging, 2015 doi:10.1093/ehjci/jev137.
Pedrizzetti et al., "Nature optimizes the swirling flow in the human left ventricle," Phy Rev Lett 95 (10):108101, 2005.
Quaini et al., "Numerical characterization of hemodynamics conditions near aortic valve after implantation of Left Ventricular Assist Device," Math Biosci Eng 8: 785-806, 2011.
Richter et al., "Cardiology is flow," Circulation 113 (23):2679-2682, 2006.
Rossini et al., "A clinical method for mapping and quantifying blood stasis in the left ventricle," J Biomech In press, 2015.
Sawhney et al., "Randomized prospective trial of atrioventricular delay programming for cardiac resynchronization therapy," Heart Rhythm 1 (5):562-567, 2004 doi:10.1016/j.hrthm.2004.07.006.
Saxon et al., "Acute effects of intraoperative multisite ventricular pacing on left ventricular function and activation/contraction sequence in patients with depressed ventricular function," J Cardiovasc Electrophysiol 9 (1):13-21, 1998.
Seo et al., "Effect of diastolic flow patterns on the function of the left ventricle," Phys Fluids 25: 110801, 2013.
Stanton et al., "How should we optimize cardiac resynchronization therapy?" Eur Heart J 29(20):2458-2472, 2008 doi:10.1093/eurheartj/ehn380.
Tarbell., "Mass transport in arteries and the localization of atherosclerosis," Annu Rev Biomed Eng 5:79-118, 2003.
Thompson et al., "Fast measurement of intracardiac pressure differences with 2D breath-hold phase-contrast MRI," Magn Reson Med 49 (6):1056-1066, 2003.
Toeg et al., "An update on mechanical circulatory support for heart failure therapy," Curr Opin Cardiol 29: 167-73, 2014.
Waggoner et al., "Left ventricular diastolic filling prior to cardiac resynchronization therapy: implications for atrioventricular delay programming," Pacing Clin Electrophysiol 31 (7):838-844, 2008 doi:10.1111/j.1540-8159.2008.01097.x.
Watanabe et al., "The looped heart does not save energy by maintaining the momentum of blood flowing in the ventricle," Am J Physiol Heart Circ Physiol 294: H2191-6, 2008.
Wigstrom et al., "Particle trace visualization of intracardiac flow using time-resolved 3D phase contrast MRI," Magn ResonMed 41 (4):793-799, 1999.
Wong K et al., "Intraventricular flow patterns and stasis in the LVAD-assisted heart," J Biomech 47:1485-94, 2014.
Xiao et al., "Effects of abnormal activation on the time course of the left ventricular pressure pulse in dilated cardiomyopathy," Br Heart J 68 (4):403-407, 1992.
Xiao et al., "Natural history of abnormal conduction and its relation to prognosis in patients with dilated cardiomyopathy," Int J Cardiol 53 (2):163-170, 1996.
Yang et al., "Flow and myocardial interaction: an imaging perspective," Philos Trans R Soc Lond B Biol Sci 362 (1484):1329-1341, 2007. doi:10.1098/rstb.2007.2119.
Zhang et al., "Different independent susceptibility markers for first-ever cerebral infarction and myocardial infarction in young patients," J Neurol 259: 1420-5, 2012.
Zhang et al., "The role of repeating optimization of atrioventricular interval during interim and long-term follow-up after cardiac resynchronization therapy," Int J Cardiol 124 (2):211-217, 2008 doi:10.1016/j.ijcard.2007.02.043.
Zwanenburg et al., "Regional timing of myocardial shortening is related to prestretch from atrial contraction: assessment by high temporal resolution MRI tagging in humans," Am J Physiol Heart Circ Physiol 288 (2):H787-794, 2005.
Rodriguez et al., "Intracardiac flow visualization: current status and future directions," European Heart Journal—Cardiovascular Imaging, Nov. 1, 2013, 14(11):1029-1038.

\* cited by examiner

MAPPING AND QUANTIFYING BLOOD STASIS AND THROMBUS RISK IN THE HEART

CROSS-REFERENCE TO RELATED APPLICATIONS

The application is a continuation of U.S. application Ser. No. 15/360,783, filed on Nov. 23, 2016, which the benefit of U.S. Provisional Application Ser. No. 62/259,494, filed Nov. 24, 2015. The disclosure of the prior application is considered part of (and are incorporated by reference in) the disclosure of this application.

FEDERALLY SPONSORED RESEARCH OR DEVELOPMENT

This invention was made with Government support under Grant No. 1R21 HL108268-01 awarded by the National Institutes of Health. The Government has certain rights in the invention.

TECHNICAL FIELD

This invention relates to generally to cardiac care, and more particularly to methods for determining intracardiac thrombosis risk in a patient by assessing the location and extent of intraventricular stasis regions inside a cardiac chamber.

BACKGROUND

Cardiovascular diseases are the leading cause of mortality worldwide and are projected to cause more than 20 million deaths per year by 2030. Cardioembolic stroke is one of the most devastating consequences of cardiac diseases, both in terms of mortality and disability. In embolic strokes, a blood clot or other material travels to the brain from another site and occludes a blood vessel, thereby depriving the brain of the needed blood flow (and associated oxygen and glucose supplies); this results in the death of the cells that are usually supplied by this blood flow. The most common source for these emboli is the heart. Blood clots, otherwise known as thrombi, can form in patients with atrial fibrillation, heart valves, artificial materials (e.g., artificial hearts, vascular stents, and the like), or significant heart disease.

Three major mechanisms promote intracardiac thrombosis and embolism in cardiac diseases. First, endocardial injury, due to surgery, chronic stretch or ischemic necrosis, activates clot formation by exposing pro-coagulation factors of the basal membrane. Additionally, cardiac diseases are frequently associated with chronic inflammation, and increased catecholamine and inflammatory cytokine levels, which induce a systemic hypercoagulable state. Finally, blood flow stagnation triggers the activation of the coagulation system. These three predisposing factors are classically known as "Virchow's triad" (Lowe 2003). Diseases such as atrial fibrillation, myocardial infarction, dilated and hypertrophic cardiomyopathies are well-established conditions that increase the risk of cardiac embolisms by a combination of these three mechanisms.

Anticoagulation therapy has proven to be effective for decreasing the risk of cardioembolic events. However, the benefits of anticoagulation are frequently neutralized by the increased hemorrhagic risk associated with this therapy (Massie et al 2009). In fact, most clinical trials assessing the efficacy of primary prevention of anticoagulation therapy in non-atrial fibrillation (non-AF) cardioembolic diseases have been negative or neutral (Bakalli et al 2013, Homma et al 2012). These trials have been based on clinical risk factors and demographic variables, because precision individualized risk assessment methods are lacking. We hypothesize that imaging-based biomarkers are particularly well suited for this purpose.

Mechanical left-ventricular-assisted-devices (LVADs) are being used as temporary and destination therapies in an increasing number of patients with end-stage heart failure (HF) (Toeg et al 2014). However, intraventricular thrombosis is a well-recognized complication of LVADs and may lead to device malfunction and embolism. A quantitative and individualized topologic assessment of the chamber regions at particular risk for thrombus development may help to define the ideal locations for the insertion of the LVAD cannulas on a patient-specific basis and, to optimize the device operating settings.

Flow in the heart involves complex fluid transport and mixing processes (Bermejo et al 2015). Intracardiac transport and mixing depends on convoluted trajectories of flow inside the chambers (Kilner et al 2000, Wigstrom et al 1999, Zhang et al 2012) as well as on the dynamical interactions between incoming flow and residual flow from preceding cycles (Bolger et al 2007). In the healthy heart, these phenomena result in a small residual volume with no associated blood stasis. However, intraventricular flow patterns are significantly altered by disease (Bermejo et al 2014, Eriksson et al 2013, Hong et al 2008, Rodriguez Munoz et al 2013). How these disturbed flow dynamics may lead to increased blood stasis is only beginning to be understood (Eriksson et al 2013, Hendabadi et al 2013).

Currently, there are no tools capable of a high-throughput measurement of flow stasis in the clinical setting. It would be desirable, therefore, to provide methods capable of a high-throughput measurement of flow stasis in the clinical setting to inform treatment options for patients at risk for thrombus formation.

SUMMARY

In some aspects, the disclosure provides methods for identifying regions of blood flow stasis inside a cardiac chamber or blood vessel of a subject comprising obtaining flow-velocity images of blood inside a cardiac chamber or blood vessel of the subject, calculating the residence time ($T_R$), the standard deviation of the residence time ($\sigma_R$), kinetic energy, and/or rate of distortion of blood particles inside the cardiac chamber or blood vessel using the flow-velocity images to generate numerical metrics of blood flow, and generating residence time ($T_R$), kinetic energy, and/or rate of distortion maps using the numerical metrics to identify and characterize regions of blood flow stasis.

In some aspects, the disclosure provides methods for estimating risk of intracardiac or intravascular thrombus or of embolism originating in a cardiac chamber or blood vessel in a subject comprising obtaining flow-velocity images of blood inside any cardiac chamber or blood vessel, calculating the residence time ($T_R$), the standard deviation of the residence time ($\sigma_R$), the kinetic energy, and/or rate of distortion of blood particles inside the cardiac chamber or blood vessel using the flow-velocity images to generate numerical metrics of blood flow, and generating an intracardiac or intravascular thrombus risk assessment using the numerical metrics to determine regions of blood flow stasis inside the cardiac chamber or blood vessel, wherein regions of blood flow stasis are predictive of risk of intracardiac or intravascular thrombus or of embolism.

In some embodiments of all aspects, generating numerical metrics of blood flow comprises calculating the blood flow's residence time ($T_R$) inside the cardiac chamber or blood vessel. In some embodiments of all aspects, generating numerical metrics of blood flow comprises calculating the standard deviation of the residence time ($\sigma_R$) inside the cardiac chamber or blood vessel. In some embodiments of all aspects, generating numerical metrics of blood flow comprises calculating and comparing both the blood flow's residence time ($T_R$) and the standard deviation of the residence time ($\sigma_R$) inside the cardiac chamber or blood vessel. In some embodiments, a $T_R$ that is high compared to $\sigma_R$ is indicative of blood flow stasis.

In some embodiments of all aspects, generating numerical metrics of blood flow comprises calculating the blood flow's standard deviation of the residence time ($\sigma_R$) inside the cardiac chamber or blood vessel. In some embodiments, calculating the blood flow's standard deviation of the residence time is performed for regions with high blood flow residence time inside the cardiac chamber.

In some embodiments of all aspects, generating numerical metrics of blood flow comprises calculating the blood flow's kinetic energy inside the cardiac chamber or blood vessel. In some embodiments, calculating the blood flow's kinetic energy is performed for regions with high blood flow residence time inside the cardiac chamber or blood vessel.

In some embodiments of all aspects, generating numerical metrics of blood flow comprises calculating the rate of distortion of blood flow inside the cardiac chamber or blood vessel. In some embodiments, generating numerical metrics of blood flow comprises calculating the blood flow's rate of distortion in regions with high blood flow residence time inside the cardiac chamber or blood vessel.

In some embodiments of all aspects, generating numerical metrics of blood flow comprises calculating a blood stasis timescale index.

In some embodiments of all aspects, generating numerical metrics of blood flow further comprises calculating additional descriptors of the distribution of values of residence time from its probability density function p(x,t,T), in addition to $T_R$ and its standard deviation $\sigma_R$. In some embodiments, such additional descriptors include, without limitation, skewness, kurtosis, median inter-quartile range, and/or other inter-percentile ranges of p(x,t,T).

In some embodiments of all aspects, generating numerical metrics of blood flow comprises calculating the size, shape, mobility, distance to the chamber wall, and perimeter in contact with the chamber wall of regions with blood stasis, e.g., of regions with high blood flow residence time, of regions with high blood flow residence time and low distortion rate, and regions with high residence time and high blood stasis timescale index. In some embodiments, large, immobile regions, or/and regions that have more perimeter in contact with chamber walls are identified as more prone to blood flow stasis.

The cardiac chamber or blood vessel can be any cardiac chamber or blood vessel in which the blood velocity can be resolved. For example, the cardiac chamber can be the left ventricular chamber, left atrium chamber, left atrial appendage, right-ventricular chamber, or right atrium chamber. In some embodiments, regions of blood flow stasis are determined by calculating the residence time ($T_R$), the standard deviation of the residence time ($\sigma_R$), kinetic energy, and/or rate of distortion of blood particles in more than one cardiac chamber or blood vessel (e.g., 2, 3, 4, 5, or more cardiac chambers or blood vessels).

In some embodiments of all aspects, obtaining flow-velocity images of blood inside a cardiac chamber or blood vessel is performed using a medical image-based apparatus able to determine blood flow velocity field. For example, the medical image-based apparatus can be an echocardiogram apparatus, a magnetic resonance imaging (MRI) apparatus, an echocardiographic imaging apparatus, a 2D color-Doppler velocimetry (echo-CDV) apparatus, an echo-particle-image-velocimetry (echo-PIV) apparatus, a synthetic aperture ultrasound apparatus or a transverse oscillation ultrasound vector velocimetry apparatus, or other medical image-based apparatus known to the skilled artisan. Flow-velocity images obtained from the medical image-based apparatus and suitable for the methods described herein include one, two, or three-dimensional images resolved in time.

In some embodiments of all aspects, multiple flow-velocity images are obtained using different velocity scales, and wherein data from the obtained flow-velocity images are retrospectively merged to generate flow maps, residence time ($T_R$) maps, kinetic energy maps, rate of distortion maps, or combinations thereof.

In some embodiments of all aspects, calculating the residence time ($T_R$) of blood particles includes utilizing the equation:

$$\frac{\partial T_R}{\partial t} + \nabla \cdot (\vec{v} T_R) = 1.$$

In some embodiments of all aspects, calculating the residence time ($T_R$) of blood particles in the presence of measurement noise includes utilizing the equation:

$$\frac{\partial T_R}{\partial t} + \nabla \cdot (\vec{v} T_R) = 1 + \nabla \cdot (k \nabla T_R),$$

where the diffusivity coefficient k represents the uncertainty introduced by the random noise in the measurement of the velocity field. In some embodiments of all aspects, the numerical metrics of blood flow are used to identify size and/or location of blood flow stasis within the cardiac chamber or blood vessel.

In some embodiments of all aspects, calculating the standard deviation of $T_R$ caused by the noise in the velocity measurements includes utilizing the equation:

$$\sigma_R(x,t) = \sqrt{S_R(x,t) - T_R^2(x,t)}$$

where $S_R$ and $T_R$ obey the equations:

$$\frac{\partial T_R}{\partial t} + \nabla \cdot (\vec{v} T_R) = 1 + \nabla \cdot (k \nabla T_R)$$

$$\frac{\partial S_R}{\partial t} + \nabla \cdot (\vec{v} S_R) = 2 T_R + \nabla \cdot (k \nabla S_R),$$

where the diffusivity coefficient k represents the uncertainty introduced by the random noise in the measurement of the velocity field. In some embodiments of all aspects, the numerical metrics of blood flow are used to identify size and/or location of blood flow stasis within the cardiac chamber or blood vessel.

In some embodiments of all aspects, a distribution of values of residence time emerges at each instant of time and each point in space, which distribution of values of residence time is caused by noise in the velocity measurements, wherein a probability density function of distribution p(T, x,t) is calculated utilizing the equation:

$$\frac{\partial p}{\partial t} = -\frac{\partial(vp)}{\partial x} - \frac{\partial p}{\partial T} + \frac{\partial}{\partial x}\left(k\frac{\partial p}{\partial x}\right).$$

and wherein diffusivity coefficient k represents uncertainty introduced by the noise in the velocity measurements.

In some embodiments of all aspects, the numerical metrics of blood flow are used to identify size and/or location of blood flow stasis within the cardiac chamber or blood vessel.

In some embodiments of all aspects, generating numerical metrics of blood flow comprises calculating the size, shape, mobility, distance to the chamber wall, and perimeter in contact with the chamber wall of regions with high blood flow residence time.

In some embodiments of all aspects, generating numerical metrics of blood flow comprises calculating the blood flow's kinetic energy in regions with high blood flow residence time inside the cardiac chamber. In some embodiments of all aspects, generating numerical metrics of blood flow comprises calculating the rate of distortion of blood flow in regions with high blood flow residence time inside the cardiac chamber. In some embodiments of all aspects, generating numerical metrics of blood flow comprises calculating the blood stasis timescale stasis index in regions with high blood flow residence time inside the cardiac chamber.

In some embodiments of all aspects, the numerical metrics of blood flow are used to identify size and/or location of blood flow stasis within the cardiac chamber or blood vessel.

In some embodiments of all aspects, the methods provided herein further comprise identifying subjects having regions of increased blood flow stasis as being at high risk of intracardiac thrombus, and identifying subjects not having regions of blood flow stasis as being at low risk of intracardiac thrombus.

In some embodiments, the methods further comprise the prescription and dosing of anti-coagulant therapy to subjects identified as being at increased risk of intracardiac thrombus. Examples of such anticoagulant therapy include, but are not limited to, vitamin K antagonists, heparin and derivative substances, direct factor Xa inhibitors, and direct thrombin inhibitors.

In some aspects, the disclosure provides methods comprising obtaining flow-velocity images of blood inside a cardiac chamber or blood vessel of a subject, calculating the residence time (TR), the standard deviation of the residence time ($\sigma_R$), kinetic energy, and/or rate of distortion of blood particles inside the cardiac chamber or blood vessel using the flow-velocity images to generate numerical metrics of blood flow, and generating residence time (TR), kinetic energy, and/or rate of distortion maps using the numerical metrics to identify and characterize regions of blood flow stasis as an indicator of the efficacy of or need for cardiac resynchronization therapy in the subject.

In some embodiments of the methods provided herein, the subject is undergoing cardiac resynchronization therapy. For such subjects, the methods can further comprise altering the cardiac resynchronization therapy protocol for subjects identified as having regions of altered or increased blood flow stasis. Altering the cardiac resynchronization therapy protocol may include, for example, altering the atrio-ventricular (AV) delay, altering the ventriculo-ventricular (VV) delay, or altering the location of a pacemaker or pacemaker lead.

In some embodiments of the methods provided herein, the subject is not undergoing cardiac resynchronization therapy. For such subjects, the methods can further comprise selecting subjects having regions of altered or increased blood flow stasis as being in need cardiac resynchronization therapy.

In some aspects, the disclosure provides method for optimizing cardiac resynchronization therapy in a subject comprising calculating the residence time (TR) of blood particles inside the cardiac chamber or blood vessel using the flow-velocity images to generate numerical metrics of blood flow, calculating the residence time (TR) of blood particles inside the cardiac chamber or blood vessel using the flow-velocity images to generate numerical metrics of blood flow, generating a residence time map to automatically segment and delineate the blood volume that is injected into the cardiac chamber or blood vessel each cardiac cycle, generating a residence time map to automatically segment and delineate the blood volume that is ejected out of the cardiac chamber or blood vessel each cardiac cycle, generating a residence time map to automatically segment and delineate the direct blood volume that is comprised by the fluid that is both injected during each cardiac cycle and also ejected during the same cycle; and generating a residence time map to automatically segment and delineate the residual blood volume that does not mix and does not overlap with injected or ejected blood volumes each cardiac cycle.

In some embodiments of all aspects, the subject is not undergoing cardiac resynchronization therapy. In some embodiments, the methods disclosed herein further comprise selecting subjects having regions of altered injected volume, ejected volume, residual volume, or combinations thereof, as being in need cardiac resynchronization therapy In some embodiments of all aspects, the subject is undergoing cardiac resynchronization therapy. In some embodiments, the methods disclosed herein comprise altering the cardiac resynchronization therapy protocol for subjects identified as having regions of altered injected, ejected and/or residual volumes.

In some embodiments of all aspects, the methods disclosed herein further comprise altering the atrio-ventricular (AV) delay, altering the ventriculo-ventricular (VV) delay, or altering the location of a pacemaker or pacemaker lead in subjects undergoing cardiac resynchronization therapy. In some embodiments, the methods disclosed herein further comprise measuring the flow properties of injected, ejected and/or residual volumes to optimize the cardiac resynchronization therapy.

In some embodiments of all aspects, generating numerical metrics of blood flow comprises calculating the kinetic energy of injected, ejected and residual volumes in the cardiac chambers.

In some embodiments of all aspects, generating numerical metrics of blood flow comprises calculating the linear momentum of injected, ejected and residual volumes in the cardiac chambers.

In some embodiments of all aspects, generating numerical metrics of blood flow comprises calculating the shape, location and/or size of injected, ejected and residual volumes in the cardiac chambers.

In some embodiments of all aspects, the methods described herein further comprise determining the atrioventricular delay that maximizes the linear momentum and/or kinetic transferred to the ejected fluid and/or the direct flow volumes.

In some aspects, the disclosure provides a fluid flow diagnostic system comprising a sensing unit configured to obtain a plurality of flow-velocity images of blood inside a cardiac chamber or blood vessel, and a processor configured to receive a plurality of flow-velocity images, calculate the blood flow velocity inside any cardiac chamber or blood vessel; and determine the location and extent of flow stasis in any cardiac chamber or blood vessel.

In some embodiments of all aspects, the processor is configured to receive a plurality of flow-velocity images (e.g., 2, 3, 4, 5, 6, 7, 8, 9, 10, or more flow-velocity images), calculate the blood flow's kinetic energy and/or rate of distortion and blood stasis timescale index inside the cardiac chamber or blood vessel; and determine the spatiotemporal distribution of the blood residence time, kinetic energy, and/or rate of distortion inside the cardiac chamber or blood vessel. In some embodiments, the processor is configured to receive a plurality of flow-velocity images performed with different velocity scales, as described herein.

In some embodiments of all aspects, the cardiac chamber is any cardiac chamber or blood vessel in which the blood velocity can be resolved. In some embodiments of all aspects, the sensing unit is a medical image-based apparatus able to determine blood flow velocity field.

In some aspects, the disclosure provides methods for calculating blood transport inside any cardiac chamber or blood vessel comprising obtaining flow-velocity images of blood inside a cardiac chamber, calculating the residence time ($T_R$), the standard deviation of the residence time ($\sigma_R$), kinetic energy, and/or rate of distortion of blood particles inside a cardiac chamber using the flow-velocity images to generate numerical metrics of blood flow, and generating a blood transport maps using numerical metrics to identify regions of decreased, increased, static or unaltered blood transit.

In some embodiments of all aspects, the numerical metrics of blood flow are used to delineate blood transit maps that identify the size and/or location of blood flow transport structures (e.g., direct flow (DF, blood that enters and exits the LV in the same cardiac cycle), retained inflow (RI, incoming blood that is not ejected during the same cycle), delayed ejection (DE, ejected blood that entered the LV in a previous cardiac cycle), or residual flow (RF, blood that entered the LV in a previous cycle and is not ejected in the current cycle, therefore residing in the LV for at least two cardiac cycles)) within the cardiac chamber or blood vessel. In some embodiments, in patients with LVADs, the numerical metrics of blood flow are additionally used to map the size and/or location of blood transport structures that transit from and/or into device flow elements such as inflow and/or outflow cannulas.

In some embodiments of all aspects, blood transit maps are used to identify the blood volumes that transit through a cardiac chamber or blood vessel during one beat.

In some embodiments of all aspects, generating numerical metrics of blood flow comprises calculating the momentum and orientation of the blood transit volumes.

In some embodiments of all aspects, the cardiac chamber is any cardiac chamber or blood vessel in which the blood velocity can be resolved. In some embodiments of all aspects, obtaining flow-velocity images of blood inside any cardiac chamber or blood vessel is performed using any medical image-based apparatus able to determine blood flow velocity field.

In some aspects, the disclosure provides methods for calculating blood transport inside any cardiac chamber or blood vessel comprising obtaining flow-velocity images of blood inside a cardiac chamber or blood vessel, calculating the residence time (TR), the standard deviation of the residence time ($\sigma_R$), kinetic energy, and/or linear momentum of blood particles inside a cardiac chamber using the flow-velocity images to generate numerical metrics of blood flow, and generating a blood transport maps using numerical metrics to identify different transit regions of blood.

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

This application contains at least one drawing executed in color. Copies of this patent or patent application publication with color drawing(s) will be provided by the Office upon request and payment of the necessary fee.

The data in each column are plotted as univariate scatter plots and summarized in the form of boxplots. In the patients, red and blue boxplots refer respectively CRTOFF and different AV delay cases. Each symbol type refers to a different patient, and is colored in green (red) if CRT makes the corresponding variable more (less) similar to the healthy subjects. The latter are represented by a green boxplot.

Figure 11:
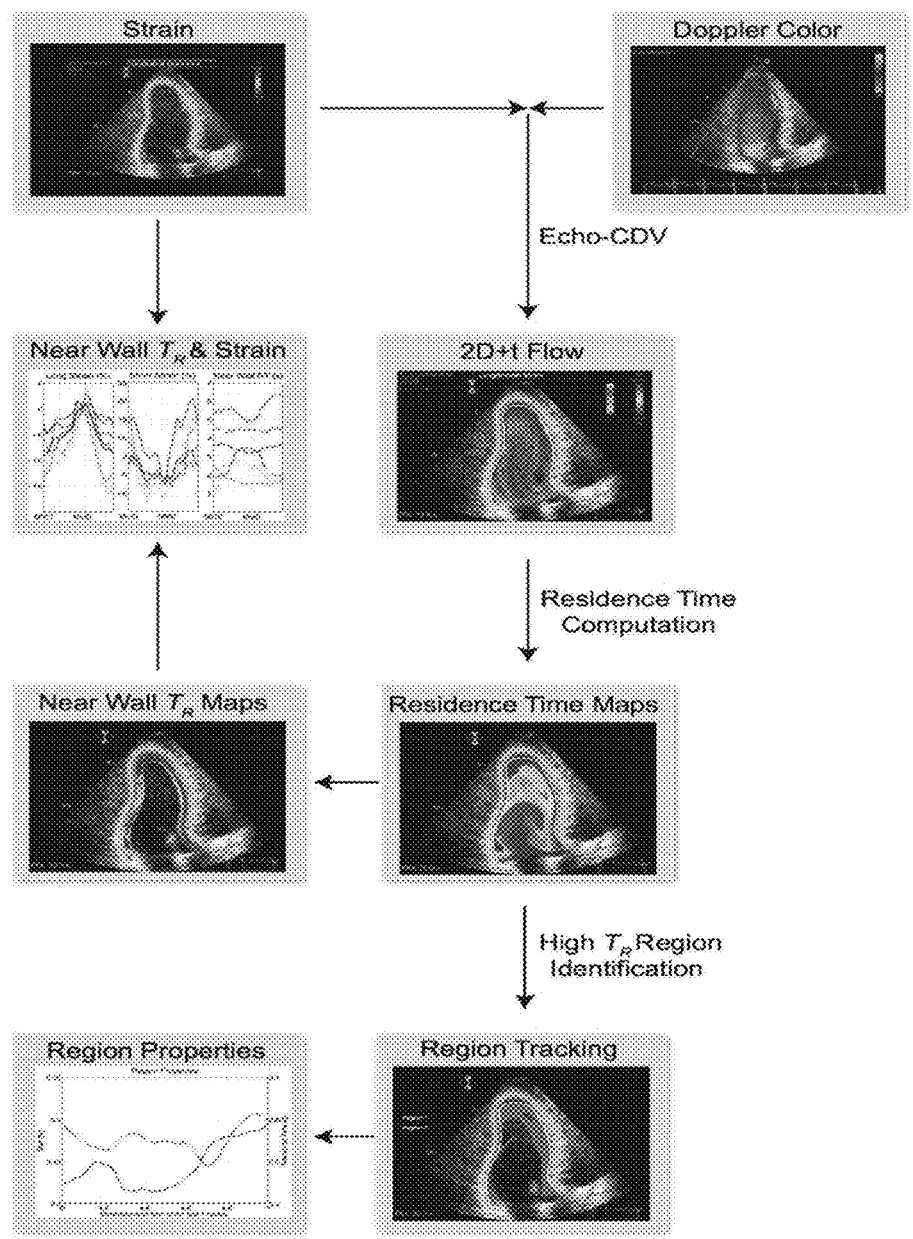

FIG. 11 is a flow-chart demonstrating an overview of the methods used for image acquisition and processing for the study described in Example 3. 2D+t: unsteady 2-dimensional. $T_R$: Residence Time.

Figure 12A:
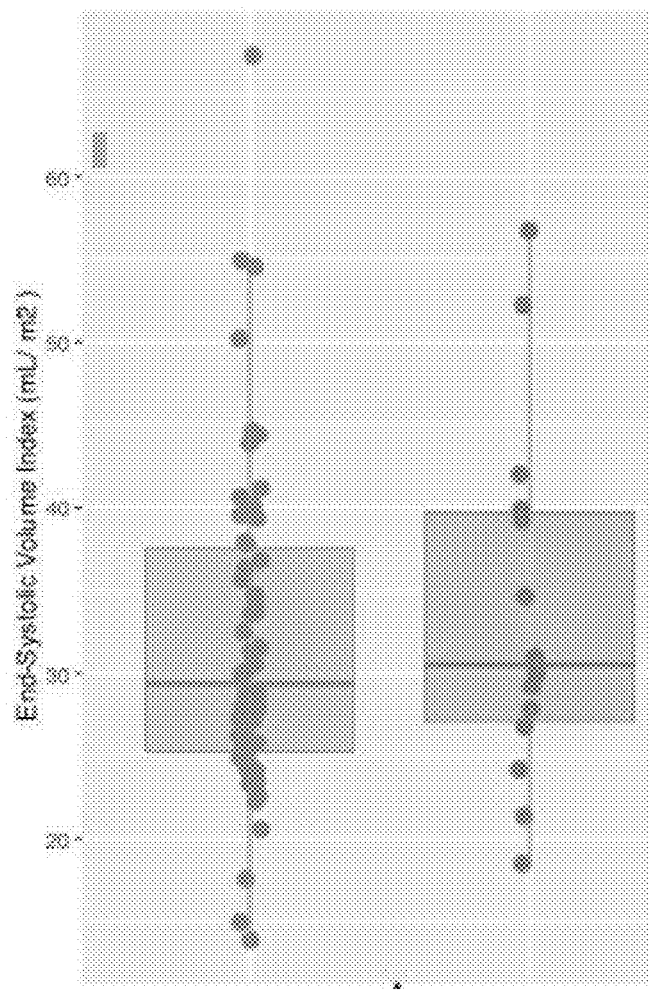
Figure 12B:
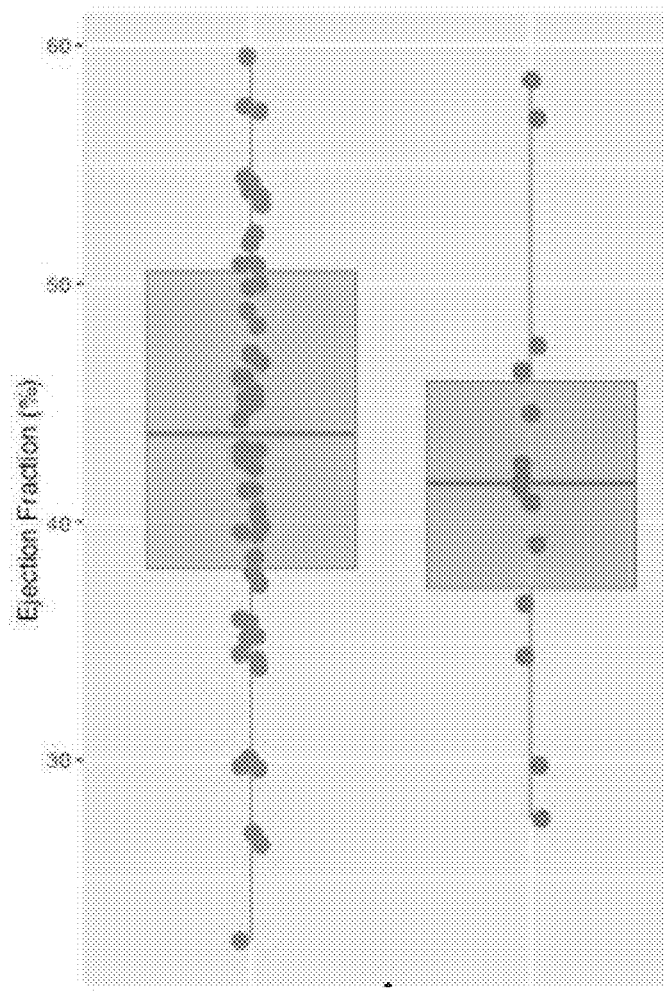
Figure 12C:
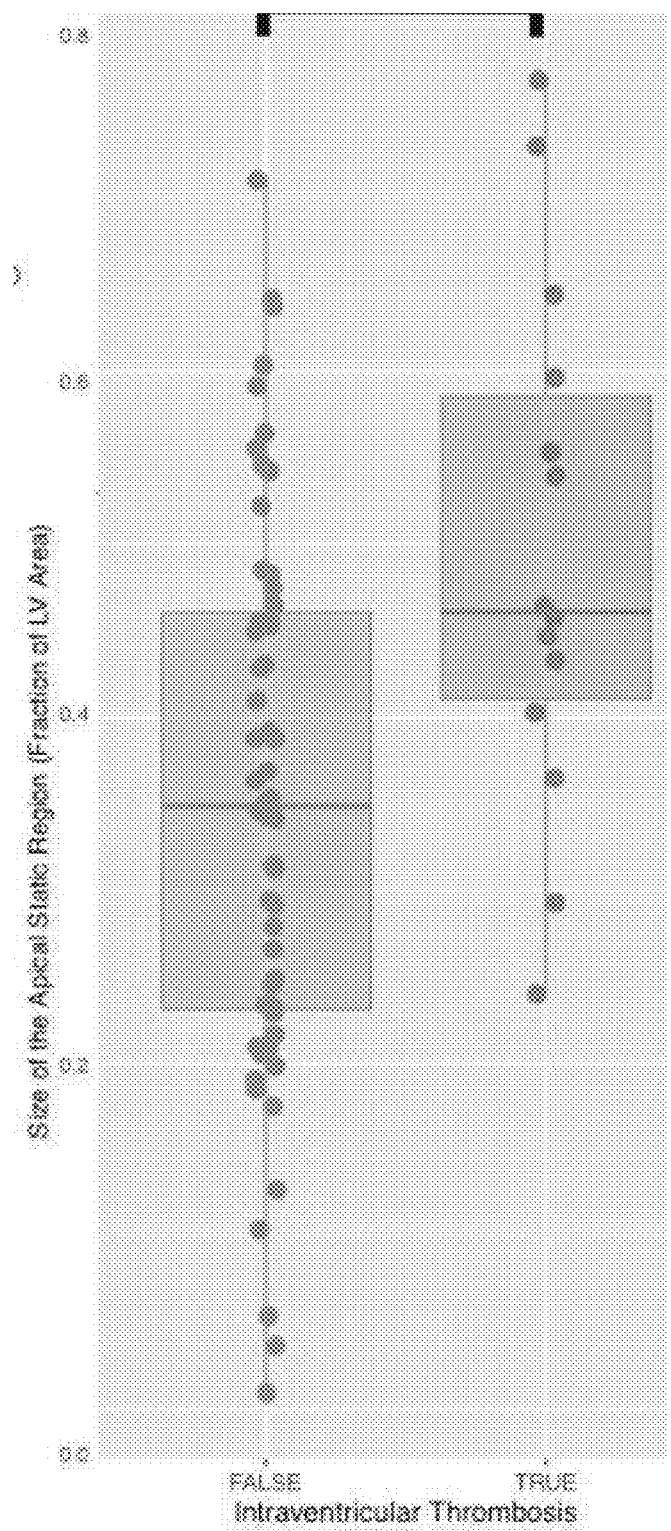
Figure 12D:
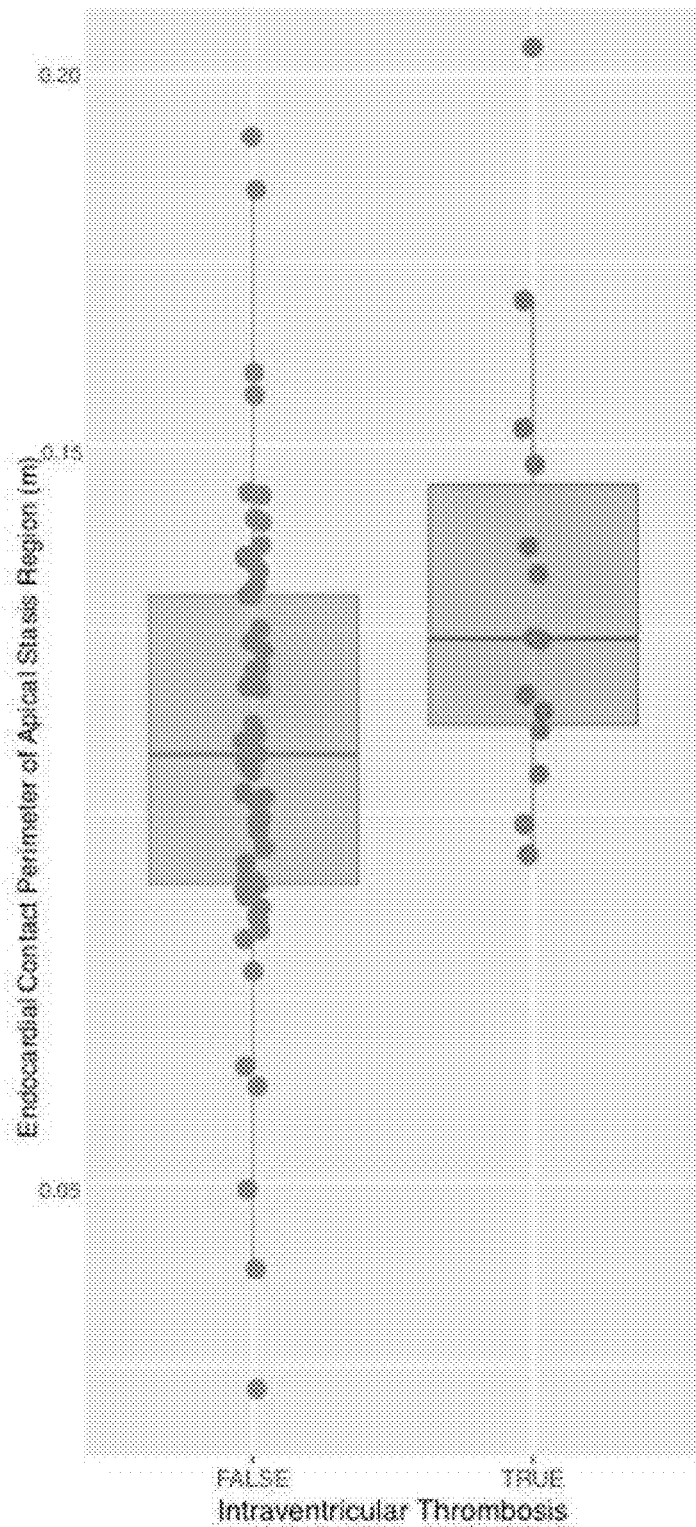

FIGS. 12A-D demonstrates boxplots of Conventional Echocardiographic parameters at enrollment for all patients with (blue) and without (red) LV thrombus. FIG. 12A: End Systolic Volume Index (ml/m2). FIG. 12B: Ejection Fraction (%). FIG. 12C: Size of the most apical blood region with Residence time>2 s (% of Area). FIG. 12D: endocardial contact length of the most apical blood region with Residence time>2 s (m).

DETAILED DESCRIPTION

In patients at risk of intraventricular thrombosis, the benefits of chronic anticoagulation therapy need to be balanced with the pro-hemorrhagic effects of therapy. Blood stasis in the cardiac chambers is a recognized risk factor for intracardiac thrombosis and potential cardiogenic embolic events.

The present disclosure is based, in part, on the discovery of novel flow image-based method to assess the location and extent of intraventricular stasis regions inside the a cardiac chamber or blood vessel by digital processing flow-velocity images obtained either by phase-contrast magnetic resonance (PCMR), 2D color-Doppler velocimetry (echo-CDV), echo-particle-image-velocimetry (echo-PIV), synthetic aperture ultrasound imaging, ultrasound vector velocimetry by transverse oscillation, direct PIV obtained by optical scanning of natural or artificial blood flow tracers. In general, any method suitable for providing a spatio-temporal distribution of flow velocity inside the cardiovascular system can be used. This approach is based on quantifying the distribution of the blood Residence Time ($T_R$) from time-resolved blood velocity fields in the cardiac chamber or blood vessel. In one aspect, the methods provided herein enable in-vivo assessment of the location and extent of the stasis regions in the LV cardiac chamber or blood vessel. Original metrics were developed to integrate flow properties into simple scalars suitable for a robust and personalized assessment of the risk of thrombosis. The early prediction of blood stasis in a cardiac chamber or blood vessel allows for directed use of anticoagulant or other (e.g., mechanical, surgical, or electrophysiologic) therapy for the purpose of primary and secondary prevention, which, ultimately, result in a decreased occurrence of strokes.

In some embodiments, methods disclosed herein comprise the prescription and dosing of anti-coagulant therapy to subjects identified as being at increased risk of intracardiac thrombus. Examples of such anticoagulant therapy include, but are not limited to, vitamin K antagonists, heparin and derivative substances, direct factor Xa inhibitors, and direct thrombin inhibitors.

In some embodiments, methods disclosed herein further comprise the administration of mechanical treatments to subjects identified as being at increased risk of intracardiac thrombus. Examples of such therapies include, but are not limited to, procedures and surgeries to remove or alter cardiac structures, or exclude blood flow from structures via intracardiac or extracardiac devices. Specific surgical examples include, but are not limited to, ventricular aneurysmectomy surgery and the AtriClip Gillinov-Cosgrove Left Atrial Appendage Exclusion system. Specific procedure examples include, but are not limited to, the Watchman Left Atrial Appendage Closure device and the LARIAT® Suture Delivery Device.

In some embodiments, methods disclosed herein further comprise administration of electrophysiologic treatments to subjects identified as being at increased risk of intracardiac thrombus. Examples of such therapies include, but are not limited to, procedures and/or surgeries to alter and/or ablate electrical heart rhythms and/or conduction patterns in the heart. In some embodiments, such procedures and/or surgeries can ablate atrial fibrillation.

The early prediction of blood stasis in a cardiac chamber or blood vessel may result in a decrease in strokes by appropriate use of anticoagulant therapy, appropriate use of mechanical surgical or procedural treatments to remove or alter cardiac structures or exclude blood flow from structures via intracardiac or extracardiac devices, or appropriate use of electrophysiologic surgical or procedural therapies to alter and/or ablate electrical heart rhythms and/or conduction patterns in the heart (including atrial fibrillation ablation) for the purpose of primary and secondary prevention. It may also have a significant impact on left ventricular assist device (LVAD) device design and operation set-up.

The methods disclosed herein rely on direct measurement of blood flow inside the cardiac chambers, instead of on numerical simulations of said flow, which are computationally expensive, and usually rely on geometrical oversimplifications about the heart's anatomy (e.g. valves, papillary muscles, trabeculae carnae, etc.), as well as oversimplified models of blood rheology. Furthermore, in some aspects, the methods provided herein are based on the solution of a transport equation to obtain the spatiotemporal distribution of residence time inside the cardiac chambers, which is much more efficient than releasing virtual particles and tracking their trajectories. The approach can be used to analyze cardiac imaging data obtained using standard modalities. These innovations make the disclosed method more reliable and better suited for 1) high-throughput clinical use and seamless integration within existing medical imaging devices and software tools, 2) evaluation of blood stasis in the four cardiac chambers rather than just in the left ventricle.

In some aspects, methods disclosed herein (e.g., methods for identifying regions of blood flow stasis inside a cardiac chamber or blood vessel of a subject, methods for estimating risk of intracardiac or intravascular thrombus or of embolism originating in a cardiac chamber or blood vessel in a subject, or methods for calculating blood transport inside any cardiac chamber or blood vessel) include identifying regions of blood flow stasis inside a cardiac chamber or blood vessel of a subject by obtaining flow-velocity images of blood inside a cardiac chamber or blood vessel of the subject, and calculating the residence time ($T_R$), the standard deviation of the residence time ($\sigma_R$), kinetic energy, and/or rate of distortion of blood particles. As used herein, a "blood particle" is defined as a fluid parcel of blood containing a very small amount of fluid that is identifiable throughout its dynamic history while moving with the blood flow.

In some embodiments of all aspects, generating numerical metrics of blood flow comprises calculating the blood flow's residence time ($T_R$) inside the cardiac chamber or blood vessel. In some embodiments of all aspects, generating numerical metrics of blood flow comprises calculating the standard deviation of the residence time ($\sigma_R$) inside the cardiac chamber or blood vessel. In some embodiments of all aspects, generating numerical metrics of blood flow comprises calculating both the blood flow's residence time ($T_R$) and the standard deviation of the residence time ($\sigma_R$) inside the cardiac chamber or blood vessel.

In some embodiments of all aspects, generating numerical metrics of blood flow comprises comparing the flow's residence time ($T_R$) versus its standard deviation ($\sigma_R$) inside the cardiac chamber or blood vessel. In some embodiments, in regions of a cardiac chamber or blood vessel where $T_R$ is high compared to $\sigma_R$, the identification and/or estimation of blood stasis is statistically more significant than in regions where $T_R$ is low compared to $\sigma_R$. In some embodiments, regions of a cardiac chamber or blood vessel where $T_R - \sigma_R$, or $T_R - 2\sigma_R$ and/or $T_R - 3\sigma_R$, etc. are higher than a reference value (e.g., the value of $T_R$ observed in a cohort of patients that developed a thrombus in a clinical study) are identified as regions of blood flow stasis. In some embodiments, regions of blood flow stasis are identified with a statistical significance of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or greater. In some embodiments, regions of blood flow stasis are identified with statistical significance of 84%, 97.8% or 99.9%. In some embodiments, regions of blood flow stasis that are identified with statistical significance are predictive of risk of intracardiac or intravascular thrombus or of embolism. In some embodiments, in regions of a cardiac chamber or blood vessel where the ratio of TR to $\sigma_R$ is higher than a reference ratio of TR to $\sigma_R$ (e.g., the ratio of $T_R$ to $\sigma_R$ observed in a cardiac chamber or blood vessel of a healthy subject), the identification and/or estimation of blood stasis is statistically more certain than where the ratio of $T_R$ to $\sigma_R$ is about the same or lower than the reference ratio of $T_R$ to $\sigma_R$. In some embodiments, regions of a cardiac chamber or blood vessel where the ratio of $T_R$ to $\sigma_R$ is high compared to a reference ratio (e.g., the ratio of $T_R$ to $\sigma_R$ observed in a cardiac chamber or blood vessel of a healthy subject) are identified as regions of blood flow stasis, and are predictive of risk of intracardiac or intravascular thrombus or of embolism.

In some embodiments of all aspects, generating numerical metrics of blood flow comprises calculating additional descriptors of the probability distribution of the values of the residence time (e.g., skewness, kurtosis, median, interquartile range and/or other inter-percentile ranges) at each point in space and instant in time, in order to estimate the statistical significance of the calculated values of $T_R$.

In some embodiments of all aspects, generating numerical metrics of blood flow comprises calculating the blood flow's kinetic energy inside the cardiac chamber or blood vessel. Kinetic energy measures the overall rate of motion of the blood particles inside a blood region. In some embodiments, low values of kinetic energy in a residual blood region (e.g., a blood region with high residence time) indicate that such region is stagnant and, therefore, prone to thrombosis. In some embodiments of all aspects, generating numerical metrics of blood flow comprises calculating the standard deviation of the blood flow's kinetic energy inside the cardiac chamber or blood vessel. In some embodiments of all aspects, generating numerical metrics of blood flow comprises calculating both the blood flow's kinetic energy and the standard deviation of the blood flow's kinetic energy inside the cardiac chamber or blood vessel. In some embodiments, a kinetic energy that is low compared to the standard of deviation of kinetic energy is indicative of blood flow stasis, and is predictive of risk of intracardiac or intravascular thrombus or of embolism.

In some embodiments of all aspects, generating numerical metrics of blood flow comprises calculating the blood flow's rate of distortion inside the cardiac chamber or blood vessel. The rate of distortion measures the rate at which the distances of adjacent blood particles change with time in the neighborhood of a given blood particle. In some embodiments, low values of rate of distortion in a residual blood region (e.g., a blood region with high residence time) indicate that such region is stagnant and, therefore, prone to thrombosis. In some embodiments of all aspects, generating numerical metrics of blood flow comprises calculating the standard deviation of the blood flow's rate of distortion inside the cardiac chamber or blood vessel. In some embodiments of all aspects, generating numerical metrics of blood flow comprises calculating both the blood flow's rate of distortion and the standard deviation of the blood flow's rate of distortion inside the cardiac chamber or blood vessel. In some embodiments, a rate of distortion that is low compared to the standard of deviation of the rate of distortion is indicative of blood flow stasis, and is predictive of risk of intracardiac or intravascular thrombus or of embolism.

In some embodiments of all aspects, generating numerical metrics of blood flow comprises calculating a blood stasis timescale index. As used herein, a "blood stasis timescale index" is an index that is inversely related to the rate of distortion, and that measures the amount of it that takes the flow to deform a given blood particle by an amount comparable to the size of the blood particle. In some embodiments, high values of a blood stasis timescale index in a residual blood region (e.g., a blood region with high residence time) indicate that such region is stagnant and, therefore, prone to thrombosis.

In some aspects, the methods disclosed herein utilize a spatiotemporal velocity map of blood flow in the heart as the input, together with anatomical images that are used to segment the walls of the cardiac chambers. This data may be obtained using color Doppler echocardiographic imaging, MRI with 4D flow, or other medical imaging techniques that provide velocity maps. The input data can consist of 2D or 3D time-resolved image data. The velocity data is used to solve a transport equation with unit forcing using the segmented wall positions to impose no penetration boundary conditions. This solver provides the spatiotemporal distribution of the blood residence time inside the cardiac chambers ($T_R$). The residence time distribution is analyzed using spatiotemporal clustering algorithms to identify residual regions with relative decreased mixing from incoming flow.

In some aspects, methods disclosed herein (e.g., methods for identifying regions of blood flow stasis inside a cardiac chamber or blood vessel of a subject, methods for estimating risk of intracardiac or intravascular thrombus or of embolism originating in a cardiac chamber or blood vessel in a subject, or methods for calculating blood transport inside any cardiac chamber or blood vessel) include generating a residence time ($T_R$) map, a kinetic energy map, and/or a rate of distortion map. In some embodiments, such maps are generated using numerical metrics of blood flow (e.g., numerical metrics of residence time ($T_R$), kinetic energy, and/or rate of distortion of blood particles obtained from one or more flow-velocity images) to identify and characterize regions of blood flow stasis.

In some embodiments of all aspects, methods disclosed herein include generating a map of the standard deviation of the residence time ($\sigma_R$), a map of the standard deviation of kinetic energy, and/or a map of the standard deviation of the rate of distortion. In some embodiments, such maps are generated using numerical metrics of blood flow (e.g., numerical metrics of the standard deviation of the residence time ($\sigma_R$), the standard deviation of kinetic energy, and/or the standard deviation of the rate of distortion of blood particles obtained from one or more flow-velocity images) to identify and characterize regions of blood flow stasis, particularly their statistical significance.

In some embodiments, a medical image-based apparatus is operated to obtain multiple flow-velocity images performed with different velocity scales (e.g., the encoding velocity in phase contrast MM or the color scale in Doppler echocardiography). In some embodiments, one or more flow-velocity images are performed with velocity scales that are significantly lower than the scales that are typically used (e.g., about 20 percent, about 25 percent, about 30 percent, about 35 percent, about 40 percent, about 45 percent, about 50 percent, about 55 percent, about 60 percent, about 65 percent, about 70 percent, about 75 percent, about 80 percent, or more lower than the scales that are typically used), in addition to one or more flow-velocity images that are performed with the typically-used velocity scales. In some embodiments, the data from the obtained multiple flow-velocity images are retrospectively merged in order to expand the dynamical range of the velocity measurements. In some embodiments, data from the obtained flow-velocity images are retrospectively merged to generate residence time ($T_R$), kinetic energy, and/or rate of distortion maps. In some embodiments, data from the obtained flow-velocity images are retrospectively merged to generate maps of standard deviation of residence time ($\sigma_R$), standard deviation of kinetic energy, and/or standard deviation of rate of distortion. Obtaining multiple flow-velocity images as described herein is useful in preventing overestimation of the residence time when there are regions where the blood velocity falls below the minimum measurable velocity of a single velocity scale acquisition (e.g., a velocity scale acquisition that is typically used). In some embodiments, the medical image-based apparatus is operated to obtain 2, 3, 4, 5, 6, 7, 8, 9, 10 or more flow-velocity images (e.g., one, two, or three-dimensional flow-velocity images resolved in time) performed with different velocity scales.

These residence time and flow velocity maps are then further processed to provide numerical metrics of blood stasis and the locations of regions with increased stasis. Specifically, the blood flow's kinetic energy, defined as $K=\frac{1}{2}(u^2+v^2+w^2)$, where u, v and w are the three components of the flow velocity in an orthogonal coordinate system, is determined. However, kinetic energy is not a Galilean invariant and it could be possible for a fluid parcel to have high values of K while moving with little distortion, similar to a rigid solid. Thus, the distortion of fluid particles, which is quantified by the second invariant of the symmetric strain tensor, $Q_{ij}=(du_i/dx_j+du_j/dx_i)/2$, is also computed. For an incompressible flow, the first invariant of $S_{ij}$ is zero and the second invariant is defined as $Q_S=\text{trace}(S_{ij}2)/2$. Note that $Q_S$ has dimensions of squared inverse of time, so it can be used to define a second stasis timescale $T_S=Q_S^{-1/2}$ in addition to $T_R$.

The size, position, shape, mobility, distance to cardiac wall, average kinetic energy and average distortion time of each spatio-temporally clustered residual volume are measured as a function of time. Colocalization and relative values of different metrics are also analyzed. Together with the number of residual volumes, this analysis provides a set of parameters that can be used to build a patient-specific risk index of blood stasis and risk of thrombus formation in the cardiac chambers based on non-invasive clinical images.

The present invention relates to methods useful for the characterization (e.g., clinical evaluation, diagnosis, classification, prediction, profiling) of a subject's risk of intracardiac thrombus formation and may benefit from treatment. As used herein, diagnosing includes both diagnosing and aiding in diagnosing. Thus, other diagnostic criteria may be evaluated in conjunction with the results of the methods in order to make a diagnosis.

The term "subject" refers to an animal or human. Preferably, the subject is a human. Subjects can also include non-human mammals. A human subject can be known as a patient.

In some embodiments, the patient is experiencing or known to have experienced in sinus rhythm with LV systolic dysfunction. Such patients are known to be at increased risk of thrombus formation and subsequent embolic events (e.g. stroke) but currently the vast majority of them are not being identified and treated with any anticoagulation therapy, resulting in a high degree of morbidity and mortality.

In some embodiments, the patient is experiencing or known to have experienced atrial fibrillation. Currently, such patients are risk-stratified based only on the basis of demographic and comorbidity data based on previous cohorts, but no patient-specific tools exist to optimally determine for which patients the risk/benefit of anticoagulation is favorable.

In some embodiments, the patient has an implanted left ventricular assist device (LVAD) and is at increased risk of thrombus formation. Thrombi in these patients can cause systemic emboli as well as LVAD dysfunction. The methods provided herein may be applied to these patients to determine: 1) pre-surgical optimization of device selection, 2) optimization of device implantation, 3) optimization of LVAD settings including, but not limited to, pump speed alteration, pump speed modulation, and the use of pump settings to generate intermittent pulsatile flow, and 4) identification of patients for whom the risk/benefit of anticoagulation therapy is favorable.

The disclosure further provides for the communication of results or diagnoses or both to technicians, physicians or patients, for example. In certain embodiments, computers will be used to communicate assay results or diagnoses or both to interested parties, e.g., physicians and their patients.

In some embodiments of the invention, a diagnosis is communicated to the subject as soon as possible after the diagnosis is obtained. The diagnosis may be communicated to the subject by the subject's treating physician. Alternatively, the diagnosis may be sent to a test subject by email or communicated to the subject by phone. The diagnosis may be sent to a test subject by in the form of a report. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications.

The terms "decrease", "decreased", "reduced", "reduction" or 'down-regulated" are all used herein generally to mean a decrease by a statistically significant amount. However, for avoidance of doubt, "reduced", "reduction", "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

EXAMPLES

The invention is further described in the following examples, which do not limit the scope of the invention described in the claims.

Example 1

Provided below are illustrative examples of normal hearts, patients with non-ischemic dilated cardiomyopathy and one patient before and after the implantation of an LVAD. The present study was designed to implement a novel method for measuring and mapping blood stasis in the heart. The purpose was to obtain individual quantitative metrics of global and regional stasis from flow-velocity measurements in the LV. The feasibility of the method was first tested in a high-resolution three-dimensional dataset of LV flow velocity obtained in a large animal by phase-contrast magnetic resonance (PCMRI). To generalize the applicability of the tool we also adapted the method to work with ultrasound data. We analyzed data from healthy and diseased LVs, as well as before and after LVAD implantation. We demonstrate the unique ability of the tool to identify and track the regions at risk of blood stagnation, providing qualitative and topological assessments of blood stasis in the LV Methods Study Population The present study is based on the following data: 1) high-resolution 3D PCMRI data from a pig scanned under highly controlled heart and respiratory rates, and 2) color-Doppler ultrasound datasets from 2 patients with non-ischemic dilated cardiomyopathy (NIDCM), one healthy volunteer without known heart disease and no cardiovascular risk factors, and one patient with end-stage HF both before and after LVAD implantation. Ultrasound datasets were randomly selected from a large database of two-dimensional velocity maps recruited at our institutions. The study protocol was approved by the local institutional review committee and all subjects provided written informed consent for this study. Clinical data are summarized in Table 1.

TABLE 1

| ID | Age | Gender | Regional Wall Motion | H.R. (b.p.m.) | EDV (mL) | ESV (mL) | EF (%) |
|---|---|---|---|---|---|---|---|
| HEALTHY | 51 | F | Normal | 64 | 98 | 31 | 68 |
| NIDCM-1 | 47 | M | Inferior & posterior akinesis | 80 | 81 | 62 | 24 |
| NIDCM-2 | 64 | F | Global hypokinesis | 76 | 154 | 117 | 24 |
| PRE-LVAD | 63 | F | Inferior & septal akinesis | 68 | 156 | 111 | 29 |
| POST-LVAD | 63 | F | LVAD | 100 | 84 | 63 | 25 |
| PIG | 1 | M | Normal | 76 | — | — | — |

H.R: Heart rate,
EDV: End-Diastolic Volume,
ESV: End-Systolic Volume,
EF: Ejection fraction,
HEALTHY: healthy volunteer;
NIDCM: non-ischemic dilated cardiomyopathy;
LVAD: left ventricle assist device.

3D PCMRI, Image Acquisition and Processing

A high-resolution 3D PCMRI of the LV together with its corresponding 3D anatomical images were obtained in a male Large White pig under anesthesia, using a 3T magnet (Achieva-Tx, Philips Medical Systems, Best, the Netherlands), equipped with a 32-channel cardiac phased-array surface coil. Images were acquired during spontaneous ventilation using retrospective electrocardiographic gating. 3D PCMRI images were planned in a standard 4 and 2-chamber view to cover the entire LV from the level of the mitral annulus to the apex. The following imaging parameters were used: FOV 240×240 mm, voxel size 2×2×4 mm, 1 NEX, SENSE 2, reconstructed heart phases 25 corresponding to a time resolution of 34 ms, PC flow directions RL-AP-FH, act. TR/TE (ms)=6.0/3.7 and VENC of 100 cm/s, as similarly reported (Garcia-Alvarez et al 2013). The velocity field inside the ventricle was obtained from the phase data after correcting for phase-aliasing artifacts through phase unwrapping of closed regions with abnormal intensity gradient. Each anatomical image was post processed using a semi-automatic volume segmentation tool in order to obtain the ventricle boundary surface throughout the cardiac cycle. The segmentation method is based on a multi-resolution level-set active contour optimized for heart segmentation (Gonzalez et al 2015).

2D Image Acquisition, Analysis and Processing

Comprehensive 2-dimensional (2D) B-mode and color-Doppler echocardiographic examinations were performed using a Vivid 7 scanner and 2-4 MHz transducers (General Electric Healthcare). The LV myocardial wall was segmented, and its longitudinal and transversal strain were measured from the apical long-axis B-mode sequences to delineate the endocardial boundary (EchoPac v.110.1.2, General Electric Healthcare). We reconstructed the 2D+t flow field inside the LV using 2D echo color Doppler velocimetry (echo-CDV), as previously described and validated in vitro (Garcia et al 2010) and in vivo (Bermejo et al 2014). The 2D flow velocity fields together with the LV segmentation were used to integrate the unit-forced transport equation and to calculate the spatiotemporal evolution of blood residence time inside the LV (see below). Conventional Doppler-echocardiographic data was recorded following current recommendations (Lang et al 2015).

Residence Time

The time spent by a blood particle inside the LV can be evaluated by a scalar magnitude known as Residence Time ($T_R$). Using a Lagrangian approach, $T_R$ evolution can be described by the advection equation with unit forcing, $$\partial_t T_R + \nabla \cdot (\vec{v}_{inc} T_R) = 1, \quad (1)$$

where $\vec{v}_{inc}$ is the velocity field. Previous works have considered a similar equation with a non-zero mass diffusivity term (Esmaily-Moghadam et al 2013, Jozsa & Kramer 2000, Mangual et al 2012), but we note that the self-diffusivity of blood is negligible compared to its advective fluxes inside the LV (Bermejo et al 2015, Tarbell 2003). We provide the first rigourous derivation of equation using statistical mechanics (1). In the absence of a diffusive term, equation (1) can be completed with Dirichlet boundary conditions at the inlet, $S_{in}$, when the blood coming from the left atrium enters the cardiac domain $V_{刑}$. Equation (1) was numerically integrated on a Cartesian grid using a second-order Finite Volume discretization, in which $T_R$ and $\vec{v}_{inc}$ were respectively interpolated at each cell's center and faces. We used a Total Variation Diminishing (TVD) flux limiting scheme (LeVeque 2002) to avoid the numerical oscillations that would appear at the sharp interfaces created by the transport process, particularly between fresh blood entering the LV each cycle and the residual blood from previous cycles. A second-order time integration scheme was adopted keeping the Courant-Friedrichs-Lewy (CFL) number below 0.5 throughout the whole integration and using a variable time step, $\Delta t$ bounded between 5-0.3 ms for the 2D-echo-CDV and 33-0.5 ms for the 3D PCMRI data. The velocity field at each integration step was obtained by linearly interpolating in time the previous and the successive velocity acquisition data frames.

Spatio-temporally connected pixels with high residence time (e.g. $T_R > 2$ sec) were clustered and stored for further analysis using in-house algorithms. Clusters smaller than 2% LV volume (area in 2D) and clusters that did not span the whole cardiac cycle were discarded and were not analyzed further.

PCMRI Velocity Regularization for Mass Conservation

Similar to other flow measurement techniques, PCMRI provides velocity fields with noise that usually do not satisfy mass conservation (i.e. $\vec{v}_{inc} \neq 0$). Although noise can be minimized by appropriate fine-tuning during data acquisition, appreciable errors remain in current state-of-the-art PCMRI measurements (Busch et al 2013). Errors in mass conservation are particularly troublesome for the purpose of analyzing blood transport and residence time because they introduce a spurious source term equals to $-T_R \nabla \cdot \vec{v}_{inc}$ in the transport equation (1). This spurious term can generate undesired variations in $T_R$ that are not caused by convective blood transport. In this work, we apply a solenoidal projection method to enforce the condition that the PCMRI velocity field is incompressible (Chorin 1967). Note that, since the echo-CDV fields are derived by enforcing mass conservation (Garcia et al 2010), they automatically satisfy this condition. Briefly, a velocity field derived from a potential function φ is added to the original field, $\vec{v}_0: \vec{v}_{inc} = \vec{v}_0 + \nabla \varphi$. Imposing that $\vec{v}_{inc}$ is divergence-free allows for calculating φ by solving a Poisson's equation with non-homogeneous Neumann boundary conditions at the LV walls. This problem was solved using a custom Multi-Grid method developed in FORTRAN, interpolating the original domain onto a Cartesian grid. The moving boundary was defined independently of the Cartesian grid by using a sharp interface immersed boundary method (Mittal et al 2008).

Grid Sensitivity Analysis

While time-resolved 3D PCMRI provides invaluable information about the multi-dimensional flow transport and stasis patterns in the LV, the moderate spatiotemporal resolution ($\Delta x = \Delta y = 0.94$ mm, $\Delta z = 2$ mm & $\Delta t = 33$ ms) of this technique could pose a potential limitation. To rule out this possibility, we performed a sensitivity analysis of the dependence of the $T_R$ maps on the time and space resolution in the echo-CDV data, which is better resolved ($\Delta x = 0.5$ mm & $\Delta t = 5$ ms). We progressively deteriorated the resolution of N=3 echo-CDV datasets and computed the average L2 norm of the error in the $T_R$ fields as a function of $\Delta x$ and $\Delta t$. Table 2 summarizes the results of this analysis, and suggests that the resolution of the PCRMI data used in this work was sufficient to accurately resolve the spatiotemporal evolution of the residence time.

Derivation of Partial Differential Equations for the Residence Time, the Standard Deviation of the Residence Time, and the Probability Density Function of the Residence Time.

In this section, we derive the continuum equation for the residence time of a fluid to parcel based on the stochastic analysis of the residence time of its constituent particles. The stochastic derivation is done in 1D without loss of generality.

We consider a fluid particle with position, x, which varies as the particle moves with local flow velocity, v, and due to Brownian fluctuations. The Langevin equations for the particle's position and residence time, T, are $$\frac{dx}{dt} = v + 2\sqrt{k}\,\xi(t), \quad (2)$$

$$\frac{dT}{dt} = 1, \quad (3)$$

where ξ(t) is a random forcing with a Dirac delta correlation function, and k is the diffusivity of the fluid particle within the rest of the fluid (Gardiner 2004). From these equations, it is straightforward to derive the Fokker-Planck equation for the probability density function, p(x,T,t), $$\frac{\partial p}{\partial t} = -\frac{\partial (vp)}{\partial x} - \frac{\partial p}{\partial T} + \frac{\partial}{\partial x}\left(k\frac{\partial p}{\partial x}\right). \quad (4)$$

Notice that the relevant coefficient in equation (4) is diffusivity and not the viscosity, as at a microstructural level mass diffusion between two instants of time requires change of position while momentum diffusion requires particle collision, which can occur without change of position. The diffusivity coefficient k can arise from the natural microstructural agitation of the fluid and its multiphasic components (e.g., red blood cells, platelets and plasma) and/or it can be an artificial diffusivity that models the stochastic stirring caused by the random noise in the measurement of the velocity field. To obtain an equation for the continuum residence time, one can multiply by T equation (4), yielding

TABLE 2

|  |  | dt [ms] | | | | |
|---|---|---|---|---|---|---|
|  | Number of input frames | 3.9 ± 0.4<br>200 | 7.8 ± 0.7<br>100 | 15.7 ± 1.5<br>50 | 39.2 ± 3.8<br>20 | 78 ± 7.5<br>10 |
| Nx × Ny, dx [mm] | 256 × 256, 0.35 ± 0.02 | Reference: $\tilde{T}_R$ | 0.022 ± 0.015 | 0.121 ± 0.02 | 0.15 ± 0.039 | 0.297 ± 0.104 |
|  | 128 × 128, 0.70 ± 0.04 | 0.123 ± 0.018 | 0.124 ± 0.018 | 0.154 ± 0.02 | 0.173 ± 0.029 | 0.28 ± 0.092 |
|  | 64 × 64, 1.42 ± 0.08 | 0.212 ± 0.027 | 0.21 ± 0.028 | 0.218 ± 0.03 | 0.227 ± 0.024 | 0.282 ± 0.075 |
|  | 32 × 32, 2.88 ± 0.16 | 0.295 ± 0.028 | 0.293 ± 0.029 | 0.293 ± 0.029 | 0.296 ± 0.028 | 0.32 ± 0.049 |
|  | 16 × 16, 5.96 ± 0.32 | 0.394 ± 0.035 | 0.395 ± 0.036 | 0.401 ± 0.041 | 0.406 ± 0.055 | 0.396 ± 0.035 |

Sensitivity analysis over 6 beats (6T): mean±standard deviation, of the L2 norm of the error, defined below, compared to the reference frame in 3 different cases.

$$\|err\|_2 = \sqrt{\int_{t=0}^{t=6T}\int_{\Omega}(\tilde{T}_R - T_R)^2 dxdydt / \int_{t=0}^{t=6T}\int_{\Omega}\tilde{T}_R^2 dxdydt}$$

$$\frac{\partial (Tp)}{\partial t} = -\frac{\partial (Tvp)}{\partial x} - T\frac{\partial p}{\partial T} + \frac{\partial}{\partial x}\left(k\frac{\partial (Tp)}{\partial x}\right). \quad (5)$$

This equation can be integrated in T between ±infinity to obtain a governing equation for the ensemble average of T, $$T_R(x,t)=\int_{-\infty}^{\infty} Tp(x,T,t)dT, \quad (6)$$

which is the residence time of the fluid parcel at each position and instant of time. The only non-trivial term when integrating eq. (5) is $$\int_{-\infty}^{\infty} T\frac{\partial p}{\partial T}dT. \quad (7)$$

Equation (7) can be handled by parts resulting in $$\int_{-\infty}^{\infty} T\frac{\partial p}{\partial T}dT = Tp\Big|_{-\infty}^{\infty} - \int_{-\infty}^{\infty} p\,dT = -1. \quad (8)$$

It is straightforward to see that the first term in the right-hand-side of equation (8) needs to be zero if p is integrable, and that the integral of p must be equal to 1 since p is a probability density function. Thus, combining equations (5), (6) and (8), one arrives at:

$$\frac{\partial(T_R)}{\partial t} = -\frac{\partial(vT_R)}{\partial x} - (-1) + \frac{\partial}{\partial x}\left(k\frac{\partial T_R}{\partial x}\right). \quad (9)$$

The natural mass diffusivity of blood is customarily considered much smaller than its kinematic viscosity, and it is not expected to play an important role in influencing particle trajectories, platelet-surface contact frequency and dissociative binding phenomena under flow at physiological shear rates (Fournier 2012, Leonard et al 1972, Mody & King 2007, Peattie 2013). Therefore, if we set k=0, which is analogous to previous studies of LV blood transport based on the deterministic integration of fluid particle trajectories (Hendabadi et al 2013, Wigstrom et al 1999), equation (9) becomes $$\frac{\partial T_R}{\partial t} + \nabla \cdot (T_R \vec{v}) = 1 \quad (10)$$

which is the 1D analogous of equation (1).

Similarly, we can obtain an evolution equation for the standard deviation of $T_R$, which is to useful to estimate the uncertainty in the measurement of residence time. In this case, we multiply by $T^2$ equation (4), which yields $$\frac{\partial(T^2 p)}{\partial t} = -\frac{\partial(T^2 vp)}{\partial x} - T^2\frac{\partial p}{\partial T} + \frac{\partial}{\partial x}\left(k\frac{\partial(T^2 p)}{\partial x}\right). \quad (11)$$

We integrate this equation in T between −∞ and ∞ similar to what was done to derive eq. (9), obtaining $$\frac{\partial(S_R)}{\partial t} + \frac{\partial(vS_R)}{\partial x} = 2T_R + \frac{\partial}{\partial x}\left(k\frac{\partial S_R}{\partial x}\right).$$

where $$S_R(x,t) = \int_{-\infty}^{\infty} T^2 p(x,T,t)dT,$$

is the second-order moment of the residence time of the fluid parcel at each position and instant of time. Solving for $S_R$ and $T_R$ allows us to determine the standard deviation of the residence time as $$\sigma_R(x,t) = \sqrt{S_R(x,t) - T_R^2(x,t)}$$

To determine the evolution of the whole probability density function of T, rather than just its average or standard deviation, we can integrate equation (4) directly, with a Dirac Delta centered at T=0 (whole probability distribution concentrated at T=0) as initial and inlet boundary condition.

Discussion

Residence Time in 3D

Figure 1:
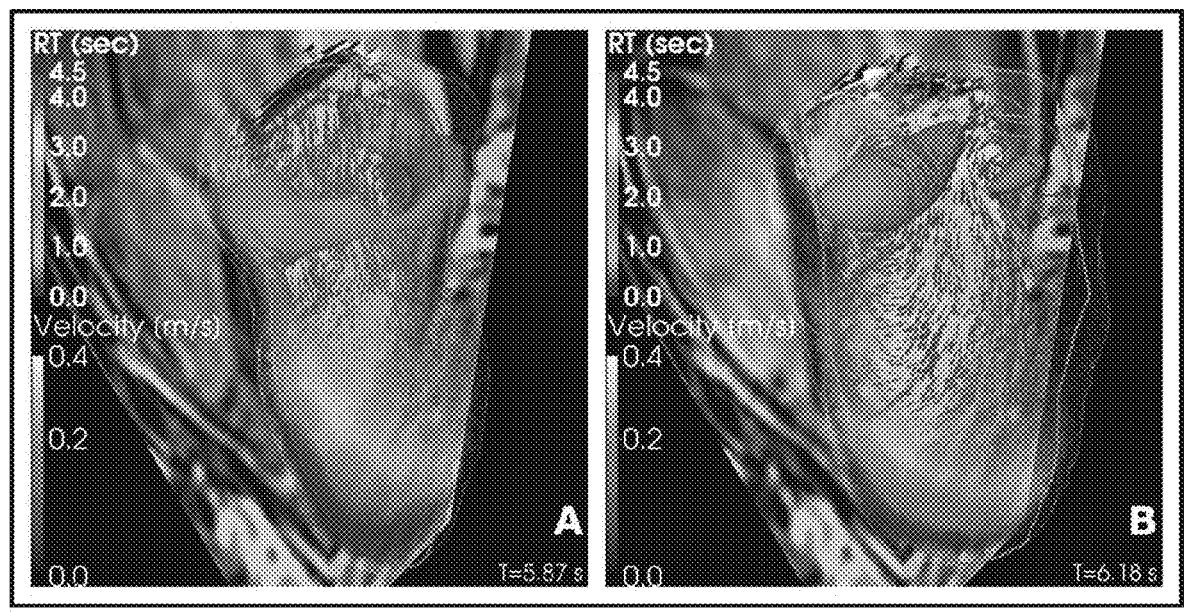
FIG. 1 displays 3D renderings of velocity fields and residence time maps in a pig at mitral valve opening (panel A) and at the end of filling (panel B). Wireframe contour depicts the LV volume segmentation. The magenta and contour lines identify the long-axis plane that contains the mitral valve, apex and aortic valve. The vortical structures in purple are visualized by isosurfaces of $\lambda_{ci}$ (imaginary part of the complex conjugate eigenvalue of $\nabla v$).

The 3D+t spatiotemporal distribution of TR in the LV was calculated from PCMRI data. FIG. 1 displays 3D renderings of TR at mitral valve opening and at isovolumic contraction. The velocity field shows the strong diastolic jet and associated vortex ring that characterizes LV filling flow (Bermejo et al 2015). In this ventricle the region of highest TR is located close to the apex, and extends towards the aortic tract along the anteroseptal wall. This residence time pattern agrees well with the pattern observed in normal human LVs (see example in FIG. 2, panel A). The three-dimensionality of the TR field is evident in FIG. 1, and is caused by the complexity of intraventricular blood flow and transport during the cardiac cycle. However, the main features of this field are well captured in the three-chamber view (delineated by the magenta contour in FIG. 1), particularly the maximum value of TR and its apical location. This result is important because our approach to estimate TR using conventional echocardiography is performed from velocity fields acquired in the three-chamber view.

LV Residence Time in Non-Ischemic Dilated Cardiomyopathy

Dilated cardiomyopathy is a condition associated with increased risk of intraventricular thrombosis. The normal LV flow pattern has been reported to recycle the blood volume inside the left ventricle every 2-3 beats (FIG. 2, panel A) (Bolger et al 2007, Eriksson et al 2010, Hendabadi et al 2013, Watanabe et al 2008). However, blood transport is significantly altered in patients with NIDCM by the large swirling flow patterns that are typical of this condition (FIG. 2, panels B & C) (Bermejo et al 2014, Hendabadi et al 2013). In these patients, blood is trapped inside long-lasting vortices and undergoes rotation throughout most of the cardiac cycle. Blood trapped in these vortices has high residence time but is not stagnant. Thus, proper assessment of intraventricular stasis should consider factors such as the distortion of fluid particles and their kinetic energy density in addition to $T_R$. The kinetic energy density of a fluid particle, defined as $K=(u^2+v^2)/2$, can be used together with $T_R$ as an intuitive indicator of stasis. However, kinetic energy is not a Galilean invariant and it could be possible for a fluid parcel to have high values of K while moving with little distortion, similar to a rigid solid. The distortion of a fluid particle can be quantified by the second invariant of the symmetric strain tensor $S_{ij}=(\partial_{x_j} u_i + \partial_{x_i} u_j)/2$. For an incompressible flow, the first invariant of $S_{ij}$ is zero and the second invariant is defined as $Q_s = \text{trace}(S_{ij}^2)/2$. Note that $Q_S$ has dimensions of squared inverse of time, so it can be used to define a second stasis timescale $T_s = Q_s^{-1/2}$ in addition to $T_R$.

Figure 2:
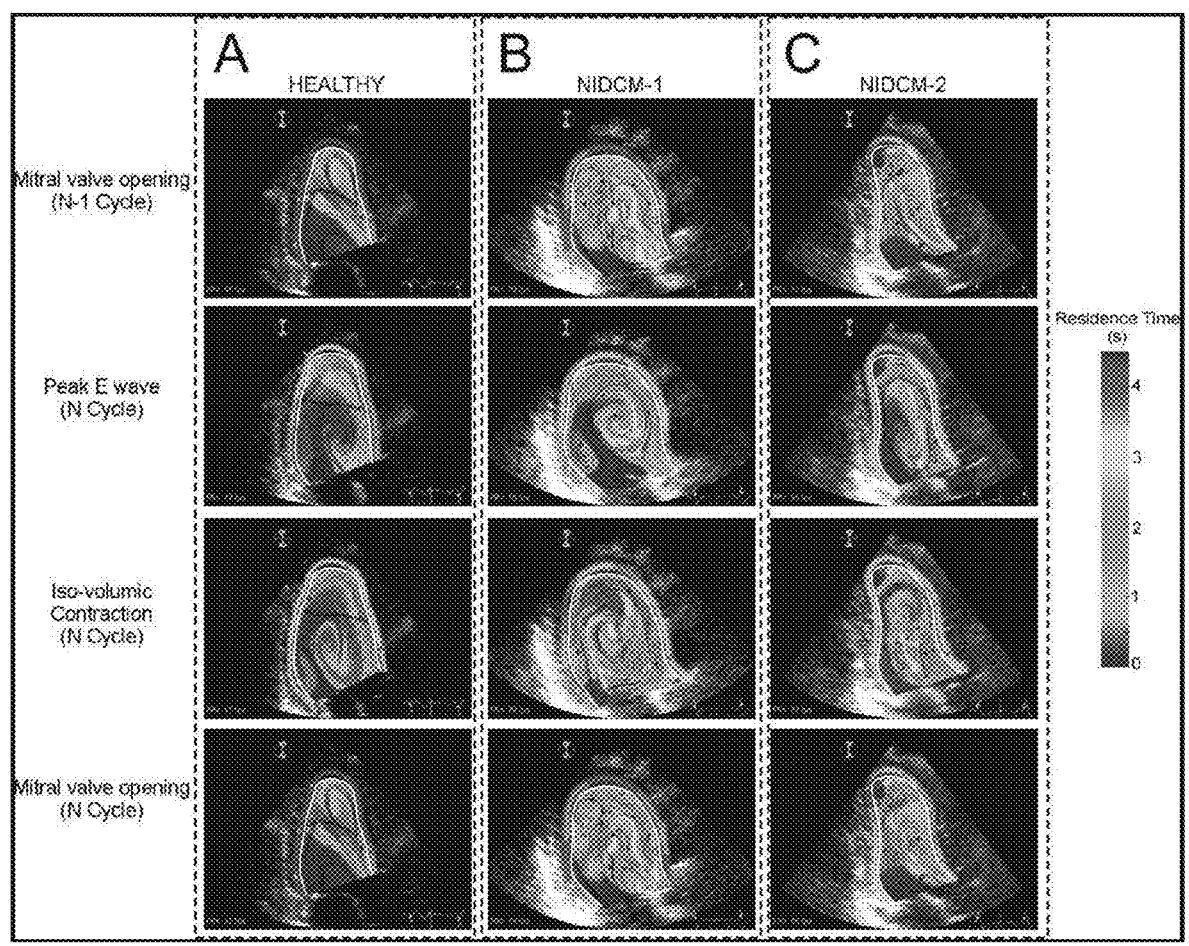
FIG. 2 displays snapshots of 2-D intraventricular residence time along the cardiac cycle in a healthy heart (panel A) and in two different examples of non-ischemic dilated cardiomyopathy (NIDCM) patients (panels B & C). 1st row: Residence Time mapping at the mitral valve opening in the converged N−1 cycle. 2nd row: Residence Time mapping at peak E-wave in the last computed cycle. 3rd row: Residence Time mapping at the iso-volumetric contraction in the last computed cycle. 4th row: Residence Time mapping at mitral valve opening in the last cycle. Notice that in both NIDCMs there coexist different regions with high $T_r$.
Figure 3:
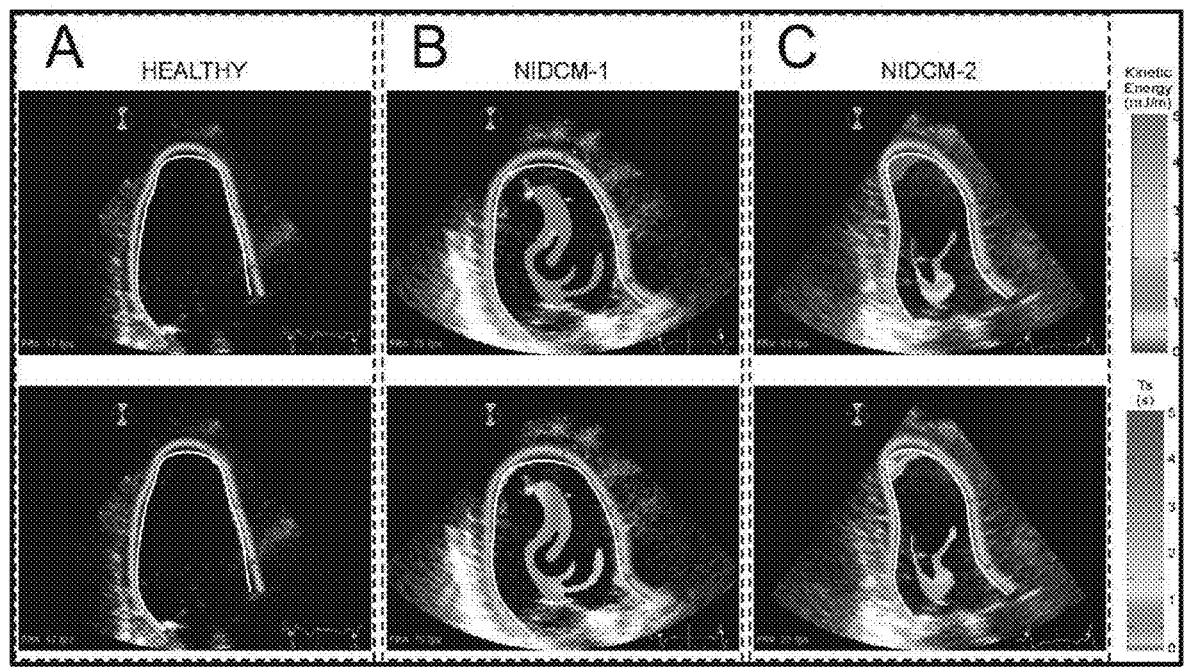
FIG. 3 displays snapshots of 2-D K and $T_S$ before mitral valve opening in the last converged cardiac cycle in a healthy heart (A) and in two different examples of NIDCM (B & C). $1^{st}$ row: Kinetic energy density (K) mapping in the regions with in the regions with $T_R > 2$ s. $2^{nd}$ row: Distortion time ($T_S$) in the regions with $T_R > 2$ s. The NIDCM-2 case is at risk of apical blood stasis given the combination of low K and large $T_S$.

FIG. 3 shows the spatial distributions of K and $T_S$ in the regions with $T_R$>2 s for the same ventricles of FIG. 2, at the end of diastole. As expected, the normal LV (FIG. 3, panel A) does not show any significant region with $T_R$>2 s. There is a small cluster located near the endocardium but it has relatively high K and low $T_S$. Interestingly, both dilated LVs (FIG. 3, panels B & C) show large regions with $T_R>2$ s located at the center of the chamber but these regions are associated with high values of K and low values of $T_S$. This indicates that blood is continuously being stirred by the LV flow patterns in this centrally located region despite having high $T_R$. By contrast, the second diseased LV (FIG. 3, panel C) shows a separate, apically located region with $T_R>2$ sec that also has low K and high $T_S$, and is therefore stagnant. These results illustrate how the combined analysis of the spatiotemporal Lagrangian patterns of residence time and Eulerian measures of fluid motion and distortion can provide clinically accessible information about intraventricular blood stasis from conventional color-Doppler datasets.

Changes in Blood Stasis After LVAD Implantation

Implantable cardiac assist devices, particularly LVADs, are considered to alter the physiological blood flow patterns in the heart, leading to increased risk of thrombosis (Bluestein 2004, Wong et al 2014). Among the three elements of Virchov's triad, abnormal flow patterns present the most complex challenge to improve device design and post-implantation patient management (Kormos 2015). However, blood stasis has not been previously measured in the patients implanted with LVADs.

Figure 4:
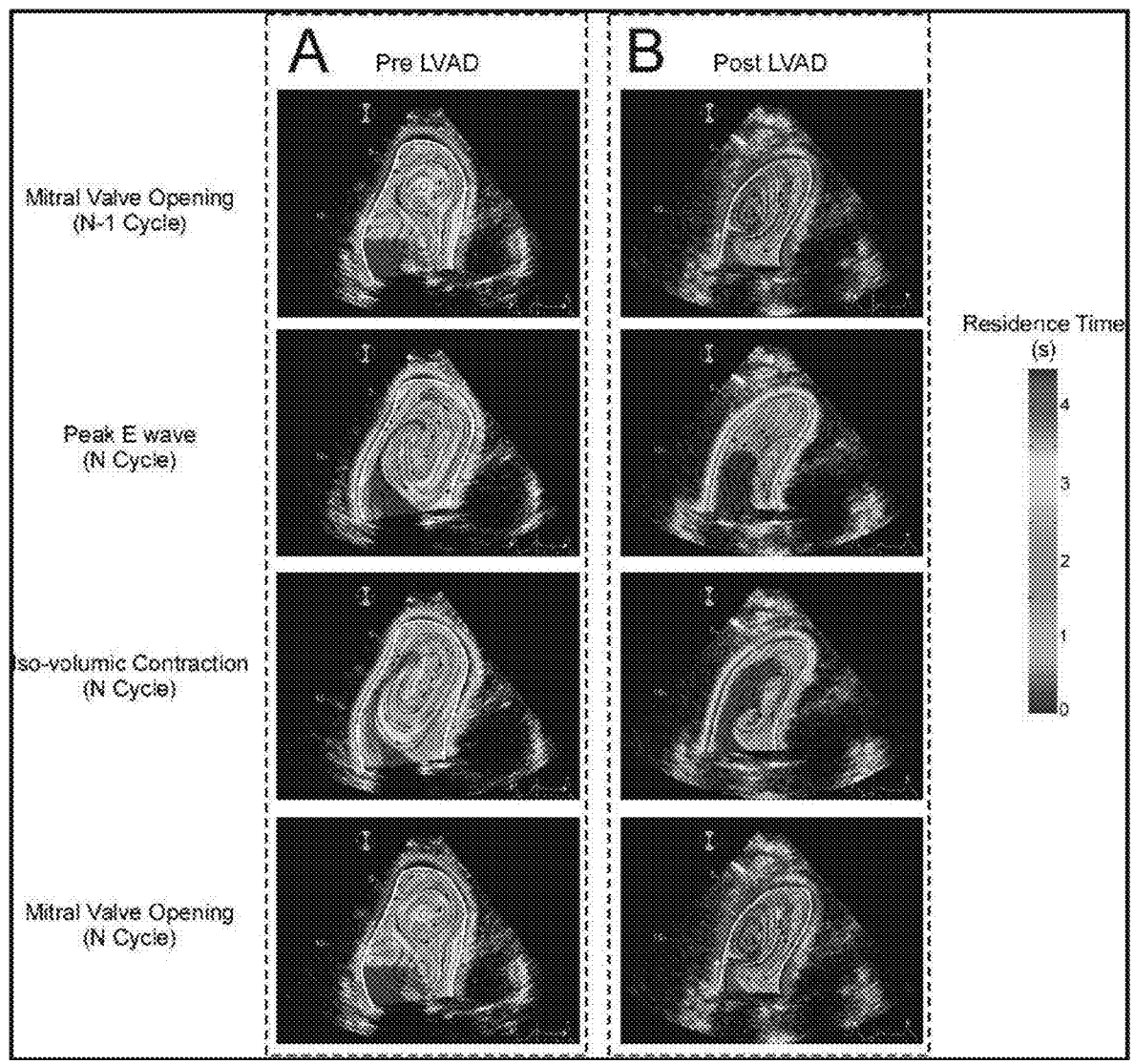
FIG. 4 displays snapshots of 2-D intraventricular residence time along the cardiac cycle in a patient before (panel A) and after (panel B) LVAD implantation. The apically located inflow LVAD cannula is represented in magenta. 1st row A: Residence Time mapping at the mitral valve opening in the converged N−1 cycle. 2nd row: Residence Time mapping at E-wave peak in the last computed cycle. 3rd row: Residence Time mapping at the onset of isovolumic contraction in the last computed cycle. 4th row: Residence Time mapping at mitral valve opening in the last cycle.

FIG. 4 shows residence time maps along a cardiac cycle in a patient with NIDCM, mitral regurgitation and end-stage HF before and 1 month after LVAD implantation. The pre-LVAD condition (FIG. 4 panel A) shows a large region with $T_R>2$ s located at the center of the chamber, which is caused by the large swirling region that is sustained during most of the cardiac cycle in this dilated heart. This large swirling pattern is indicated by the circular instantaneous streamlines in FIG. 4, panel A. Consistent with the results presented in FIG. 3, this region is associated with relatively high values of kinetic energy density and low values of $T_S$, implying that this region is not stagnant. However, this flow and stasis pattern are significantly altered after LVAD implantation, as the flow is channeled from the mitral annulus to the LVAD inflow cannula located at the LV apex, instead of transiting towards the outflow tract (magenta line in FIG. 4, panel B). As a result, a region with high residence time, moderate low kinetic energy and moderate low fluid distortion (moderately high $T_S$) appears near the LV outflow tract. These factors combined are the hallmark of blood stasis, suggesting a hemodynamic explanation for clinical reports of mural thrombosis in the LV outflow tract of LVAD-implanted patients (May-Newman et al 2013). These in vivo results are in agreement with previous in vitro experiments performed using a cardiac simulator (Wong et al 2014), although it should be noted that the drastic LV volume unloading caused by LVAD implantation was not modeled in the in vitro study.

Simplified Residence Time Indices

Figure 5:
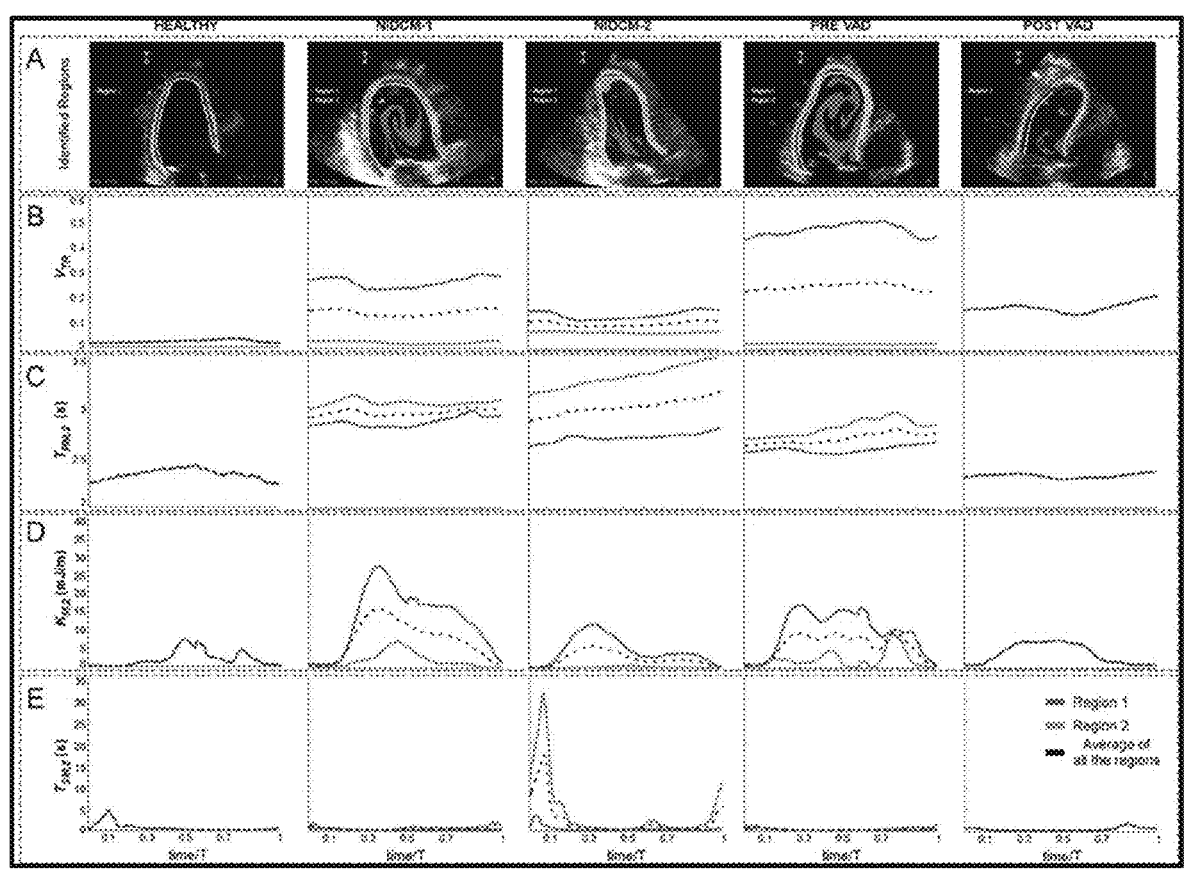
FIG. 5 displays examples of region tracking (row A) and time evolution of $V_{TR}$ (row B), $T_{M,2}$ (row C), $K_{M,2}$ (row D), $T_{SM,2}$ (row E) along the last converged cycle in all the 2-D studied cases: Healthy heart (1st col), NIDCM-1 (2nd col), NIDCM-2 (3rd col), Pre-VAD (4th col) and Post-VAD (5th col). Line colors correspond to each of the tracked regions (row A) and their average (black).

An additional challenge in introducing clinically relevant indices of LV blood stasis is to incorporate metrics that integrate the spatiotemporal nature of the $T_R$ distributions, together with additional parameters such as K or $T_S$, into simple metrics that can be used to compare values between patients. Therefore, we identified Lagrangian clusters of residual volume formed by spatiotemporally connected pixels with $T_R>2$ sec (FIG. 5, A), and plotted the following indices as a function of time for each Lagrangian cluster: 1) Relative LV volume (area in 2D) occupied by each cluster ($V_{TR}$, FIG. 5, B), 2) spatially-averaged value of $T_R$ in each cluster ($T_{RM,2}$, FIG. 5, C), 3) spatially-averaged value of K in each cluster ($K_{M,2}$, FIG. 5, D), and 4) spatially-averaged value of $T_S$ in each cluster ($T_{SM,2}$, FIG. 5, E).

The temporal profiles of $V_{TR}$ varied periodically, implying that the numerical integration of eq. 1 achieved numerical convergence. Consistent with the instantaneous maps in FIG. 2, the diseased hearts showed higher values of $V_{TR}$ than the healthy volunteer throughout the cardiac cycle. Remarkably, in the NIDCM cases, the profiles of $T_{RM,2}$ increased from beat to beat, indicating that there is a persistent residual volume of blood that does not mix with incoming blood in these ventricles. Conversely, $T_{RM,2}$ varied periodically for the healthy case, suggesting that blood is not indefinitely trapped in healthy ventricles. Separate analysis of each $T_R>2$ s Lagrangian cluster for diseased LVs showed that the apically located residual volume in NIDCM case 2 had significantly higher values of $T_{SM,2}$ and significantly lower values of $K_{M,2}$ than all other residual volumes in NIDCM cases 1 and 2. These data suggest that it is possible to derive simplified indices of stasis from the Doppler-derived spatiotemporal maps of $T_R$, $T_S$ and K. Furthermore, our results indicate that individual analyses of intracavitary residual volumes help to unmask blood stasis in patients with more than one residual volume region.

To further simplify the potential clinical application of these stasis indices, we considered temporally averaging the time-varying indices defined above for each Lagrangian cluster of residual volume. The time-averaged indices are denoted with an overline (e.g. $\overline{V_{TR}}$) and are summarized in Table 3 for the subjects analyzed in this pilot study. To facilitate the identification of each cluster, its normalized average apical location, $\overline{X_A}$, is included in the table (0 indicates basal and 1 indicates apical). Despite the small number of cases, we found marked differences in time-averaged stasis indices in patients with NIDCM and healthy volunteers, as well as in the patient with HF before and after LVAD implantation. The values of $\overline{V_{TR}}$ in the diseased LVs ranged between 20% and 50%, much higher than the healthy case which had less than 2.5%. The secular variation of $T_{RM,2}$ in the diseased cases rendered $\overline{T_{RM,2}}$ meaningless in those cases. Conversely, the values of $\overline{K_{M,2}}$ and $\overline{T_{SM,2}}$ were not relevant in the healthy case and for the secondary residual volumes of cases NIDCM 1, NIDCM2 and the pre-LVAD case, which had insignificant size. Consistent with the results presented in the previous sections, the apical residual volume of NIDCM case 2 had an appreciable size ($\overline{V_{TR}} \approx 7\%$), its value of $\overline{K_{M,2}}$ was considerably low and its value of $\overline{T_{SM,2}}$ was considerably high. Likewise, in the LVAD patient, $\overline{V_{TR}}$, $\overline{K_{M,2}}$, and $\overline{T_{SM,2}}$ reflect the increase of blood stasis risk near the outflow tract after LVAD implantation. These results suggest that the time-averaged stasis indices were able to capture the subtle differences in the spatiotemporal stasis patterns found in those two ventricles.

TABLE 3

| CASE | # Residual volumes ($T_R > 2$ s clusters) | Cluster | $\overline{V_{TR}}$ (nor.) | $\overline{T_{RM,2}}$ (sec) | $\overline{T_{SM,2}}$ (sec) | $\overline{K_{M,2}}$ (mJ/m$^3$) | $\overline{X_A}$ (nor.) | $\overline{V_{TR0}}$ (nor.) | $\overline{T_{RM,20}}$ (s) | $\overline{T_{SM,20}}$ (s) | $\overline{K_{M,20}}$ (mJ/m$^3$) |
|---|---|---|---|---|---|---|---|---|---|---|---|
| HEALTHY | 1 | 1 | 0.023 | 2.33 | 0.64 | 2.0 | 0.92 | | | | |
| NIDCM-1 | 2 | 1 | 0.26 | secular | 0.25 | 13.4 | 0.43 | 0.14 | Secular | 0.34 | 7.74 |
| | | 2 | 0.025 | secular | 0.43 | 2.1 | 0.85 | | | | |
| NIDCM-2 | 2 | 1 | 0.14 | secular | 0.48 | 4.8 | 0.28 | 0.10 | Secular | 2.36 | 2.49 |
| | | 2 | 0.068 | secular | 4.3 | 0.19 | 0.86 | | | | |
| PRE-VAD | 2 | 1 | 0.47 | secular | 0.28 | 10.0 | 0.51 | 0.25 | secular | 0.47 | 4.03 |
| | | 2 | 0.023 | secular | 0.66 | 2.2 | 0.40 | | | | |
| POST-VAD | 1 | 1 | 0.17 | secular | 0.45 | 4.0 | 0.32 | | | | |

HEALTHY: healthy volunteer;
NIDCM: non-ischemic dilated cardiomyopathy;
LVAD: left ventricle assist device.

$\overline{V_{TR}}$:
Normalized fraction of chamber volume (Area in 2D) occupied by blood with $T_R > 2$ s, averaged over the cardiac cycle.

$\overline{T_{RM,2}}$:
Mean residence time in the region with $T_R > 2$ s, averaged over the cardiac cycle.

$\overline{T_{SM,2}}$:
Mean distortion time scale in the region with $T_R > 2$ sec, averaged over the cardiac cycle.

$\overline{K_{M,2}}$:
Mean kinetic energy density in the region with $T_R > 2$ s, averaged over the cardiac cycle.

$\overline{X_A}$:
Normalized average cluster apical location.
Subindex 0 denotes the average of all the regions with $T_R > 2$ s.

The examples provided above demonstrate implementation of an in vivo method to generate multi-dimensional spatiotemporal maps of LV blood stasis. The inventors also derive simplified patient-specific stasis metrics that integrate these maps and can be used to guide personalized clinical decision-making. This new method is based on the quantification of the residence time spent by blood particles inside a cardiac chamber since entering the chamber, which is obtained by integrating a transport equation with unit forcing. A residence time threshold can be used to automatically segment and label residual blood volumes that do not mix with the fresh blood entering a cardiac chamber each cardiac cycle, and which are potentially stagnant. By analyzing the kinetic energy and the rate of distortion of each one of these residual volumes the methods disclosed herein discern whether blood is stagnant inside a cardiac chamber. This semi-Lagrangian categorization has been shown to anticipate thrombogenic regions in a pilot study in patients with acute myocardial infarction (Devesa et al 2015).

To illustrate the residence time mapping methodology, the inventors assessed intraventricular blood stasis in several representative LV examples. The healthy LV presented residual volumes of small size in comparison to NIDCM patients. Conversely, the inventors observed large residual volumes inside the persistent swirling flow patterns that develop in dilated LVs (Bermejo et al 2014). These results are concordant with previous studies based on echo-CDV and PCMRI (Bolger et al 2007, Eriksson et al 2010, Eriksson et al 2011, Hendabadi et al 2013).

Further analysis of the fluid's kinetic energy and rate of distortion suggests that, although the blood inside these residual volumes barely mixes with fresh blood entering the LV each cardiac cycle, it is continuously stirred by the surrounding fluid. Therefore, it was concluded that the large swirling flow pattern that develops in dilated LVs does not necessarily induce blood stasis. In addition to this frequent pattern, some diseased LVs had other regions of high residence time that were also associated with low kinetic energy and low rates of distortion, and which were effectively stagnant. Thus, the present invention allows clinicians to assess the degree of intraventricular blood stasis on an individualized basis.

By combining echo-CDV and residence time mapping, we obtained the first quantification of intraventricular blood stasis in patients with LVADs. The results provided above suggest that intraventricular blood stasis in the LVAD-assisted heart can be higher than prior to implanting the device, particularly near the left ventricular outflow tract, a region reported to be thrombogenic during continuous LVAD support (May-Newman et al 2013). Mapping methods as the one proposed herein show an excellent potential to correlate stagnant regions with local and global wall motion abnormalities. This type of analysis may be useful in optimally choosing the insertion sites for the LVAD cannulas on a per patient basis.

The methods disclosed herein relies on clinical access to time-resolved intracavitary velocity fields but is independent of the imaging modality employed to measure intraventricular velocity. In this work, the inventors exploited this flexibility to obtain $T_R$ maps from both 3D+t PCMRI and 2D+t echo-CDV velocity fields. This allowed use of each modality to evaluate the limitations of the other, namely the spatiotemporal resolution in PCMRI and the planar flow simplification in echo-CDV. The analysis of residence time maps derived from 3D+t PCMRI showed that both the key spatial features and numerical values of $T_R$ are well represented in the long-axis three-chamber plane imaged by 2D echo-CDV. The inventors performed a sensitivity analysis on echo-CVD data with progressively coarsened spatial and temporal resolutions, concluding that the resolution of the PCRMI velocity fields used in this work was adequate to accurately quantify intraventricular blood stasis. However, this method may be sensitive to low-scale velocities.

Currently, blood stasis inside the cardiac chamber is not assessed in the clinical setting. Echo-CDV has important practical advantages, as it is fast, clinically feasible, does not require infusion of contrast agents, and it can be safely performed in patients implanted with LVADs. A limitation of this approach is that it neglects the effect on mixing of intraventricular anatomical elements such as papillary muscles and endocardial trabeculae, which can locally increase mixing (Bermejo et al 2015). This may be particularly important at the endocardial surface, where our approach predicts high residence time values. This limitation could be addressed by including a mass-diffusivity term in eq. (1) with a spatially varying coefficient that would need to be determined from high-resolution anatomical imaging. Additionally, there is no doubt that the planar flow simplification may lead to inaccuracies in the estimation of LV blood transport. However, the impact of these and other technical issues needs to be balanced against the potential clinical benefit offered by the new method. In this context, a pilot study suggests that echo-CDV-derived indices of blood stasis may be able to predict LV thrombus formation in patients with acute myocardial infarction (Devesa et al 2015), a condition in which an individualized assessment of the risk of thrombosis is particularly necessary.

In summary, the inventors have developed a method to quantify and map intraventricular stasis from flow-velocity measurements which is suitable for bedside clinical application. Using this method, important physiological consequences of a number of cardiovascular procedures can now be addressed. Interventions such as valve replacement, resynchronization therapy, correction or palliation of congenital cardiac defects, and surgical ventricular restoration are all known to heavily disturb physiological flow dynamics.

Example 2

Dyssynchrony is associated with a higher risk of both worsened failure and sudden cardiac death [3]. In addition to intraventricular conduction abnormalities, patients with dyssynchrony also frequently have associated impaired conduction from the atria to the ventricles. Atrioventricular (AV) dyssynchrony further impairs the ability of the failing heart to pump blood, worsening the severity of HF [4-8].

Cardiac resynchronization therapy (CRT) is a well-established non-pharmacological treatment for congestive HF. CRT recovers the physiological activation pathways, improving cardiac function and clinical outcomes in patients who associate HF and dyssynchrony. When applied to adequately selected patient populations, CRT has a positive impact on symptoms, quality of life and mortality [9,10]. This therapy is used to restore coordinated pumping of the ventricles by using a specialized cardiac pacemaker. Unfortunately, between 25% and 30% of patients receiving CRT do not show the expected benefits. It has been suggested that achieving a favorable CRT response may in part depend on proper device programming [11-13]. Therefore, optimization of the AV delay has been shown to improve cardiac output and may be necessary in up to 55% of CRT patients during follow-up [14-16]. However, the best method to optimize the AV delay is still controversial [17,18].

Nature has optimized the coupling of molecular, electrical and mechanical processes of the heart, leading to flow patterns that minimize energy losses and facilitate the smooth redirection of incoming blood towards the outflow tract [19-22]. The interaction between wall mechanics and intracavitary flow establishes fluid transport barriers, which separate the blood that transits from inflow directly to outflow each cardiac cycle from the blood that is retained inside the LV [22-26]. Lagrangian particle tracking using time-resolved 3D phase-contrast MRI velocity fields [27] and analysis of Lagrangian coherent structures (LCS) have been instrumental to quantify these transport barriers [28, 22]. However, these methods are based on expensive calculations of the trajectories of virtual fluid particles, and are difficult to automate for high-throughput analysis in the clinical setting.

Preliminary studies have shown that the main intraventricular flow pattern, a vortex ring that forms during diastole, is highly sensitive to the timing intervals of the cardiac cycle and to tachycardia [29]. Shortening the filling period by programming long electrical AV delays increases the circulation and kinetic energy of the vortex and results in the vortex staying closer to the mitral valve [28]. When compared to baseline conduction, biventricular stimulation seems to improve organization of intraventricular flow, suggesting that intraventricular flow analysis is a useful tool to understand the effects of resynchronization on heart mechanics [30]. Remarkably, changes in electrical activation have been shown to modify the net orientation of the forces acting on blood inside the LV, which has been associated with improved long-term outcome in patients undergoing CRT [31]. These findings suggest that flow imaging may be a suitable tool for optimizing this therapy. However, how CRT settings affect the specific time evolution of the different flow volumes and the LV filling waves is still poorly understood.

The present study was designed with the twofold purpose of 1) implementing a clinically feasible high-throughput method for measuring and mapping blood transport in the heart, and 2) testing its clinical potential to characterize changes in blood transport caused by CRT. The general approach was to obtain individual quantitative metrics of flow transport from flow-velocity measurements in the LV.

Methods

Study Population

Figure 7:
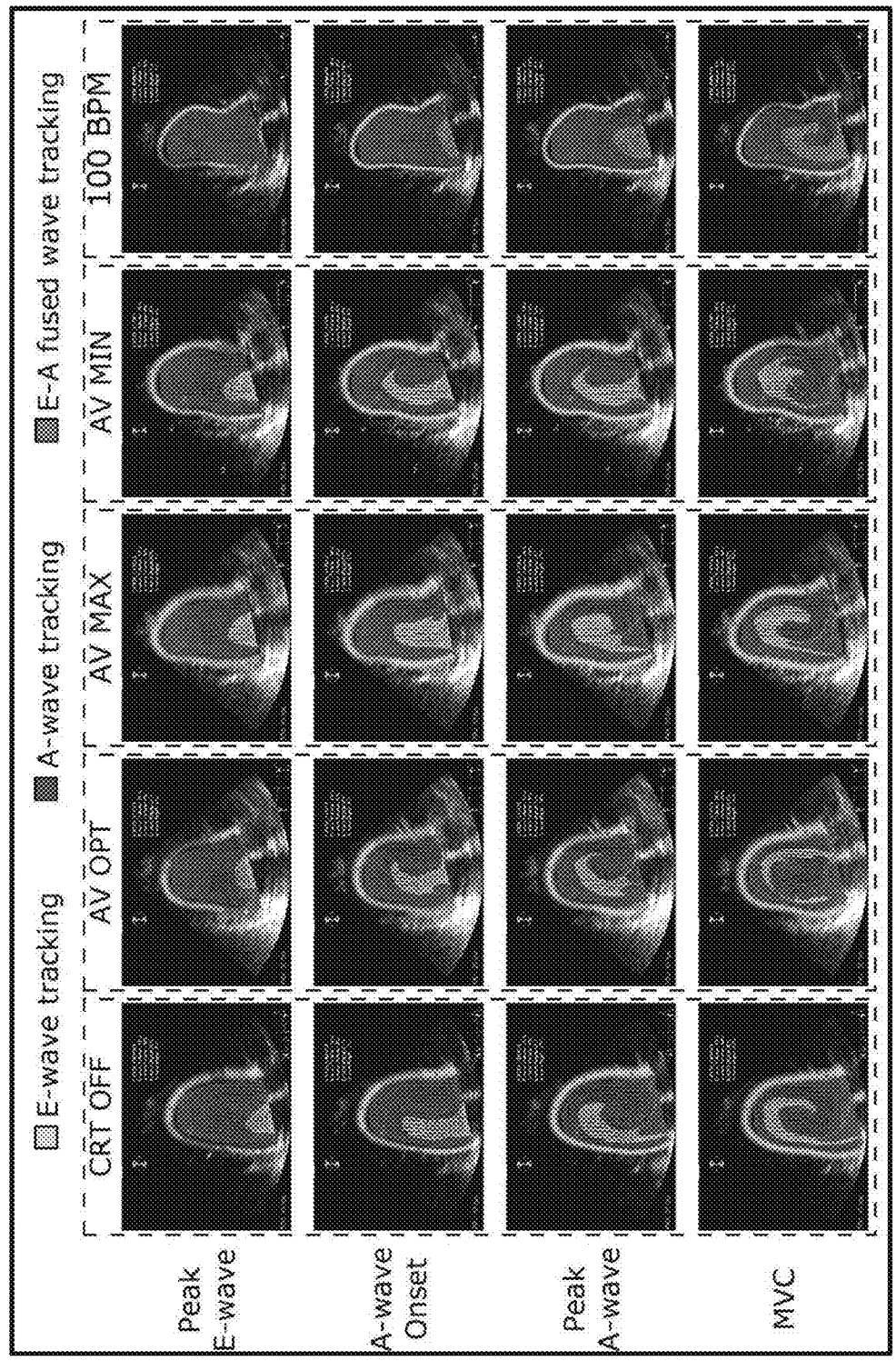
FIG. 7 demonstrates evolution of filling transport regions in the LV of the same patient shown in FIGS. 1-2. Each column represents a different CRT setting: A) CRT-OFF, B) AVOPT, C) AVMAX, D) AVMIN and E) Tachycardia (100 bpm). Each row represents a different instant during diastole: the $1^{st}$, $2^{nd}$, $3^{rd}$ and $4^{th}$ rows correspond respectively to peak E wave, A-wave onset, peak A wave and MVC. In each panel, the yellow and red regions track respectively the fluid that enters the LV during the E wave and the A wave, whereas the blue background tracks the residual volume of blood that occupies the LV at the onset of diastole. Instantaneous velocity vectors are shown in black. In the Tachycardia setting the E/A-waves fusion is depicted in green.
Figure 8:
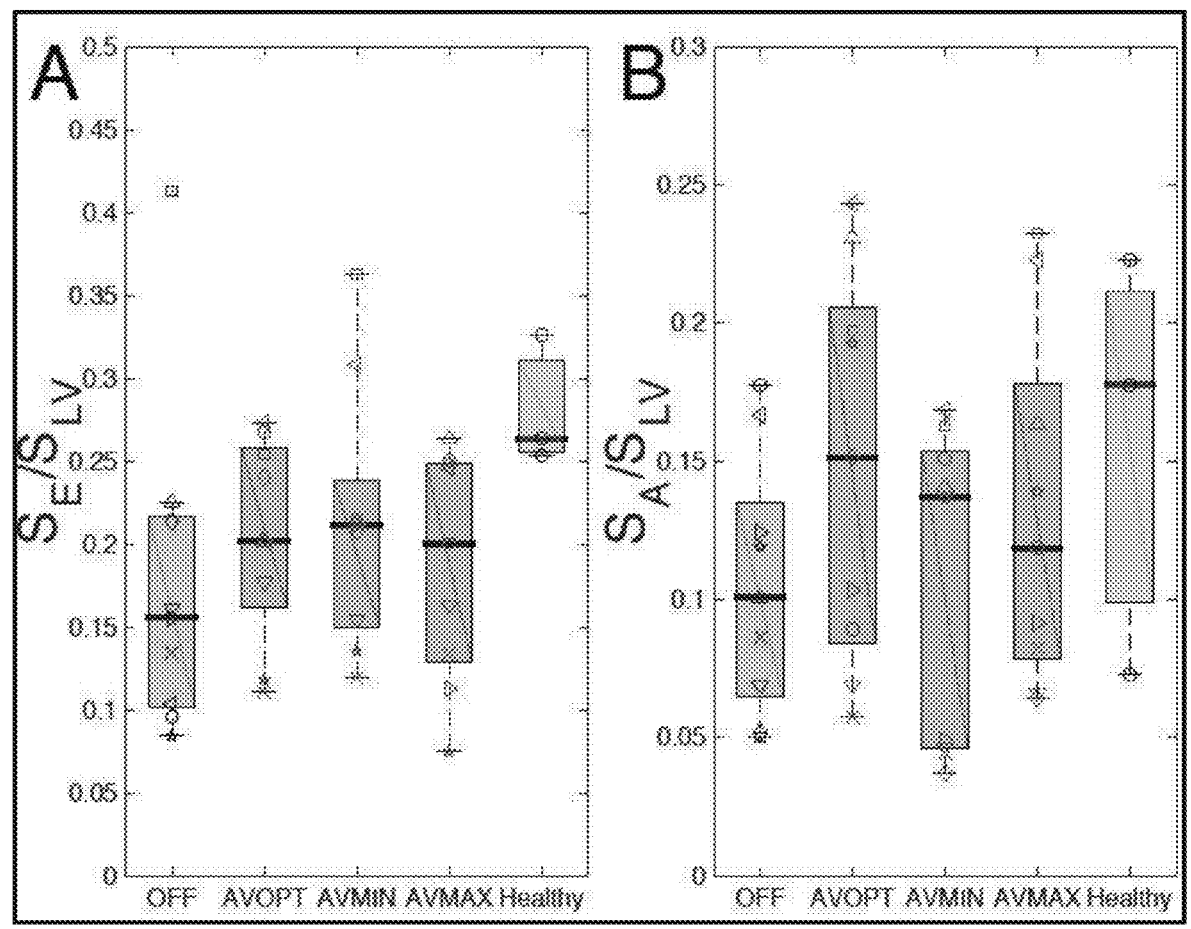
FIG. 8 demonstrates % LV volume occupied by E-wave (panel A) and A-wave (panel B) filling transport at mitral valve closing in patients (N=9) undergoing CRT with different AV delay settings, compared with healthy volunteers (N=3). The data in each column are plotted as univariate scatter plots and summarized in the form of boxplots. In the patients, red and blue boxplots refer respectively CRTOFF and different AV delay cases. Each symbol type refers to a different patient, and is colored in green (red) if CRT makes the corresponding variable more (less) similar to the healthy subjects. The latter are represented by a green boxplot.

The present study is based on the analysis of 9 patients with heart failure (HF) and cardiac resynchronization therapy (CRT) under different atrioventricular (AV) delays and 3 healthy volunteers matched by age and gender to the patient group. Patients were consecutively enrolled from the pacemaker outpatient clinic. Controls were selected from a large database of healthy volunteers recruited at our institutions [32]. The study protocol was approved by the local institutional review committee, and all subjects provided written informed consent for this study. Clinical data are summarized in Table 4. As summarized in Table 4, three normal subjects (VOL1-3) and nine patients undergoing CRT (CRT1-9) were considered. Patient CRT7 is used as example in FIGS. 6-8 and 10. Each patient is labeled with the symbol used to represent their data in FIG. 8 is and 10.

TABLE 4

Summary of study population data.

| ID | Age | Gender | H.R. (bpm) | EF (%) | CRT OFF | AVOPT (ms) | AVMAX (ms) | AVMIN (ms) | 100 bpm |
|---|---|---|---|---|---|---|---|---|---|
| VOL1 | 73 | F | 60 | 71 | NORMAL | — | — | — | — |
| VOL2 | 55 | F | 70 | 56 | NORMAL | — | — | — | — |

TABLE 4-continued

Summary of study population data.

| ID | Age | Gender | H.R. (bpm) | EF (%) | CRT OFF | AVOPT (ms) | AVMAX (ms) | AVMIN (ms) | 100 bpm |
|---|---|---|---|---|---|---|---|---|---|
| VOL3 | 66 | M | 59 | 71 | NORMAL | — | — | — | — |
| CRT1 (○) | 70 | F | CRT dep. | 52 | YES | 110 | 200 | 70 | NO |
| CRT2 (□) | 78 | F | CRT dep. | 38 | YES | 110 | 180 | 70 | NO |
| CRT3 (◇) | 59 | M | CRT dep. | 39 | YES | 90 | 200 | 70 | NO |
| CRT4 (▷) | 62 | M | CRT dep. | 14 | YES | 90 | 150 | 70 | NO |
| CRT5 (◁) | 80 | M | CRT dep. | 51 | YES | 110 | 170 | 70 | YES |
| CRT6 (▽) | 62 | F | CRT dep. | 31 | YES | 110 | 210 | 70 | NO |
| CRT7 (△) | 57 | F | CRT dep. | 29 | YES | 110 | 170 | 70 | YES |
| CRT8 (✕) | 65 | F | CRT dep. | 30 | YES | 120 | 160 | 100 | YES |
| CRT9 (✦) | 59 | M | CRT dep. | 43 | YES | 80 | 180 | 70 | NO |

H.R: Heart rate,
EF: Ejection fraction,
NORMAL: normal volunteer;
CRT dep: CRT dependent.

Reproducibility Analysis

Reproducibility analysis of the processed data was performed in seven subjects randomly selected from a large Doppler Echocardiographic study database. Inclusion was based on the absence of known or suspected cardiovascular disease, a normal EKG, a normal Doppler-echocardiographic exam, and no history of hypertension or diabetes.

AV Delay Settings and Data Acquisition

In the patient group, ultrasound sequences were acquired at 5 different programming settings to analyze the effect of pacing (CRT on vs CRT off), the AV delay and the heart rate. Patients were studied in spontaneous sinus rhythm at 3 different AV delay settings: maximum AV (AVMAX), minimum AV (AVMIN), optimum AV (AVOPT). Then, maintaining the optimum AV delay, images were again acquired at 100 bpm induced by atrial pacing. Finally, patients were studied after turning off the cardiac pacing (CRTOFF). Maximum AV delay was obtained by increasing AV delay until capture was lost due to intrinsic conduction. Minimum AV delay was obtained by decreasing it down to 80 ms. The optimum AV delay was set using the iterative method, which uses the mitral valve pulsed wave Doppler to optimize the diastolic filling time (DFT). The iterative method attempts to obtain the longest DFT time that does not truncate the A-wave, achieving maximal separation between the E- and the A-waves. Briefly, DFT was measured from the start of the E-wave until the end of the A-wave. A long AV delay was programmed and reduced in 20-ms steps until A-wave truncation. The interval was then increased in 10 ms increments, and the shortest AV delay without A-wave truncation was selected to maximize the DFT [12].

Comprehensive echocardiographic examinations were performed using a Vivid 7 ultrasound machine with 2-4 MHz transducers (GE Healthcare). For each particular CRT-device setting, we obtained 2D color-Doppler and B-mode (grayscale) sequences from the long-axis apical view. In addition, pulsed-wave Doppler recordings were obtained from the 5-chamber apical view, carefully located to obtain spectral recordings of opening and closing of the mitral and aortic valves. Event timings of the cardiac cycle were measured from these recordings, and then forwarded to the fluid-dynamic solver [32].

2D Image Analysis and Intraventricular Flow Processing

The LV myocardial wall was segmented using speckle-tracking software to delineate the endocardial boundary (EchoPac v.110.1.2, GE Healthcare). We reconstructed the time-dependent flow field inside the LV using 2D echo-CDV, as previously described and validated in vitro [33] and in vivo [32]. Conventional Doppler-echocardiographic data was measured following current recommendations [34].

Blood Transport Assessment

Blood Transport Equation for Virtual MULTI-COLOR Angiography

Using the time-dependent 2D echo-CDV velocity field $v(x,t)$ and the cardiac chamber wall tracking data as input, the inventors solved an advection equation for a passive scalar field $\psi$ with uniform initial conditions and step-wise Dirichlet inflow boundary conditions, $$\frac{D\psi}{Dt} = \partial_t \psi + \nabla \cdot (v\psi) = 0,$$

$\psi(x, t=0) = \psi_0 = \text{const}$,
$\psi(x_{inlet}, 0 < t < t_1) = \psi_1 = \text{const}$,
$\psi(x_{inlet}, t_1 \leq t < t_2) = \psi_2 = \text{const}$,
etc.

This continuous semi-Lagrangian approach tags different volumes of blood with different numerical values that are transported by the flow, thereby simulating the visualization of distinct virtual contrast media inside the cardiac chamber. For instance, one can implement a two-step inlet boundary condition to track the evolution of the two fluid volumes that enter the LV during the E wave and the A wave. Blood is a complex multi-component suspension for which it is generally accepted that the mass diffusivity of different species is negligible compared to momentum diffusivity [35,36]. Thus, we did not include a diffusive term in the transport equation. This approach is analogous to previous analyses of intracardiac blood transport based on the deterministic integration of fluid particle trajectories [22,26,25,24,23,28]. Note that the absence of diffusive terms makes it possible to integrate equation 1 backward in time applying Dirichlet boundary conditions at the outlet of the domain. As shown below, combining the results from the forward and backward integrations allows for a straightforward categorization of blood transport templates inside the cardiac chambers. Equation (1) was numerically integrated using previously described in-house software written in FORTRAN [37]. The equation was discretized on a Cartesian grid by a $2^{nd}$-order finite volume method, and a total variation diminishing flux limiting scheme [36] was used to avoid numerical oscillations at the sharp interfaces created between volumes of blood with different inflow tags.

Characterization of Blood Transport Patterns

The time-evolving distribution of ψ was automatically thresholded to track the blood carried by the transport structures generated during the E-wave and A-wave, and to determine the size of these structures and their frontal position. Equation (A) was integrated with uniform initial conditions and two different inlet boundary conditions for the E wave and A wave (e.g. ψ(x, t=0)=0, ψ($x_{inlet}$, t∈E wave)=1 and ψ($x_{inlet}$, t∈A wave)=2). The iso-contours ψ=0, 1, 2 allowed us to track the time-evolving distribution of the blood that entered the LV during both filling waves, together with that of the residual volume of blood occupying the LV at the onset of diastole. E and A wave sizes, $S_E$ and $S_A$, were calculated from the area they occupied in the imaging plane, and normalized by the total end-diastolic LV area in the same plane. To systematically analyze the effect of AV delay on LV filling transport, we determined the fraction of LV size occupied by the E and A waves, $S_E/S_{LV}$ and $S_A/S_{LV}$, as well as the normalized apical position of each wave's front $X_E/L$ and $X_A/L$, where L is the long axis length of the LV (i.e. X/L=0 is the LV base and X/L=1 is the LV apex).

In addition to tracking the filling transport patterns, we analyzed the spatiotemporal evolution of the blood that is ejected each cardiac cycle by integrating equation (1) backwards in time with uniform initial conditions, and Dirichlet boundary conditions at the aortic valve annulus. Combining the results from the backward and forward integrations allowed us to automatically identify the following transport structures: direct flow (DF, blood that enters and exits the LV in the same cardiac cycle), retained inflow (RI, incoming blood that is not ejected during the same cycle), delayed ejection (DE, ejected blood that entered the LV in a previous cardiac cycle) and residual flow (RF, blood that entered the LV in a previous cycle and is not ejected in the current cycle, therefore residing in the LV for at least two cardiac cycles) [22]. For the purpose of this 2D study we used the respective planar-volumes (areas) to account for each of these fractions.

To assess the kinematic efficiency of flow redirection inside the LV under CRT, we determined the size, kinetic energy density and acceleration of each transport region at the onset of systole. Kinetic energy density was calculated from 2D echo-CDV data as $K(x,t)=|v|^2/2$. Fluid acceleration was calculated as $$m(x, t_0) = \left(\frac{\partial v}{\partial t} + v \cdot \nabla v\right).$$

These variables were spatially integrated over the surface occupied by each transport region to obtain their overall values inside the region (e.g. $M_{DF}=\int_{S_{DF}} m(x)dx$). It is important to note that M is a vector that not only indicates the magnitude of the acceleration of each fluid volume, but also its direction. The orientation of the whole ventricle's M with respect with the ventricular long axis has been recently shown to correlate with long-term outcome in patients undergoing CRT [31]. We calculated the ratio $\eta_K=K_{DF}/K_{LV}$ at aortic valve opening in all the patients to determine if CRT changes contributed to efficiently focusing the inflow kinetic energy into the volume of fluid that was ejected during systole. The ratio of direct flow area to total LV area in the imaging plane, $\eta_{DF}=S_{DF}/S_{LV}$, was also computed to quantify the efficiency of volumetric blood transport within one cardiac cycle.

In addition to focusing kinetic energy into the direct flow volume, efficient LV blood transit from the inflow to the outflow tract requires a marked change in the direction of fluid motion. A measure of the efficiency of this process is the net acceleration transferred to the direct flow region in the direction of the LV outflow tract normalized with the total magnitude of this acceleration, $$\eta_M = \frac{M_{DF} \cdot e_{LVOT}}{|M_{DF}|},$$

where $e_{LVOT}$ is the unitary vector parallel to the direction of the LV outflow tract, pointing outwards the LV. The calculation of the 2D+t velocity field, the integration of equation (A) and the post processing work were programmed to be automatic and operator-independent. Best and worst full time for the entire post-processing from RAW echo images were 10 and 20 minutes (13±3 min).

Reproducibility (fully blinded echocardiographic image acquisition and re-acquisition, calculation of 2D flow velocity fields, event-time identification, and final index computation by two independent observers; n=7 normal subjects) was good for most calculated indices (Table 5: Intraclass correlation coefficient (Ric) and relative error (mean±std) of the reproducibility study).

TABLE 5

| Parameter | Intraobserver | | Interobserver | |
|---|---|---|---|---|
| | $R_{ic}$ | Relative Error (%) | $R_{ic}$ | Relative Error (%) |
| $S_{DF}/S_{LV}$ ($\eta_{DF}$) | 0.75 | 1 ± 20 | 0.85 | 17 ± 13 |
| $S_{RI}/S_{LV}$ | 0.46 | 20 ± 26 | 0.51 | 14 ± 27 |
| $S_{DE}/S_{LV}$ | 0.70 | 3 ± 34 | 0.69 | 22 ± 27 |
| $S_{RF}/S_{LV}$ ($\lambda_{RF}$) | 0.68 | 14 ± 18 | 0.84 | 12 ± 23 |
| $S_E/S_{LV}$ | 0.73 | 24 ± 22 | 0.77 | 24 ± 14 |
| $S_A/S_{LV}$ | 0.53 | 11 ± 42 | 0.53 | 1 ± 39 |

$S_{DF}$: Direct flow,
$S_{RI}$: Retained inflow,
$S_{DE}$: Delayed ejection,
$S_{RF}$: Residual flow and,
$S_{LV}$: Whole LV planar volumes.
$S_E/S_{LV}$ and $S_A/S_{LV}$, fraction of LV size occupied by the E and A waves.

Statistical Analysis

Individual scatterplots and boxplots showing the median and interquartile range are shown for each parameter. Differences among phases are compared using linear mixed effects accounting for repeated measured within each subject (random effect). Reproducibility of quantitative indices was analyzed using the intraclass correlation coefficient ($R_{ic}$). All analyses were performed in R (v. 3.2) and p values<0.05 were considered significant.

Results

Figure 6:
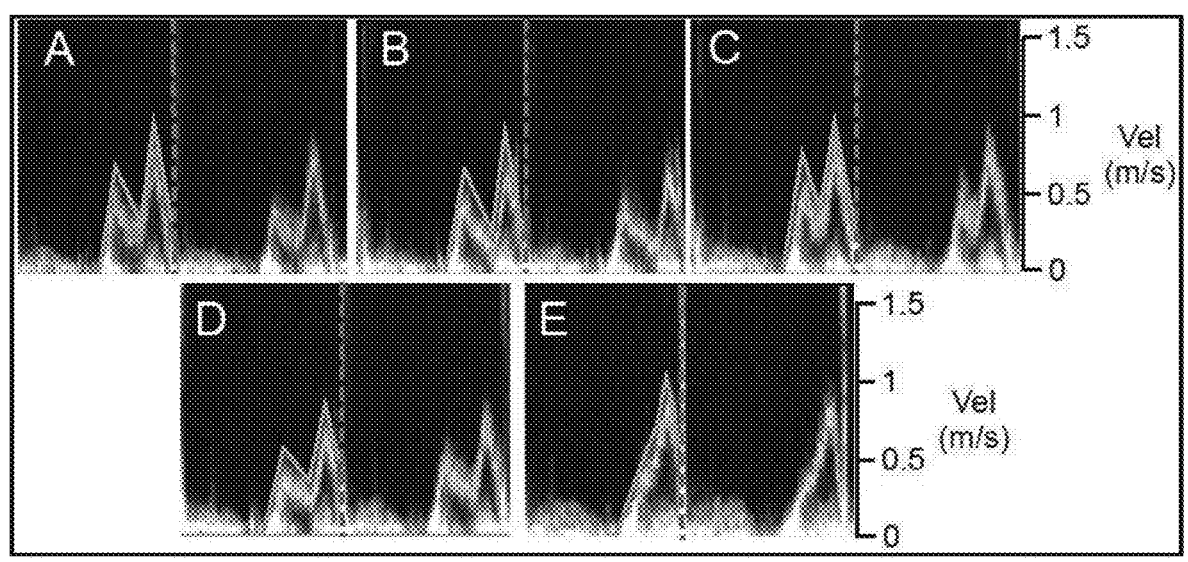
FIG. 6 demonstrates pulse wave Doppler inflow velocity as a function of time in a patient without CRT (A), and undergoing CRT at AVOPT (B), AVMAX (C), AVMIN (D), and atrial pacing at 100 bpm(E). In all the panels, the inflow velocity envelope is shown in green and the mitral valve closure time is represented by a red-dashed vertical line. Notice the truncation of the A wave for AVMIN, shortening the timing of atrial driven filling, and the fusion of the E and A waves for tachycardia.

Intraventricular Inflow and Blood Transport Under Cardiac Resynchronization Therapy CRT and AV delay optimization modify the inflow velocity profile in patients implanted with bi-ventricular pacemakers. This is illustrated in FIG. 6, which displays pulsed wave Doppler (PW) measurements from a representative patient (CRT7, see Table 4) for each one of the 5 different pacing settings. The PW profiles exhibit the two flow velocity envelopes that define left-ventricular filling flow: the E-wave representing the early, passive filling phase of the LV, and the A-wave representing the late active filling phase driven by atrial contraction. Varying the AV delay displaces the start and end of these waves in time, and modulates the magnitude and timing of the inflow velocity, leading therefore to different intraventricular flow fields.

Atrioventricular Delay and Blood Transport During Early and Late Filling

The AV delay has a number of effects not only on global chamber mechanics but also on myocardial fiber pre-stretching and contraction [38]. Consequently, as said above, changes in AV delay modify the dynamics of the filling flow driven by the E and A waves. FIG. 7 illustrates these differences for the same patient shown in FIG. 6. The total amount of blood entering the LV varied between 26% and 42% of the LV area in the imaged plane for the pacing settings considered, in fair agreement with the patient's measured ejection fraction of 29% measured at AVOPT. More importantly, both the size (i.e. area) and shape of the regions defined by E-wave and A-wave filling were sensitive to the presence of pacing (CRTON vs CRTOFF), the AV delay, and the heart rate (Table 6: Results of E and A wave tracking at mitral valve closing (average±standard deviation)). In the patient group, CRT increased the fraction of LV volume occupied by the E wave at the end of diastole, bringing this variable closer to the healthy range (FIG. 8, panel A). The observed increase in early LV filling volume was particularly noticeable for AVOPT, where 6 out of the 9 patients experienced an increase in $S_E/S_{LV}$. We found a similar trend for CRT to increase the apical position of the E-wave front (Table 7). Moreover, CRT caused a moderate increase in the late filling volume fraction $S_A/S_{LV}$ (FIG. 8, panel B).

TABLE 6

|  | OFF | AVOPT | AVMIN | AVMAX | 100 BPM | NORMALS |
|---|---|---|---|---|---|---|
| $X_E/L$ | 0.81 ± 0.14 | 0.82 ± 0.12 | 0.83 ± 0.14 | 0.87 ± 0.11 | 0.51 ± 0.16 | 0.75 ± 0.08 |
| $X_A/L$ | 0.45 ± 0.16 | 0.45 ± 0.23 | 0.30 ± 0.20 | 0.51 ± 0.22 |  | 0.47 ± 0.12 |
| $S_E/S_{LV}$ | 0.18 ± 0.1 | 0.20 ± 0.06 | 0.21 ± 0.08 | 0.18 ± 0.07 | 0.15 ± 0.10 | 0.28 ± 0.04 |
| $S_A/S_{LV}$ | 0.10 ± 0.05 | 0.15 ± 0.07 | 0.10 ± 0.06 | 0.13 ± 0.06 |  | 0.16 ± 0.08 |

$X_E/L$ and $X_A/L$: normalized apical position of each E and A waves.
$S_E/S_{LV}$ and $S_A/S_{LV}$, fraction of LV size occupied by the E and A waves.

Time-Evolution of Intraventricular Transport Regions

Figure 9:
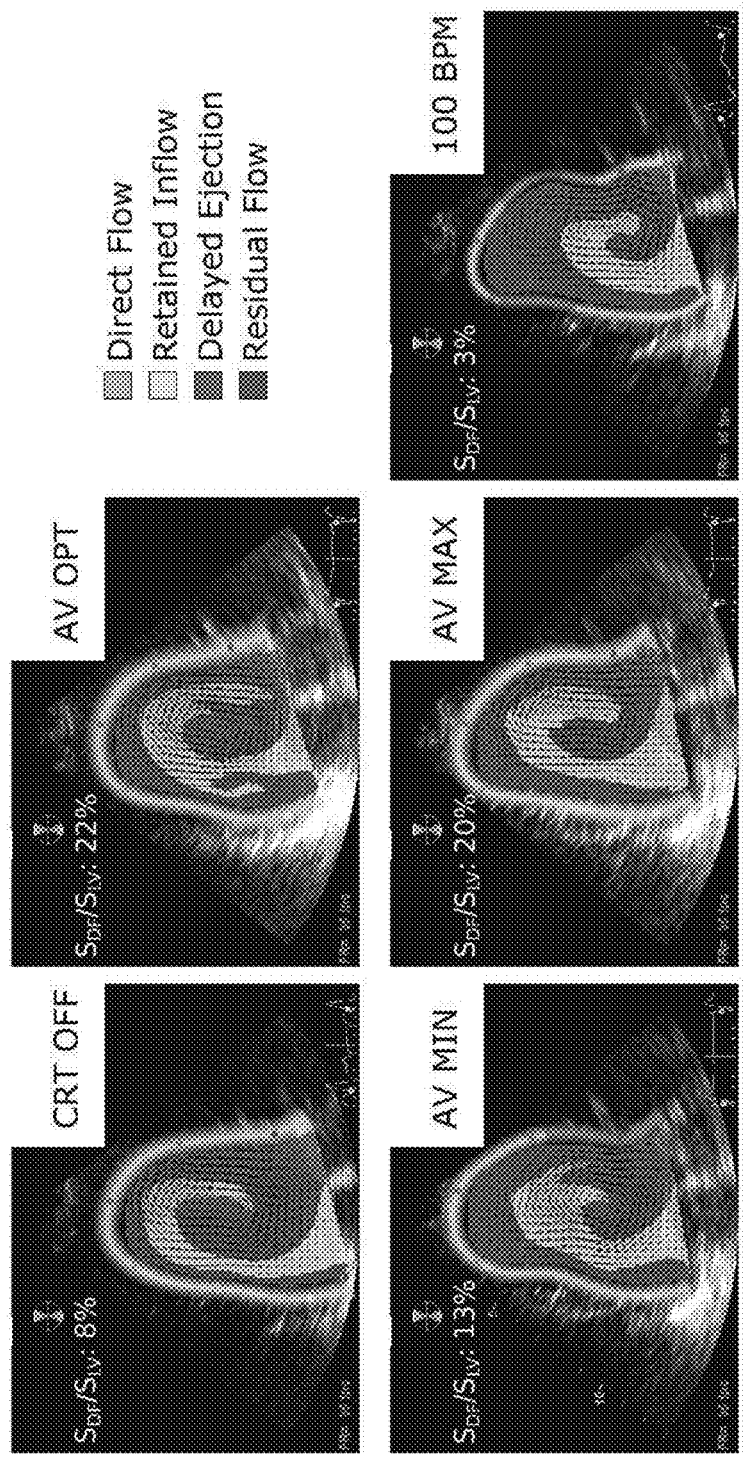
FIG. 9 demonstrates end-diastolic distribution of different transport regions in the LV of the same patient shown in FIGS. 1-3, plotted for different CRT settings (CRTOFF, AVOPT, AVMIN, AVMAX and Tachycardia). The different regions represented are direct flow (green), retained inflow (yellow), delayed ejection (blue) and residual flow (red).
Figure 10:
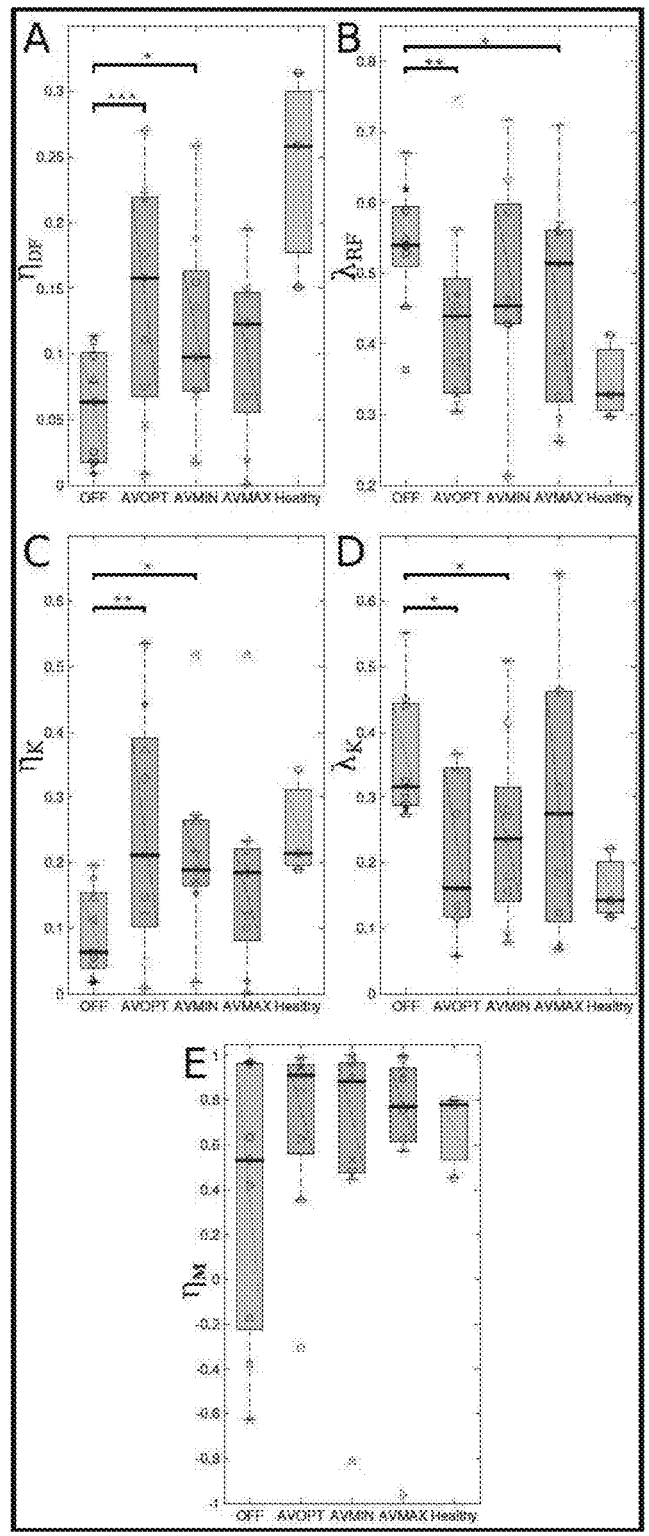
FIG. 10 demonstrates statistics of intraventricular blood redirection efficiency at aortic valve opening in patients (N=9) undergoing CRT with different AV delay settings, compared with healthy volunteers (N=3). A) Fraction of LV volume that undergoes direct flow in the imaged plane, $\eta_{DF} = S_{DF}/S_{LV}$. B) Fraction of LV occupied by residual volume in the imaged plane, $\lambda_{RF} = S_{RF}/S_{LV}$. C) Fraction of total kinetic energy in the LV contained in the direct flow region, $\lambda_K = K_{RF}/K_{LV}$. D) Fraction of total kinetic energy in the LV contained in the residual volume, $\eta_K = K_{DF}/K_{LV}$. E) Net acceleration communicated to the direct flow region in the direction of the outflow tract, normalized by the total acceleration magnitude, $$\eta_M = \frac{M_{DF} \cdot e_{LVOT}}{|M_{DF}|}.$$

FIG. 9 displays the end-diastolic distribution of the direct flow, retained inflow, delayed ejection and residual flow regions in the LV of the representative patient shown in FIGS. 6-7. In the absence of pacing, the overall transit of LV blood transport followed a wide arch, so that a large fraction of LV volume in the center of the chamber remained as residual flow. CRT altered this effect increasing direct flow, particularly for AVOPT. With tachycardia, the filling and ejection phases were shortened and defined small transport regions that did not intersect significantly, consequently creating a small amount of direct flow. FIG. 10 (panel A) and Table 7 (Table 7: Average±standard deviation of relative end-diastolic flow fractions of the LV for the different CRT settings compared with reference values obtained by PCMRI [25,23,22]) summarize the statistics of $\eta_{DF}$ (ratio of direct flow area to total LV area) as a function of AV delay in the patient population, including reference data from healthy subjects and previous studies. Consistent with FIG. 9, AVOPT shows a significant increment in the direct flow region with respect to the CRTOFF condition in the whole population; $\eta_{DF}$ increased in 7 of the 9 patients, and the median $\eta_{DF}$ increased by a factor of –3. The variation of $\eta_{DF}$ was less pronounced for the two other AV delay settings, though $\eta_{DF}$ increased in 7 out of 9 patients for both AVMIN and AVMAX. In addition to increasing direct flow, CRT enhanced the efficiency of LV blood transit by decreasing the portion of the chamber occupied by residual volume, defined as $\lambda_{RF}=S_{RF}/S_{LV}$ (FIG. 10, B). Eight out 9 patients reduced their residual volumes at AVOPT. Nevertheless, AVMAX also provided a significant effect ($\lambda_{RF}$ decreased in 7/9 patients). Reproducibility test-retest for all the volumetric indices ($\eta_{DF}$, $S_{RF}/S_{LV}$, $S_{DE}/S_{LV}$, $\lambda_{RF}$, $S_E/S_{LV}$, and $S_A/S_{LV}$) showed fair agreement both in the intraobserver and interobserver analysis (Table 5).

TABLE 7

|  | OFF | AVopt | AVmin | AVmax | 100 bpm | Healthy | Eriksson et al. (2010) | Eriksson et al. (2010) | Fredriksson et al. (2011) | Bolger et al. (2007) | Bolger et al. (2007) |
|---|---|---|---|---|---|---|---|---|---|---|---|
| N | 9 | 9 | 9 | 9 | 9 | 3 | 13 | 1* | 10 | 17 | 1* |
| $S_{DF}/S_{LV}$ ($\eta_{DF}$) | 0.06 ± 0.04 | 0.14 ± 0.09 | 0.12 ± 0.07 | 0.10 ± 0.06 | 0.06 ± 0.05 | 0.24 ± 0.08 | 0.37 ± 0.05 | 0.08 | 0.44 ± 0.06 | 0.21 ± 0.06 | 0.04 |
| $S_{RF}/S_{LV}$ | 0.23 ± 0.07 | 0.24 ± 0.07 | 0.23 ± 0.10 | 0.26 ± 0.09 | 0.16 ± 0.11 | 0.20 ± 0.04 | 0.17 ± 0.04 | 0.25 | 0.17 ± 0.03 | 0.27 ± 0.08 | 0.31 |
| $S_{DE}/S_{LV}$ | 0.17 ± 0.04 | 0.17 ± 0.08 | 0.17 ± 0.06 | 0.17 ± 0.06 | 0.13 ± 0.08 | 0.21 ± 0.02 | 0.16 ± 0.03 | 0.28 | 0.15 ± 0.03 | 0.27 ± 0.06 | 0.26 |

TABLE 7-continued

| | OFF | AVopt | AVmin | AVmax | 100 bpm | Healthy | Eriksson et al. (2010) | Eriksson et al. (2010) | Fredriksson et al. (2011) | Bolger et al. (2007) | Bolger et al. (2007) |
|---|---|---|---|---|---|---|---|---|---|---|---|
| $S_{RF}/S_{LV}$ ($\lambda_{RF}$) | 0.54 ± 0.09 | 0.45 ± 0.14 | 0.48 ± 0.15 | 0.46 ± 0.15 | 0.66 ± 0.17 | 0.35 ± 0.06 | 0.30 ± 0.05 | 0.37 | 0.23 ± 0.06 | 0.24 ± 0.12 | 0.39 |

$S_{DF}$: Direct flow,
$S_{RI}$: Retained inflow,
$S_{DE}$: Delayed ejection,
$S_{RF}$: Residual flow and,
$S_{LV}$: Whole LV planar volumes.
*in the results by Eriksson et al, Fredriksson et al. and Bolger et al account for a patient with dilated cardiomyopathy.

The inventors found $\eta_K$ (ratio of direct flow kinetic energy to total LV total kinetic) to be higher in the healthy subjects than in the patients with CRTOFF. Furthermore, there was a clear trend of increase in $\eta_K$ with CRT that was relatively insensitive to the AV delay. Additionally, CRT decreased the amount of inflow kinetic energy that remained in the residual volume at the end of diastole, $\lambda_K = K_{RF}/K_{LV}$. The observed decrease in wasted kinetic energy was most significant for AVOPT and AVMIN, with $\lambda_K$ showing variations in 8 and 9 (out of 9) patients respectively (FIG. 10, D, Table 5).

FIG. 10 panel E and Table 8 (Flow kinematic efficiency parameters obtained at aortic valve opening (average±standard deviation)) summarize the statistics of $\eta_M$ (fraction of direct flow acceleration in the direction of the LV outflow tract) at the onset of systole. Similar to $\eta_{DF}$ and $\eta_K$, this directional parameter efficiency became higher with CRT regardless of the AV delay, showing an increase in 6 out of 9 patients for AVMIN, AVMAX and AVOPT.

Overall, the presented data imply that the spatio-temporal evolution of the intraventricular blood flow in a patients undergoing CRT can be highly sensitive to heart rate and AV delay. The blood flow in the CRTOFF condition is driven by a persistent clockwise swirling pattern that is typically found in patients with dilated cardiomyopathy [32,28], forcing the blood entering the LV to follow an arched path along the inferolateral and anteroseptal LV walls. Turning CRT on modified this transport pattern, particularly for AVOPT. For the latter CRT setting, the incoming blood was distributed forming a pattern consistent with a more symmetric starting jet-vortex ring structure.

In addition to having an effect on LV filling, CRT may potentially improve the efficient redirection of left ventricular blood inflow towards the outflow tract by: 1) modifying the transport patterns to increase the amount of blood coming into the LV each cardiac cycle that is ejected in the same cardiac cycle (i.e. direct flow), 2) increasing the

TABLE 8

| | OFF | AVopt | AVmin | AVmax | 100 bpm | NORMALS |
|---|---|---|---|---|---|---|
| $\eta_K$ | 0.09 ± 0.07 | 0.25 ± 0.18 | 0.22 ± 0.13 | 0.18 ± 0.15 | 0.07 ± 0.09 | 0.25 ± 0.08 |
| $\lambda_K$ | 0.36 ± 0.10 | 0.26 ± 0.21 | 0.25 ± 0.14 | 0.29 ± 0.20 | 0.49 ± 0.30 | 0.16 ± 0.05 |
| $\eta_M$ | 0.37 ± 0.61 | 0.70 ± 0.43 | 0.60 ± 0.57 | 0.62 ± 0.61 | 0.76 ± 0.27 | 0.68 ± 0.20 |

$\eta_K$: ratio of total kinetic energy in the volume of fluid that is focused into the direct flow region;
$\lambda_K$: ratio of total kinetic energy in the volume of fluid that is focused into the residual flow region;
$\eta_M$: net acceleration transferred to the direct flow region in the direction of the LV outflow tract normalized with the total magnitude of this acceleration.

Discussion

In the present study the inventors implement a high-throughput method, suitable for visualizing and measuring flow transport in the LV using ultrasound in the clinical setting. This method is based on a continuous semi-Lagrangian formulation that allowed the inventors to track and to determine quantitative metrics of LV volume fractions from flow velocity measurements with no user interaction. As a result, this method provides accurate maps of blood transport without the need to integrate the trajectories of a large number of virtual blood particles and to perform semi-manual segmentation of the delineated fluid structures, as previously done using either phase-contrast MR [22] or Doppler-echocardiography [28]. The inventors' data compare well with previous studies using phase-contrast MR in healthy and diseased hearts, as shown in Table 4.

The inventors used manual modification of CRT pacemaker parameters to illustrate the clinical potential of this novel tool, and demonstrated acute changes in blood transport patterns inside the LV with different AV delays. As shown, flow organization inside the LV is highly dynamic and sensitive to the timing of cardiac events. Even a moderate increase in heart rate induced important changes in the manner LV flow affects the transit of blood from the mitral valve to the aorta.

amount of kinetic energy that is transferred from incoming blood to ejected blood, and 3) aligning the motion of the ejected blood with the left ventricular outflow tract. Furthermore, our results and the emerging literature imply that CRT favors the generation of coherent intraventricular pressure gradients that accelerate blood in the direction of the LV outflow tract [31]. Finally, the impact of different transport patterns on intraventricular flow mixing and prevention of blood stasis needs to be addressed [37].

Flow transport visualization methods such as the one presented in this study are readily applicable to large patient populations and are therefore particularly well suited to clarify issues such as the effect of CRT on LV blood transport. This is supported by the relatively good agreement between the presented data and previous studies using PC-MR, especially in the diseased heart (see Table 7). From a clinical perspective, this method opens the possibility of using flow imaging techniques to optimize CRT. Flow transport visualization methods not only will help investigators to understand the physiological basis of heart failure but also to optimize pharmacological and non-pharmacological therapies to improve the outcomes associated with one of the most prevalent diseases in the world.

The echocardiographic 2D approach disclosed herein has important practical advantages, as it provides high temporal and spatial resolutions, is fast, clinically feasible, and does not require infusion of contrast agents. Moreover, the proposed transport analysis methodology relies on clinical access to time-resolved LV velocity fields, but it is independent of the particular imaging modality employed to measure intraventricular velocity.

Blood transport patterns in the LV can be readily derived from flow-velocity fields by solving a passive-scalar advection partial differential equation. This continuous semi-Lagrangian method disclosed here is suitable for high-throughput processing without the need of discrete particle tracking or user interaction. Combining this tool with color-Doppler ultrasound, the inventors have demonstrated important effects of cardiac resynchronization therapy and atrioventricular delay optimization on intraventricular blood transport.

Example 3

A pilot study was designed to address the effectiveness of an ultrasound-based method for measuring stasis through the blood Residence Time ($T_R$), in patients with an anterior acute myocardial infarction (AMI). Blood Residence Time represents the time that a blood region spends in the LV before being redirected to the aorta. In particular, this study aimed to test whether stasis maps were sensitive to identify quantitative flow abnormalities in patients developing left ventricular thrombus (LVT) in the acute phase of AMI.

Methods

Study Population 73 consecutive patients admitted to our institution for a first anterior AMI from July 2013 to January 2016 were prospectively enrolled (Table 9). Inclusion criteria were: 1) sinus rhythm, 2) absence of >2 aortic regurgitation (due to methodological limitations to calculate residence time metrics), 3) an LV ejection fraction ≤45% during the first 72 h of AMI onset, 4) no previous history of myocardial infarction, 5) stable clinical status, and 6) willingness to sign the informed consent. Clinical variables were prospectively collected. An institutional review board approved the study, and all participants provided written informed consent.

TABLE 9

|  | Overall | No LV Thrombus | LV Thrombus | p value |
|---|---|---|---|---|
| N | 73 | 59 | 14 |  |
| Age (yrs) | 60.7 + 13.8 | 61.3 + 14.3 | 58.2 + 11 | 0.377 |
| Sex (Male | Female) | 17 (23%) | 16 (27%) | 1 (7%) | 0.158 |
| Cardiovascular Medications |  |  |  |  |
| Beta-blocker | 63 (86%) | 51 (86%) | 12 (86%) | 1 |
| ACEI/ARB | 63 (86%) | 52 (88%) | 11 (79%) | 1 |
| Diuretic | 7 (10%) | 7 (12%) | 0 (0%) | 0.325 |
| Statins | 72 (100%) | 59 (100%) | 13 (100%) | — |

Image Acquisition and Stasis Imaging and Quantification

A flow-chart of the image processing methods used in this studs is summarized in FIG. 11.

Results

Clinical Data and Outcomes

Clinical data of the cohort is summarized in Table 10. Demographic, clinical and medication variables were not significantly different between patients with and without LVT. Patients diagnosed with intraventricular thrombosis received oral anticoagulation. Patients diagnosed with LVT in either study were pooled for analyses.

TABLE 10

|  | No LV Thrombus | LV Thrombus | p value Thrombus vs no Thrombus |
|---|---|---|---|
| Conventional Echocardiography |  |  |  |
| End-diastolic volume index (mL/m$^2$) | 56.38 ± 13.3 | 57.5 ± 20.65 | 0.792 |
| End-systolic volume index (mL/m$^2$) | 32.01 ± 10.11 | 33.82 ± 16.48 | 0.582 |
| Ejection Fraction (%) | 0.44 ± 0.09 | 0.42 ± 0.1 | 0.549 |
| End-diastolic diameter (cm) | 4.67 ± 0.6 | 4.73 ± 0.61 | 0.764 |
| End-systolic diameter (cm) | 3.52 ± 0.71 | 3.49 ± 0.65 | 0.927 |
| LV Global Stasis |  |  |  |
| $T_{r,s}$ (s) | 1.94 ± 0.78 | 2.34 ± 0.87 | 0.034* |
| Regional Stasis indices after 2 s |  |  |  |
| $V_{TR}$ (%) | 0.35 ± 0.16 | 0.50 ± 0.15 | 0.006* |
| $T_{RM}$ (s) | 3.92 ± 1.03 | 4.45 ± 1.03 | 0.097 |
| $X_M$ (%) | 0.63 ± 0.11 | 0.63 ± 0.09 | 0.954 |
| $C_M$ (m) | 0.11 ± 0.03 | 0.13 ± 0.03 | 0.024* |

*p < 0.05 LVT vs no-LVT

Imaging Studies

Patients with and without LVT showed similar values of conventional echocardiographic variables (FIG. 12), including end-systolic volume index (58±21 vs. 56±13 mL/m2, p=0.79) and ejection fraction (0.42±0.1 vs 0.44±0.09, p=0.55).

Global residence time of blood in the LV was significantly longer in early studies in patients with LVT ($T_R$=2.34±0.87 sec vs. 1.94±0.78 sec, p=0.034). Compared to patients without LVT, intraventricular regions of stasis (clusters of blood volume with $T_R$>2 sec) were also larger (0.50±0.15 vs 0.35±0.16, p=0.006) and had a longer perimeter of endocardial contact (0.13±0.03 vs 0.11±0.03 m, p=0.024) in patients developing LVT. These differences were confirmed by a longer residence time of the near-wall flow adjacent to the apical segments (5.09±1.55 vs. 3.90±1.47 s, p=0.017).

CONCLUSIONS

In this study, it was demonstrated that correct interpretation of $T_R$ derived parameters more accurately identified those patients with an increased risk of blood stasis, which can lead to thrombogenesis, than conventional echocardiography.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. Indeed, various modifications of the invention in addition to those described herein will become apparent to those skilled in the art from the foregoing description and the accompanying figures. Such modifications are intended to fall within the scope of the appended claims It is further to be understood that all values are approximate, and are provided for description. Patents, patent applications, publications, product descriptions, and protocols are cited throughout this application, the disclosures of which are incorporated herein by reference in their entireties for all purposes.

REFERENCES

Arboix A, Alio J. 2010. Cardioembolic stroke: clinical features, specific cardiac disorders and prognosis. Curr Cardiol Rev 6: 150-61

Bakalli A, Georgievska-Ismail L, Kocinaj D, Musliu N, Krasniqi A, Pllana E. 2013. Prevalence of left chamber cardiac thrombi in patients with dilated left ventricle at sinus rhythm: the role of transesophageal echocardiography. J Clin Ultrasound 41: 38-45

Bermejo J, Benito Y, Alhama M, Yotti R, Martinez-Legazpi P, et al. 2014. Intraventricular vortex properties in non-ischemic dilated cardiomyopathy. Am J Physiol Heart Circ Physiol 306: H718-29

Bermejo J, Martinez-Legazpi P, del Alamo J C. 2015. The Clinical Assessment of Intracardiac Flows. Ann Rev Fluid Mech 47: 315-42

Bluestein D. 2004. Research approaches for studying flow-induced thromboembolic complications in blood recirculating devices. Expert Rev Med Devices 1: 65-80

Bolger A F, Heiberg E, Karlsson M, Wigstrom L, Engvall J, et al. 2007. Transit of blood flow through the human left ventricle mapped by cardiovascular magnetic resonance. J Cardiovasc Magn Reson 9: 741-47

Busch J, Giese D, Wissmann L, Kozerke S. 2013. Reconstruction of divergence-free velocity fields from cine 3D phase-contrast flow measurements. Magn Reson Med 69: 200-10

Chorin A J. 1967. The numerical solution of the Navier-Stokes equations for an incompressible fluid. Bull. Am. Math. Soc. 73: 928-31

Devesa C, Rossini L, Martinez-Legazpi P, Perez del Villar C, Benito Y, et al. 2015. Prediction of intraventricular thrombosis by quantitative imaging of stasis: A pilot color-Doppler study in patients with acute myocardial infarction. J Am Coll Cardiol 65 (10 S)

Eriksson J, Bolger A F, Ebbers T, Carlhall C J. 2013. Four-dimensional blood flow-specific markers of L V dysfunction in dilated cardiomyopathy. Eur Heart J Cardiovasc Imaging 14: 417-24

Eriksson J, Carlhall C J, Dyverfeldt P, Engvall J, Bolger A F, Ebbers T. 2010. Semi-automatic quantification of 4D left ventricular blood flow. J Cardiovasc Magn Reson 12: 9

Eriksson J, Dyverfeldt P, Engvall J, Bolger A F, Ebbers T, Carlhall C J. 2011. Quantification of presystolic blood flow organization and energetics in the human left ventricle. Am J Physiol Heart Circ Physiol 300: H2135-41

Esmaily-Moghadam M, Hsia T Y, Marsden A L. 2013. A non-discrete method for computation of residence time in fluid mechanics simulations. Phys Fluids 25 Fournier R L. 2012. Basic transport phenomena in biomedical engineering. Boca Raton: CRC Press. xxiii, 459 pages pp.

Garcia-Alvarez A, Fernandez-Friera L, Garcia-Ruiz J M, Nuno-Ayala M, Pereda D, et al. 2013. Noninvasive monitoring of serial changes in pulmonary vascular resistance and acute vasodilator testing using cardiac magnetic resonance. J Am Coll Cardiol 62: 1621-31

Garcia D, Del Alamo J C, Tanne D, Yotti R, Cortina C, et al. 2010. Two-dimensional intraventricular flow mapping by digital processing conventional color-Doppler echocardiography images. IEEE Trans Med Imaging 29: 1701-13

Gardiner C W. 2004. Handbook of stochastic methods for physics, chemistry, and the natural sciences. Berlin; New York: Springer. 415 pages pp.

Gonzalez G, Jimenez-Carretero D, Rodriguez-Lopez S, Kumamaru K K, George E, et al. 2015. Automated Axial Right Ventricle to Left Ventricle Diameter Ratio Computation in Computed Tomography Pulmonary Angiography. PLoS One 10: e0127797

Hendabadi S, Bermejo J, Benito Y, Yotti R, Fernandez-Aviles F, et al. 2013. Topology of blood transport in the human left ventricle by novel processing of Doppler echocardiography. Ann Biomed Eng 41: 2603-16

Homma S, Thompson J L, Pullicino P M, Levin B, Freudenberger R S, et al. 2012. Warfarin and aspirin in patients with heart failure and sinus rhythm. N Engl J Med 366: 1859-69

Hong G R, Pedrizzetti G, Tonti G, Li P, Wei Z, et al. 2008. Characterization and quantification of vortex flow in the human left ventricle by contrast echocardiography using vector particle image velocimetry. J Am Coll Cardiol Img 1: 705-17

Jozsa J, Kramer T. 2000. Modelling Residence Time as Advection-Diffusion With Zero-Order Reaction Kinetics. Proceedings of the Hydroinformatics 2000 Conference, Cedar Rapids, Iowa.

Kilner P J, Yang G Z, Wilkes A J, Mohiaddin R H, Firmin D N, Yacoub M H. 2000. Asymmetric redirection of flow through the heart. Nature 404: 759-61

Kormos R L. 2015. Left ventricular assist device pump thrombosis: Understanding mechanisms as a key to causality. J Thorac Cardiovasc Surg 149: 673-4

Lang R M, Badano L P, Mor-Avi V, Afilalo J, Armstrong A, et al. 2015. Recommendations for cardiac chamber quantification by echocardiography in adults: an update from the American Society of Echocardiography and the European Association of Cardiovascular Imaging. J Am Soc Echocardiogr 28: 1-39 e14

Leonard E F, Grabowski E F, Turitto V T. 1972. The role of convection and diffusion on platelet adhesion and aggregation. Ann N Y Acad Sci 201: 329-42

LeVeque R J. 2002. Finite-volume methods for hyperbolic problems. Cambridge; New York: Cambridge University Press. xix, 558 pages pp.

Lowe G D. 2003. Virchow's triad revisited: abnormal flow. Pathophysiol Haemost Thromb 33: 455-7

Mangual J O, Domenichini F, Pedrizzetti G. 2012. Describing the highly three dimensional Right Ventricle flow. Ann Biomed Eng 40: 1790-801

Massie B M, Collins J F, Ammon $S_E$, Armstrong P W, Cleland J G, et al. 2009. Randomized trial of warfarin, aspirin, and clopidogrel in patients with chronic heart failure: the Warfarin and Antiplatelet Therapy in Chronic Heart Failure (WATCH) trial. Circulation 119: 1616-24

May-Newman K, Wong Y K, Adamson R, Hoagland P, Vu V, Dembitsky W. 2013. Thromboembolism is linked to intraventricular flow stasis in a patient supported with a left ventricle assist device. ASAIO J 59: 452-5

Mittal R, Dong H, Bozkurttas M, Najjar F M, Vargas A, von Loebbecke A. 2008. A versatile sharp interface immersed boundary method for incompressible flows with complex boundaries. Journal of Computational Physics 227: 4825-52

Mody N A, King M R. 2007. Influence of Brownian motion on blood platelet flow behavior and adhesive dynamics near a planar wall. Langmuir 23: 6321-8

Peattie R A. 2013. Transport phenomena in biomedical engineering principles and practices. pp. 1 volume (various pagings). Boca Raton: CRC Press, Quaini A, Canic S, Paniagua D. 2011. Numerical characterization of hemodynamics conditions near aortic valve after implantation of Left Ventricular Assist Device. Math Biosci Eng 8: 785-806

Rodriguez Munoz D, Markl M, Moya Mur J L, Barker A, Fernandez-Golfin C, et al. 2013. Intracardiac flow visualization: current status and future directions. Eur Heart J Cardiovasc Imaging 14: 1029-38

Tarbell J M. 2003. Mass transport in arteries and the localization of atherosclerosis. Annu Rev Biomed Eng 5: 79-118

Toeg H D, Al-Atassi T, Garcia J P, Ruel M. 2014. An update on mechanical circulatory support for heart failure therapy. Curr Opin Cardiol 29: 167-73

Watanabe H, Sugiura S, Hisada T. 2008. The looped heart does not save energy by maintaining the momentum of blood flowing in the ventricle. Am J Physiol Heart Circ Physiol 294: H2191-6

Wigstrom L, Ebbers T, Fyrenius A, Karlsson M, Engvall J, et al. 1999. Particle trace visualization of intracardiac flow using time-resolved 3D phase contrast MRI. Magn Reson. Med. 41: 793-99

Wong K, Samaroo G, Ling I, Dembitsky W, Adamson R, et al. 2014. Intraventricular flow patterns and stasis in the LVAD-assisted heart. J Biomech 47: 1485-94

Zhang B, Gao C, Hou Q, Yin J, Xie L, et al. 2012. Different independent susceptibility markers for first-ever cerebral infarction and myocardial infarction in young patients. J Neurol 259: 1420-5

1. Guha K, McDonagh T (2013) Heart failure epidemiology: European perspective. Curr Cardiol Rev 9 (2):123-127
2. Farwell D, Patel N R, Hall A, Ralph S, Sulke A N (2000) How many people with heart failure are appropriate for biventricular resynchronization? Eur Heart J 21 (15): 1246-1250. doi:10.1053/euhj.1999.1985
3. Kass D A (2005) Cardiac resynchronization therapy. J Cardiovasc Electrophysiol 16 Suppl 1:S35-41. doi: 10.1111/j.1540-8167.2005.50136.x
4. Xiao H B, Roy C, Fujimoto S, Gibson D G (1996) Natural history of abnormal conduction and its relation to prognosis in patients with dilated cardiomyopathy. Int J Cardiol 53 (2):163-170
5. Xiao H B, Brecker S J, Gibson D G (1992) Effects of abnormal activation on the time course of the left ventricular pressure pulse in dilated cardiomyopathy. Br Heart J 68 (4):403-407
6. Littmann L, Symanski J D (2000) Hemodynamic implications of left bundle branch block. J Electrocardiol 33 Supp1:115-121
7. Saxon L A, Kerwin W F, Cahalan M K, Kalman J M, Olgin J E, Foster E, Schiller N B, Shinbane J S, Lesh M D, Merrick S H (1998) Acute effects of intraoperative multisite ventricular pacing on left ventricular function and activation/contraction sequence in patients with depressed ventricular function. J Cardiovasc Electrophysiol 9 (1):13-21
8. Kerwin W F, Botvinick E H, O'Connell J W, Merrick S H, DeMarco T, Chatterjee K, Scheibly K, Saxon L A (2000) Ventricular contraction abnormalities in dilated cardiomyopathy: effect of biventricular pacing to correct interventricular dyssynchrony. J Am Coll Cardiol 35 (5):1221-1227
9. Bristow M R, Saxon L A, Boehmer J, Krueger S, Kass D A, De Marco T, Carson P, DiCarlo L, DeMets D, White B G, DeVries D W, Feldman A M, Investigators C (2004) Cardiac-resynchronization therapy with or without an implantable defibrillator in advanced chronic heart failure. New England Journal of Medicine 350 (21):2140-2150
10. Pedrizzetti G, Domenichini F (2005) Nature optimizes the swirling flow in the human left ventricle. Phy Rev Lett 95 (10):108101
11. Gorcsan J, 3rd, Abraham T, Agler D A, Bax J J, Derumeaux G, Grimm R A, Martin R, Steinberg J S, Sutton M S, Yu C M, American Society of Echocardiography Dyssynchrony Writing G, American Society of Echocardiography Dyssynchrony Writing G, Heart Rhythm S (2008) Echocardiography for cardiac resynchronization therapy: recommendations for performance and reporting—a report from the American Society of Echocardiography Dyssynchrony Writing Group endorsed by the Heart Rhythm Society. J Am Soc Echocardiogr 21 (3):191-213. doi:10.1016/j.echo.2008.01.003
12. Stanton T, Hawkins N M, Hogg K J, Goodfield N E, Petrie M C, McMurray J J (2008) How should we optimize cardiac resynchronization therapy? Eur Heart J 29 (20):2458-2472. doi:10.1093/eurheartj/ehn380
13. Pavlopoulos H, Nihoyannopoulos P (2010) Recent advances in cardiac resynchronization therapy: echocardiographic modalities, patient selection, optimization, non-responders—all you need to know for more efficient CRT. Int J Cardiovasc Imaging 26 (2):177-191. doi: 10.1007/s10554-009-9523-5
14. Waggoner A D, De Las Fuentes L, Faddis M N, Gleva M J, Spence K E, Davila-Roman V G (2008) Left ventricular diastolic filling prior to cardiac resynchronization therapy: implications for atrioventricular delay programming. Pacing Clin Electrophysiol 31 (7):838-844. doi:10.1111/j.1540-8159.2008.01097.x
15. Zhang Q, Fung J W H, Chan Y S, Chan H C K, Lin H, Chan S, Yu C M (2008) The role of repeating optimization of atrioventricular interval during interim and long-term follow-up after cardiac resynchronization therapy. Int J Cardiol 124 (2):211-217. doi:10.1016/j.ijcard.2007.02.043
16. Auricchio A, Stellbrink C, Sack S, Block M, Vogt J, Bakker P, Huth C, Schondube F, Wolfhard U, Bocker D, Krahnefeld O, Kirkels H, Pacing Therapies in Congestive H (2002) Long-term clinical effect of hemodynamically optimized cardiac resynchronization therapy in patients with heart failure and ventricular conduction delay. J Am Coll Cardiol 39 (12):2026-2033
17. Sawhney N S, Waggoner A D, Garhwal S, Chawla M K, Osborn J, Faddis M N (2004) Randomized prospective trial of atrioventricular delay programming for cardiac resynchronization therapy. Heart Rhythm 1 (5):562-567. doi:10.1016/j.hrthm.2004.07.006
18. Kedia N, Ng K, Apperson-Hansen C, Wang C H, Tchou P, Wilkoff B L, Grimm R A (2006) Usefulness of atrioventricular delay optimization using Doppler assessment of mitral inflow in patients undergoing cardiac resynchronization therapy. Am J Cardiol 98 (6):780-785
19. Kilner P J, Yang G Z, Wilkes A J, Mohiaddin R H, Firmin D N, Yacoub M H (2000) Asymmetric redirection of flow through the heart. Nature 404 (6779):759-761
20. Richter Y E E (2006) Cardiology is flow. Circulation 113 (23):2679-2682
21. Yang G Z, Merrifield R, Masood S, Kilner P J (2007) Flow and myocardial interaction: an imaging perspective. Philos Trans R Soc Lond B Biol Sci 362 (1484):1329-1341. doi:10.1098/rstb.2007.2119
22. Bolger A F, Heiberg E, Karlsson M, Wigstrom L, Engvall J, Sigfridsson A, Ebbers T, Kvitting J P, Carlhall C J, Wranne B (2007) Transit of blood flow through the human left ventricle mapped by cardiovascular magnetic resonance. J Cardiovasc Magn Reson 9 (5):741-747
23. Fredriksson A G, Zajac J, Eriksson J, Dyverfeldt P, Bolger A F, Ebbers T, Carlhall C J (2011) 4-D blood flow in the human right ventricle. Am J Physiol Heart Circ Physiol 301 (6):H2344-2350. doi:10.1152/ajpheart.00622.2011
24. Eriksson J, Dyverfeldt P, Engvall J, Bolger A F, Ebbers T, Carlhall C J (2011) Quantification of presystolic blood flow organization and energetics in the human left ventricle. Am J Physiol Heart Circ Physiol 300 (6):H2135-2141. doi:10.1152/ajpheart. 00993.2010
25. Eriksson J, Carlhall C J, Dyverfeldt P, Engvall J, Bolger A F, Ebbers T (2010) Semi-automatic quantification of 4D left ventricular blood flow. J Cardiovasc Magn Reson 12:9. doi:10.1186/1532-429X-12-9
26. Eriksson J, Bolger A F, Ebbers T, Carlhall C J (2013) Four-dimensional blood flow-specific markers of L V dysfunction in dilated cardiomyopathy. Eur Heart J Cardiovasc Imaging 14 (5):417-424. doi:10.1093/ehjci/jes159
27. Wigstrom L, Ebbers T, Fyrenius A, Karlsson M, Engvall J, Wranne B, Bolger A F (1999) Particle trace visualization of intracardiac flow using time-resolved 3D phase contrast Mitt Magn ResonMed 41 (4):793-799
28. Hendabadi S, Bermejo J, Benito Y, Yotti R, Fernandez-Aviles F, Del Alamo J C, Shadden S C (2013) Topology of blood transport in the human left ventricle by novel processing of Doppler echocardiography. Ann Biomed Eng 41 (12):2603-2616. doi:10.1007/s10439-013-0853-z
29. Benito Y, Bermejo J, Alhama M, Yotti R, Perez del Villar C, Martinez-Legazpi P, González-Mansilla A, Barrio A, Fernandez-Aviles F, del Alamo J C (2012) Heart rate and AV delay modify left ventricular filling vortex properties. Circulation 126:A18099
30. Goliasch G, Goscinska-Bis K, Caracciolo G, Nakabo A, Smolka G, Pedrizzetti G, Narula J, Sengupta P P (2013) CRT improves LV filling dynamics: insights from echocardiographic particle imaging velocimetry. JACC Cardiovasc Imaging 6 (6):704-713. doi:10.1016/j.jcmg.2013.04.004
31. Pedrizzetti G, Martiniello A R, Bianchi V, D'Onofrio A, Caso P, Tonti G (2015) Changes in electrical activation modify the orientation of left ventricular flow momentum: novel observations using echocardiographic particle image velocimetry. Eur Heart J Cardiovasc Imaging. doi:10.1093/ehjci/jev137
32. Bermejo J, Benito Y, Alhama M, Yotti R, Martinez-Legazpi P, Perez del Villar C, Perez-David E, Gonzalez-Mansilla A, Santa-Marta C, Barrio A, Fernandez-Aviles F, del Alamo J C (2014) Intraventricular vortex properties in non-ischemic dilated cardiomyopathy. Am J Physiol Heart Circ Physiol 306 (5):H718-729. doi:10.1152/ajpheart.00697.2013
33. Garcia D, Del Alamo J C, Tanne D, Yotti R, Cortina C, Bertrand E, Antoranz J C, Perez-David E, Rieu R, Fernandez-Aviles F, Bermejo J (2010) Two-dimensional intraventricular flow mapping by digital processing conventional color-Doppler echocardiography images. IEEE Trans Med Imaging 29 (10):1701-1713. doi:10.1109/tmi.2010.2049656
34. Lang R M, Badano L P, Mor-Avi V, Afilalo J, Armstrong A, Ernande L, Flachskampf F A, Foster E, Goldstein S A, Kuznetsova T, Lancellotti P, Muraru D, Picard M H, Rietzschel E R, Rudski L, Spencer K T, Tsang W, Voigt J U (2015) Recommendations for cardiac chamber quantification by echocardiography in adults: an update from the American Society of Echocardiography and the European Association of Cardiovascular Imaging. J Am Soc Echocardiogr 28 (1):1-39 e14. doi:10.1016/j.echo.2014.10.003
35. Bermejo J, Martinez-Legazpi P, del Alamo J C (2015) The Clinical Assessment of Intracardiac Flows. Ann Rev Fluid Mech 47:315-342. doi:10.1146/annurev-fluid-010814-014728
36. Tarbell J M (2003) Mass transport in arteries and the localization of atherosclerosis. Annu Rev Biomed Eng 5:79-118. doi:10.1146/annurev.bioeng.5.040202.121529
37. Rossini L, Martinez-Legazpi P, Vu V, Fernandez-Friera L, Perez del Villar C, Rodriguez-López S, Benito Y, Borja M-G, Pastor-Escuredo D, Yotti R, Ledesma-Carbayo M J, Kahn A M, Ibanez B, Fernandez-Aviles F, May-Newman K, Bermejo J, del Alamo J C (2015) A clinical method for mapping and quantifying blood stasis in the left ventricle. J Biomech In press
38. Zwanenburg J J, Gotte M J, Kuijer J P, Hofman M B, Knaapen P, Heethaar R M, van Rossum A C, Marcus J T (2005) Regional timing of myocardial shortening is related to prestretch from atrial contraction: assessment by high temporal resolution MRI tagging in humans. Am J Physiol Heart Circ Physiol 288 (2):H787-794
39. Gharib M, Rambod E, Kheradvar A, Sahn D J, Dabiri J O (2006) Optimal vortex formation as an index of cardiac health. Proc Natl Acad Sci USA 103 (16):6305-6308. doi:10.1073/pnas.0600520103
40. Martinez-Legazpi P, Bermejo J, Benito Y, Yotti R, Perez Del Villar C, Gonzalez-Mansilla A, Barrio A, Villacorta E, Sanchez P L, Fernandez-Aviles F, del Alamo J C (2014) Contribution of the diastolic vortex ring to left ventricular filling. J Am Coll Cardiol 64 (16):1711-1721. doi:10.1016/j.jacc.2014.06.1205
41. Seo J H, Mittal R (2013) Effect of diastolic flow patterns on the function of the left ventricle. Phys Fluids 25: 110801
42. Watanabe H, Sugiura S, Hisada T (2008) The looped heart does not save energy by maintaining the momentum of blood flowing in the ventricle. Am J Physiol Heart Circ Physiol 294 (5):H2191-2196. doi:10.1152/ajpheart.00041.2008
43. Thompson R B, McVeigh E R (2003) Fast measurement of intracardiac pressure differences with 2D breath-hold phase-contrast M M. Magn Reson Med 49 (6):1056-1066

What is claimed is:

1. A method for identifying regions of blood flow stasis inside a cardiac chamber or a blood vessel of a subject comprising:
   obtaining flow-velocity images of blood inside the cardiac chamber or the blood vessel of the subject;
   calculating one or more of residence time ($T_R$), standard deviation of residence time ($\sigma_R$), kinetic energy, or rate of distortion of blood particles inside the cardiac chamber or the blood vessel using the flow-velocity images to generate numerical metrics of blood flow; and
   generating one or more maps comprising a residence time ($T_R$) map, a kinetic energy map, a rate of distortion map, or combinations thereof, using the numerical metrics to identify and characterize the regions of blood flow stasis, wherein identifying and characterizing the regions of blood flow stasis comprises:
      identifying one or more regions of blood flow stasis from the generated maps, wherein each region of blood flow stasis has blood flow residence time greater than a threshold value; and
      for each region of blood flow stasis:
         generating a time-varying blood residence time feature for the region of blood flow stasis, comprising, for each of multiple time points within a cardiac cycle, spatially averaging blood residence time over the region of blood flow stasis at the time point; and
         temporally averaging the time-varying blood residence time feature for the region of blood flow stasis to generate a temporally-averaged blood residence time feature for the region of blood flow stasis.

2. The method of claim 1, wherein generating the numerical features of blood flow comprises calculating the blood flow's residence time ($T_R$) inside the cardiac chamber or the blood vessel.

3. The method of claim 1, wherein generating the numerical features of blood flow comprises calculating the standard deviation of the blood flow's residence time ($\sigma_R$) inside the cardiac chamber or the blood vessel.

4. The method of claim 3, further comprising calculating the standard deviation of the blood flow's residence time in the regions with blood flow residence time greater than the threshold value inside the cardiac chamber or the blood vessel.

5. The method of claim 1, wherein generating the numerical features of blood flow comprises calculating the blood flow's kinetic energy inside the cardiac chamber or the blood vessel.

6. The method of claim 5, further comprising calculating the blood flow's kinetic energy in the regions with blood flow residence time greater than the threshold value inside the cardiac chamber or the blood vessel.

7. The method of claim 1, wherein generating the numerical features of blood flow comprises calculating the rate of distortion of blood flow inside the cardiac chamber or the blood vessel.

8. The method of claim 7, further comprising calculating the blood flow's rate of distortion in the regions with blood flow residence time greater than the threshold value inside the cardiac chamber or the blood vessel.

9. The method of claim 1, further comprising calculating a size or a shape of the regions with blood flow residence time greater than the threshold value.

10. The method of claim 1, wherein obtaining flow-velocity images of blood particles inside the cardiac chamber or the blood vessel of the subject comprises obtaining flow-velocity images of blood particles inside the left ventricular chamber, left atrium chamber, left atrial appendage, right-ventricular chamber, or right atrium chamber.

11. The method of claim 1, wherein obtaining flow-velocity images of blood particles inside the cardiac chamber or the blood vessel is performed using a medical image-based apparatus able to determine blood flow velocity field.

12. The method of claim 11, wherein medical image-based apparatus is an echocardiogram apparatus, a magnetic resonance imaging (MRI) apparatus, an echocardiographic imaging apparatus, a 2D color-Doppler velocimetry (echo-CDV) apparatus, an echo particle image velocimetry (echo-PIV) apparatus, a synthetic aperture ultrasound apparatus, a transverse oscillation ultrasound vector velocimetry apparatus, speckle-tracking apparatus, or vector flow mapping apparatus.

13. The method of claim 1, wherein the flow-velocity images comprise one, two, or three-dimensional images resolved in time.

14. The method of claim 1, wherein multiple flow-velocity images are obtained using different velocity scales, and wherein data from the obtained flow-velocity images are retrospectively merged to generate the flow map, the residence time ($T_R$) map, the kinetic energy map, the rate of distortion map, or combinations thereof.

15. The method of claim 1, wherein calculating one or more of the residence time ($T_R$), the standard deviation of residence time ($\sigma_R$), the kinetic energy, or the rate of distortion of blood particles inside the cardiac chamber or the blood vessel using the flow-velocity images to generate the numerical metrics of blood flow comprises calculating the residence time ($T_R$) of blood particles utilizing the equation:

$$\frac{\partial T_R}{\partial t} + \nabla \cdot (\vec{v} T_R) = 1.$$

16. The method of claim 1, wherein the standard deviation of $T_R$ is caused by noise in the velocity measurements, and wherein calculating one or more of the residence time ($T_R$), the standard deviation of residence time ($\sigma_R$), the kinetic energy, or the rate of distortion of blood particles inside the cardiac chamber or the blood vessel using the flow-velocity images to generate the numerical metrics of blood flow comprises calculating the standard deviation of $T_R$ utilizing the equation:

$$\sigma_R(x,t) = \sqrt{S_R(x,t) - T_R^2(x,t)}$$

wherein $S_R$ and $T_R$ obey the equations:

$$\frac{\partial T_R}{\partial t} + \nabla \cdot (\vec{v} T_R) = 1 + \nabla \cdot (k \nabla T_R)$$

$$\frac{\partial S_R}{\partial t} + \nabla \cdot (\vec{v} S_R) = 2 T_R + \nabla \cdot (k \nabla S_R),$$

and wherein diffusivity coefficient k represents uncertainty introduced by the noise in the velocity measurements.

17. The method of claim 1, wherein the flow-velocity images of blood particles are flow-velocity images of blood particles without a contrast agent.

18. A method for calculating blood transport inside a cardiac chamber or a blood vessel comprising:
obtaining flow-velocity images of blood particles inside the cardiac chamber or the blood vessel;
calculating one or more of residence time ($T_R$), standard deviation of the residence time ($\sigma_R$), kinetic energy, or rate of distortion of blood particles inside the cardiac chamber or the blood vessel using the flow-velocity images to generate numerical metrics of blood flow; and
generating blood transport maps using numerical metrics to identify regions of decreased, increased, static or unaltered blood transit; and
identifying one or more regions of blood flow stasis from the generated maps, wherein each region of blood flow stasis has blood flow residence time greater than a threshold value; and
for each region of blood flow stasis:
generating a time-varying blood residence time feature for the region of blood flow stasis, comprising, for each of multiple time points within a cardiac cycle, spatially averaging blood residence time over the region of blood flow stasis at the time point; and
temporally averaging the time-varying blood residence time feature for the region of blood flow stasis to generate a temporally-averaged blood residence time feature for the region of blood flow stasis.

19. A method for calculating blood transport inside a cardiac chamber or a blood vessel comprising:
obtaining flow-velocity images of blood particles inside a cardiac chamber or blood vessel;
calculating residence time ($T_R$), standard deviation of the residence time ($\sigma_R$), kinetic energy, linear momentum blood particles, or combinations thereof, inside the cardiac chamber or the blood vessel using the flow-velocity images to generate numerical metrics of blood flow; and
generating blood transport maps using numerical metrics to identify different transit regions of blood; and
identifying one or more regions of blood flow stasis from the generated maps, wherein each region of blood flow stasis has blood flow residence time greater than a threshold value; and
for each region of blood flow stasis:
generating a time-varying blood residence time feature for the region of blood flow stasis, comprising, for each of multiple time points within a cardiac cycle, spatially averaging blood residence time over the region of blood flow stasis at the time point; and
temporally averaging the time-varying blood residence time feature for the region of blood flow stasis to generate a temporally-averaged blood residence time feature for the region of blood flow stasis.

20. A method for identifying regions of blood flow stasis inside a cardiac chamber or a blood vessel of a subject comprising:
  obtaining flow-velocity images of blood inside the cardiac chamber or the blood vessel of the subject;
  calculating one or more of residence time ($T_R$), standard deviation of residence time ($\sigma_R$), kinetic energy, or rate of distortion of blood particles inside the cardiac chamber or the blood vessel using the flow-velocity images to generate numerical metrics of blood flow, comprising, calculating the residence time ($T_R$) of blood particles utilizing the equation:

$$\frac{\partial T_R}{\partial t} + \nabla \cdot (\vec{v} T_R) = 1;$$

and
  generating one or more maps comprising a residence time ($T_R$) map, a kinetic energy map, a rate of distortion map, or combinations thereof, using the numerical metrics to identify and characterize the regions of blood flow stasis, wherein identifying and characterizing the regions of blood flow stasis comprises:
    identifying one or more regions with blood flow residence time greater than a threshold value from the generated maps; and
    generating, for each region with blood flow residence time greater than the threshold value, one or more numerical features of the region characterizing one or more of: a mobility of the region, a distance of the region to a chamber wall, a perimeter of the region in contact with the chamber wall, or a mean blood flow residence time in the region.

21. A method for identifying regions of blood flow stasis inside a cardiac chamber or a blood vessel of a subject comprising:
  obtaining flow-velocity images of blood inside the cardiac chamber or the blood vessel of the subject;
  calculating one or more of residence time ($T_R$), standard deviation of residence time ($\sigma_R$), kinetic energy, or rate of distortion of blood particles inside the cardiac chamber or the blood vessel using the flow-velocity images to generate numerical metrics of blood flow, comprising calculating the standard deviation of $T_R$ utilizing the equation:

$$\sigma_R(x,t) = \sqrt{S_R(x,t) - T_R^2(x,t)}$$

wherein $S_R$ and $T_R$ obey the equations:

$$\frac{\partial T_R}{\partial t} + \nabla \cdot (\vec{v} T_R) = 1 + \nabla \cdot (k \nabla T_R)$$

$$\frac{\partial S_R}{\partial t} + \nabla \cdot (\vec{v} S_R) = 2 T_R + \nabla \cdot (k \nabla S_R),$$

wherein diffusivity coefficient k represents uncertainty introduced by noise in velocity measurements in the flow-velocity images, and wherein the standard deviation of $T_R$ is caused by the noise in the velocity measurements in the flow-velocity images; and
  generating one or more maps comprising a residence time ($T_R$) map, a kinetic energy map, a rate of distortion map, or combinations thereof, using the numerical metrics to identify and characterize the regions of blood flow stasis, wherein identifying and characterizing the regions of blood flow stasis comprises:
    identifying one or more regions with blood flow residence time greater than a threshold value from the generated maps; and
    generating, for each region with blood flow residence time greater than the threshold value, one or more numerical features of the region characterizing one or more of: a mobility of the region, a distance of the region to a chamber wall, a perimeter of the region in contact with the chamber wall, or a mean blood flow residence time in the region.

* * * * *